(12) United States Patent
Nunes et al.

(10) Patent No.: US 7,674,907 B2
(45) Date of Patent: Mar. 9, 2010

(54) FURANOPYRIDINE DERIVATIVES AND METHODS OF USE

(75) Inventors: Joseph J. Nunes, Andover, MA (US); Matthew W. Martin, Cambridge, MA (US); Ryan White, Somerville, MA (US); David McGowan, Woluwe St. Pierre (BE); Jean E. Bemis, Arlington, MA (US); Frank Kayser, San Francisco, CA (US); Jiasheng Fu, Foster City, CA (US); Jinqian Liu, Palo Alto, CA (US); XianYun Jiao, San Mateo, CA (US)

(73) Assignee: Amgen Inc., Thousand Oaks, CA (US)

( * ) Notice: Subject to any disclaimer, the term of this patent is extended or adjusted under 35 U.S.C. 154(b) by 823 days.

(21) Appl. No.: 11/184,237

(22) Filed: Jul. 18, 2005

(65) Prior Publication Data

US 2006/0046977 A1    Mar. 2, 2006

Related U.S. Application Data

(60) Provisional application No. 60/590,472, filed on Jul. 23, 2004.

(51) Int. Cl.
*C07D 491/048* (2006.01)
*A61K 31/4355* (2006.01)
(52) U.S. Cl. ............... 546/115; 546/116; 514/302
(58) Field of Classification Search ........... 544/127; 514/233.8
See application file for complete search history.

(56) References Cited

FOREIGN PATENT DOCUMENTS

| EP | 1 396 489 | 3/2004 |
|---|---|---|
| JP | 11049777 A2 | 2/1999 |
| WO | 03/018589 A2 | 3/2003 |
| WO | 03/022852 A2 | 3/2003 |
| WO | 03/080064 A2 | 10/2003 |
| WO | 06/004658 A2 | 1/2006 |

OTHER PUBLICATIONS

Morissette et al., Advanced Drug Delivery Reviews, 56 (2004), 275-300.*
Bossharth, et al. Organic Letters (2003), 5, pp. 2441-2444.*
Ali, M.M. et al., "Synthesis of furo[2,3-d]pyrimidines and furo[2,3-b]pyridines" Indian J of Heterocyclic Chem., 4(3) 191-4 (1995).
Emmanuel Bossharth Et Al., "Palladium-mediated Three-component Synthesis of furo[2,3-b]pyridones by a one-pot Coub=pling of 3-Iodopyridones, Alkynes, and Organic Halides" Organic Letters, vol. 5, No. 14, 2003, pp. 2441-2444, XP002407815.

* cited by examiner

*Primary Examiner*—Rebecca L Anderson
*Assistant Examiner*—Shawquia Young
(74) *Attorney, Agent, or Firm*—G. Prabhakar Reddy

(57) ABSTRACT

The present invention relates to furanopyridine compounds having the general Formula I:

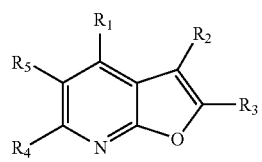

and stereoisomers, tautomers, solvates, pharmaceutically acceptable salts and derivatives, and prodrugs thereof. The invention also includes pharmaceutical compositions comprising a compound of Formula I, methods of modulating Lck and ACK-1 enzymes and of treating various related diseases and conditions, including inflammation, inhibition of T cell activation, proliferation, arthritis, organ transplant, ischemic or reperfusion injury, myocardial infarction, stroke, multiple sclerosis, inflammatory bowel disease, Crohn's disease, lupus, hypersensitivity, type 1 diabetes, psoriasis, dermatitis, Hashimoto's thyroiditis, Sjogren's syndrome, autoimmune hyperthyroidism, Addison's disease, autoimmune diseases, glomerulonephritis, allergic diseases, asthma, hayfever, eczema, cancer, colon carcinoma, thymoma, just to name a few, in a mammal, comprising administering to the mammal a therapeutically effective amount a compound of Formula I, as described above, and methods of manufacturing medicaments comprising the compound of Formula I.

13 Claims, No Drawings

FURANOPYRIDINE DERIVATIVES AND METHODS OF USE

This application claims the benefit of U.S. Provisional Application No. 60/590,472 filed Jul. 23, 2004, which is incorporated by reference herein.

FIELD OF THE INVENTION

The present invention generally relates to furanopyridine compounds, pharmaceutical formulations containing the compounds, methods of treatment using the compounds, and methods of preparing medicaments comprising the compounds.

BACKGROUND OF THE INVENTION

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor (TCR) which is expressed on the cell surface. This activation triggers a series of intracellular signaling cascades mediated by enzymes expressed within the cell (Kane, L P et al. Current Opinion in Immunol. 2000, 12, 242). These cascades lead to gene regulation events that result in the production of cytokines, like interleukin-2 (IL-2). IL-2 is a critical cytokine in T cell activation, leading to proliferation and amplification of specific immune responses.

One class of enzymes shown to be important in signal transduction is the kinase enzymes Members of the Src-family of tyrosine kinases include, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the src family of kinases would potentially lead to therapeutic benefit. Src(−/−) mice have abnormalities in bone remodeling or osteopetrosis (Soriano, P. Cell 1991, 64, 693), suggesting that inhibition of this kinase might be useful in diseases of bone resorption, such as osteoporosis. Lck(−/−) mice have defects in T cell maturation and activation (Anderson, S J et al. Adv. Immunol. 1994, 56, 151), suggesting that inhibition of this kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

Without wishing to imply that the compounds disclosed in the present invention possess pharmacological activity only by virtue of an effect on a single biological process, it is believed that the compounds modulate T cell activation by way of inhibition of one or more of the multiple protein tyrosine kinases involved in early signal transduction steps leading to T cell activation, for example by way of inhibition of Lck kinase.

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

Src kinases have also been found to be activated in tumors including sarcoma, melanoma, breast, and colon cancers suggesting that Src kinase inhibitors may be useful anti-cancer agents (Abram, C L and Courtneidge, S A Exp. Cell Res. 2000, 254, 1). Src kinase inhibitors have also been reported to be effective in an animal model of cerebral ischemia (R. Paul et al. Nature Medicine 2001, 7, 222), suggesting that Src kinase inhibitors may be effective at limiting brain damage following stroke.

Cancer is the second leading cause of death in the United States (Boring, et al., CA Cancer J. Clin., 43:7, 1993), and features uncontrolled cellular growth, which results either in local invasion of normal tissue or systemic spread (metastasis) of the abnormal growth. Cancer is caused by inherited or acquired mutations in cancer genes, which have normal cellular functions and which induce or otherwise contribute to cancer once mutated or expressed at an abnormal level. Certain well-studied tumors carry several different independently mutated genes, including activated oncogenes and inactivated tumor suppressor genes. Each of these mutations appears to be responsible for imparting some of the traits that, in aggregate, represent the full neoplastic phenotype (Land et al., Science, 222:771, 1983; Ruley, Nature, 4:602, 1983; Hunter, Cell, 64:249, 1991).

One such trait is gene amplification. Gene amplification involves a chromosomal region bearing specific genes undergoing a relative increase in DNA copy number, thereby increasing the copies of any genes that are present. In general, gene amplification results in increased levels of transcription and translation, producing higher amounts of the corresponding gene mRNA and protein. Amplification of genes causes deleterious effects, which contribute to cancer formation and proliferation (Lengauer et al. Nature, 396:643-649, 1999). Gene amplification has been established as an important genetic alteration in solid tumors (Knuutila et al., Am. J. Pathol., 152(5):1107-23, 1998; Knuutila et al., Cancer Genet. Cytogenet., 100(1):25-30, 1998).

Another trait of tumor cells is the over-expression or differential expression of whole collections of genes. In precancerous or cancerous cells, and tissues, where both amplification of a gene and over-expression of the gene product occur, then that gene and its product present both a diagnostic target as well as a therapeutic opportunity for intervention. In many cases, the amplified cancer genes encode an enzyme, such as a kinase, and the discovery and characterization of inhibitors of the enzymatic activity of this gene product will be a promising avenue that leads to novel therapeutics for cancer treatment.

ACK1 is a gene that is frequently amplified and over-expressed in primary human tumors (U.S. Patent Publication No. 20030175763). ACK1 kinase activity is regulated in the context of cell attachment and detachment, and certain cancer cells depend on ACK1's kinase activity for adhesion, anchorage independent growth and survival. Down regulation of ACK1 kinase activity or ACK1 expression levels can result in reduced tumor growth in animal models. Accordingly, Ack is a target believed to be useful in the regulation of cancer.

The ACK1 gene encodes an intracellular, non-receptor tyrosine kinase that binds cdc42Hs in its GTP-bound form and inhibits both the intrinsic and GTPase-activating protein (GAP)-stimulated GTPase activity of p21cdc42, a Ras-like protein involved in cell growth (Manser et al., Nature 363

(6427):364-367, 1993). This binding is mediated by a unique polypeptide of 47 amino acids C-terminal to an SH3 domain. ACK1 gene contains a tyrosine kinase domain and is reported to possess tyrosine kinase activity. The protein may be involved in a regulatory mechanism that sustains the GTP-bound active form of cdc42Hs and which is directly linked to a tyrosine phosphorylation signal transduction pathway.

While various groups have published on inhibitors of Src family kinase or ACK-1, disclosing various chemical compounds, including 2-phenylamino-imidazo [4,5-h]isoquinolin-9-ones (Snow, R J et al. J. Med. Chem. 2002, 45, 3394), pyrazolo [3,4-d]pyrimidines (Burchat, A F et al. Bioorganic and Med. Chem. Letters 2002, 12, 1987 and Hanke, J H et al. J. Biol. Chem. 1996, 271, 695), pyrrolo [2,3-d]pyrimidines (Altmann, E et al. Bioorganic and Med. Chem. Letters 2001, 11, 853), anilinoquinazolines (Wang, Y D et al. Bioorganic and Med. Chem. Letters 2000, 10, 2477), and imidazoquinoxalines (Chen, P. et al. Bioorganic and Med. Chem. Letters 2002, 12, 3153), none of these groups describe the compounds of the present invention. Further, none of these references describe, in particular, the compounds of the invention as modulators of kinase enzymes such as Lck and ACK-1, and useful for the regulation of T-cell mediated immune response, autoimmune disease, organ transplantation, allergies, asthma and cancer. Further, there is a need to develop novel modulators of kinase enzymes useful to treat inflammation, cancer and related proliferative conditions and diseases.

BRIEF DESCRIPTION OF EXEMPLARY EMBODIMENTS OF THE INVENTION

The present invention relates to compounds represented by general Formula I:

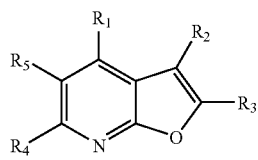

I and stereoisomers, tautomers, solvates, pharmaceutically acceptable salts and derivatives, and prodrugs thereof, wherein $R^1$, $R^2$, $R^3$, $R^4$ and $R^5$ are defined in the Detailed Description below. The compounds of Formula I are capable of modulating protein tyrosine kinases, such as Lck, Fyn(B), Fyn(T), Lyn, Src, Yes, Hck, Fgr and Blk, as well as other protein kinases such as Ack. Accordingly, these compounds are useful in the treatment, including preventative, prophylactic and therapeutic treatment, of protein tyrosine kinase-associated disorders such as immunologic and cancerous disorders.

"Protein tyrosine kinase-associated disorders" are disorders which result from aberrant tyrosine kinase activity, and/or which are alleviated by the regulation, and inhibition in particular, of one or more of these enzymes. For example, Lck inhibitors are of value in the treatment of a number of such disorders (for example, the treatment of autoimmune diseases), as Lck inhibition blocks T cell activation. In one embodiment of the invention, the compounds are useful for the treatment of T cell mediated diseases, including inhibition of T cell activation and proliferation. In another embodiment, the invention provides compounds which selectively block T cell activation and proliferation. Further, the compounds may block the activation of endothelial cell protein tyrosine kinase by oxidative stress thereby limiting surface expression of adhesion molecules that induce neutrophil binding, and they also can inhibit protein tyrosine kinase necessary for neutrophil activation. The compounds would be useful, therefore, in the treatment of ischemia and reperfusion injury.

In another embodiment of the invention, there are provided methods for the treatment of protein tyrosine kinase-associated disorders, comprising administering to a subject at least one compound of Formula I in an amount effective to treat the disorder. To this end, another embodiment of the invention provides a composition comprising a compound of Formula I and a pharmaceutically acceptable carrier. Such a composition can be administered to the subject, such as a mammal, for the purpose of treating the disorder. Other therapeutic agents such as those described below may be employed in combination with the inventive compounds, such as in a composition, in the present methods. Such other therapeutic agent(s) may be administered prior to, simultaneously with, or following the administration of the compound(s) of the present invention.

The compound(s) of the present invention may be used in treating various protein tyrosine kinase-associated disorders and related conditions including, without limitation, arthritis (such as rheumatoid arthritis, psoriatic arthritis or osteoarthritis); transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracielma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides methods for treating the aforementioned disorders such as atopic dermatitis by administration of a therapeutically effective amount of a compound of the present invention, which is an inhibitor of protein tyrosine kinase, to a patient suffering from dermatitis and potentially in need of such treatment.

The compounds of the invention are also active against other kinases, such as ACK-1. Modulating ACK-1 can be useful for treating various ACK-1-mediated proliferative diseases, such as cancer and cancer-related conditions. Accordingly, this is one route by which the compounds of the invention can be useful for treating cancer.

Src-family kinases other than Lck, such as Hck and Fgr, are important in the Fcγ receptor induced respiratory burst of neutrophils as well as the Fcγ receptor responses of monocytes and macrophages. The compounds of the present invention may inhibit the Fcγ induced respiratory burst response in neutrophils, and may also inhibit the Fcγ dependent production of TNFα. The ability to inhibit Fcγ receptor dependent neutrophil, monocyte and macrophage responses would result in additional anti-inflammatory activity for the present compounds in addition to their effects on T cells. This activity would be especially of value, for example, in the treatment of inflammatory diseases, such as arthritis or inflammatory bowel disease. The present compounds may also be of value for the treatment of autoimmune glomerulonephritis and other instances of glomerulonephritis induced by deposition of immune complexes in the kidney that trigger Fcγ receptor responses and which can lead to kidney damage.

In addition, certain Src family kinases, such as Lyn and Fyn(B), may be important in the Fcε receptor induced degranulation of mast cells and basophils that plays an important role in asthma, allergic rhinitis, and other allergic disease. Fcε receptors are stimulated by IgE-antigen complexes. The compounds of the present invention may inhibit the Fcε induced degranulation responses. The ability to inhibit Fcε receptor dependent mast cell and basophil responses may result in additional anti-inflammatory activity for the present compounds beyond their effect on T cells.

The combined activity of the present compounds towards monocytes, macrophages, T cells, etc. may prove to be a valuable tool in the treatment of any of the aforementioned disorders.

In another embodiment, the compounds are useful for the treatment of the aforementioned exemplary disorders irrespective of their etiology, for example, for the treatment of rheumatoid arthritis, transplant rejection, multiple sclerosis, inflammatory bowel disease, lupus, graft v. host disease, T cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The foregoing merely summarizes certain aspects of the invention and is not intended, nor should it be construed, as limiting the invention in any way.

DETAILED DESCRIPTION OF THE EXEMPLARY EMBODIMENTS OF THE INVENTION

In one embodiment, the present invention provides a compound of Formula I

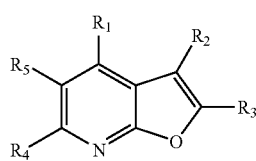

I or a stereoisomer, a tautomer, a solvate, a pharmaceutically acceptable salt or derivative, or a prodrug thereof, wherein $R^1$ is $NR^6R^7$, $OR^6$ or $SR^6$;
$R^2$ is $-R^{21}$, $-R^{21}-R^{22}$, $-R^{21}-R^{24}$, $-R^{22}-R^{24}$, $-R^{21}-R^{22}-R^{24}$, $-R^{21}-R^{23}-R^{24}$, $-R^{22}-R^{23}-R^{24}$, $-R^{21}-R^{23}-R^{22}-R^{24}$ or $-R^{21}-R^{22}-R^{23}-R^{24}$, any of which is substituted by 0, 1, 2, 3 or 4 substituents independently selected from $R^c$;
$R^3$ is $-R^{31}$, $-R^{31}-R^{32}$, $-R^{31}-R^{34}$, $-R^{32}-R^{34}$, $-R^{31}-R^{32}-R^{34}$, $-R^{31}-R^{33}-R^{34}$, $-R^{32}-R^{33}-R^{34}$, $-R^{31}-R^{33}-R^{32}-R^{34}$ or $-R^{31}-R^{32}-R^{33}-R^{34}$, any of which is substituted by 0, 1, 2, 3 or 4 substituents independently selected from $R^c$;
$R^4$ is $R^a$ or $R^c$;
$R^5$ is $R^a$ or $R^c$, alternatively $R^5$ taken together with $R^1$ form a partially or fully unsaturated 5 or 6-membered ring of carbon atoms and including 1, 2 or 3 heteroatoms selected from N, O and S, said ring optionally substituted with 1, 2 or 3 substituents independently selected from $R^b$ or $R^c$;
$R^6$ is $-R^{61}$, $-R^{62}$, $-R^{61}-R^{62}$, $-R^{61}-R^{64}$, $-R^{62}-R^{64}$, $-R^{61}-R^{62}-R^{64}$, $-R^{61}-R^{63}-R^{62}$, $-R^{61}-R^{63}-R^{64}$, $-R^{62}-R^{63}-R^{64}$, $-R^{61}-R^{63}-R^{62}-R^{64}$ or $-R^{61}-R^{62}-R^{63}-R^{64}$, any of which is substituted by 0, 1, 2, 3 or 4 substituents independently selected from $R^c$;
$R^7$ is $R^a$ or $R^c$, alternatively $R^7$ taken together with $R^6$ form a partially or fully unsaturated 5 or 6-membered ring of carbon atoms and including 1, 2 or 3 heteroatoms selected from N, O and S, said ring optionally substituted with 1, 2 or 3 substituents independently selected from $R^b$ or $R^c$;
$R^{21}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;
$R^{22}$ is, independently at each instance, $C_{1-8}$alkyl or $C_{1-8}$alkoxyl;
$R^{23}$ is, independently at each instance, $-C(=O)-$, $-C(=O)O-$, $-C(=O)NR^a-$, $-C(=NR^a)NR^a-$, $-O-$, $-OC(=O)-$, $-OC(=O)NR^a-$, $-OC(=O)N(R^a)S(=O)_2-$, $-OC_{2-6}$alkylNR^a-$, $-OC_{2-6}$alkylO-$, $-S-$, $-S(=O)-$, $-S(=O)_2-$, $-S(=O)_2NR^a-$, $-S(=O)_2N(R^a)C(=O)-$, $-S(=O)_2N(R^a)C(=O)O-$, $-S(=O)_2N(R^a)C(=O)NR^a-$, $-N(R^a)-$, $-N(R^a)C(=O)-$, $-N(R^a)C(=O)O-$, $-N(R^a)C(=O)N(R^a)-$, $-N(R^a)C(=NR^a)N(R^a)-$, $-N(R^a)S(=O)_2-$, $-N(R^a)S(=O)_2N(R^a)-$, $-NR^aC_{2-6}$alkylN(R^a)-$ or $-NR^aC_{2-6}$alkylO-$;
$R^{24}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;
$R^{31}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;
$R^{32}$ is, independently at each instance, $C_{1-8}$alkyl or $C_{1-8}$alkoxyl;
$R^{33}$ is, independently at each instance, $-C(=O)-$, $-C(=O)O-$, $-(=O)NR^a-$, $-C(=NR^a)NR^a-$, $-O-$, $-OC(=O)-$, $-OC(=O)NR^a-$, $-OC(=O)N(R^a)S(=O)_2-$, $-OC_{2-6}$alkylNR^a-$, $-OC_{2-6}$alkylO-$, $-S-$, $-S(=O)-$, $-S(=O)_2-$, $-S(=O)_2NR^a-$, $-S(=O)_2N(R^a)C(=O)-$, $-S(=O)_2N(R^a)C(=O)O-$, $-S(=O)_2N(R^a)C(=O)NR^a-$, $-N(R^a)-$, $-N(R^a)C$ (=O)—, —N($R^a$)C(=O)O—, —N($R^a$)C(=O)N($R^a$)—, —N($R^a$)C(=N$R^a$)N($R^a$)—, —N($R^a$)S(=O)$_2$—, —N($R^a$)S(=O)$_2$N($R^a$)—, —N$R^a$C$_{2-6}$alkylN($R^a$)— or —N$R^a$C$_{2-6}$alkylO—;

$R^{34}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{61}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{62}$ is, independently at each instance, C$_{1-8}$alkyl or C$_{1-8}$alkoxyl;

$R^{63}$ is, independently at each instance, —C(=O)—, —C(=O)O—, —(=O)N$R^a$—, —C(=N$R^a$)N$R^a$—, —O—, —OC(=O)—, —OC(=O)N$R^a$—, —OC(=O)N($R^a$)S(=O)$_2$—, —OC$_{2-6}$alkylN$R^a$—, —OC$_{2-6}$alkylO—, —S—, —S(=O)—, —S(=O)$_2$—, —S(=O)$_2$N$R^a$—, —S(=O)$_2$N($R^a$)C(=O)—, —S(=O)$_2$N($R^a$)C(=O)O—, —S(=O)$_2$N($R^a$)C(=O)N$R^a$—, —N($R^a$)—, —N($R^a$)C(=O)—, —N($R^a$)C(=O)O—, —N($R^a$)C(=O)N($R^a$)—, —N($R^a$)C(=N$R^a$)N($R^a$)—, —N($R^a$)S(=O)$_2$—, —N($R^a$)S(=O)$_2$N($R^a$)—, —N$R^a$C$_{2-6}$alkylN($R^a$)— or —N$R^a$C$_{2-6}$alkylO—;

$R^{64}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^a$ is, independently at each instance, H or $R^b$;

$R^b$ is, independently at each instance, C$_{1-8}$alkyl, phenyl, piperizinyl, pyridyl, piperidinyl, morpholinyl, pyrrolidinyl, pyrrolyl, imidazolyl, pyrrolidinonyl, pyranyl, tetrahydrofuryl, tetrahydropyranyl, dithiolidinyl, trialkoxysilyl, trialkylsilyl, cyclobutyl, cyclopentyl, cyclolhexyl, or benzyl, each of which is optionally substituted with C$_{1-8}$alkyl, C$_{1-4}$haloalkyl, F, Cl, Br, I, CN and NO$_2$; and $R^c$ is, independently at each instance, C$_{1-8}$alkyl, C$_{1-4}$haloalkyl, F, Cl, Br, I, CN, NO$_2$, —(=O)$R^b$, —(=O)O$R^a$, —(=O)N$R^a$$R^a$, —C(=N$R^a$)N$R^a$$R^a$, —O$R^a$, —OC$_{2-6}$alkylN$R^a$, —OC(=O)$R^b$, —OC(=O)N$R^a$$R^a$, —OC(=O)N($R^a$)S(=O)$_2$$R^b$, —OC$_{2-6}$alkylN$R^a$$R^a$, —OC$_{2-6}$alkylO$R^a$, —S$R^a$, —S(=O)$R^b$, —S(=O)$_2$$R^b$, —S(=O)$_2$N$R^a$$R^a$, —S(=O)$_2$N($R^a$)C(=O)$R^b$, —S(=O)$_2$N($R^a$)C(=O)O$R^b$, —S(=O)$_2$N($R^a$)C(=O)N$R^a$$R^a$, —N$R^a$$R^a$, —N($R^a$)C(=O)$R^b$, —N($R^a$)C(=O)O$R^b$, —N($R^a$)C(=O)N$R^a$$R^a$, —N($R^a$)C(=N$R^a$)N$R^a$$R^a$, —N($R^a$)S(=O)$_2$$R^b$, —N($R^a$)S(=O)$_2$N$R^a$$R^a$, —N$R^a$C$_{2-6}$alkylN$R^a$$R^a$ or —N$R^a$C$_{2-6}$alkylO$R^a$.

In one embodiment of the invention, $R^1$ is NR$^6$R$^7$.

In another embodiment, in conjunction with any of the above or below embodiments, $R^{21}$ is phenyl substituted by 0, 1, 2, 3 or 4 substituents independently selected from $R^b$ and $R^c$.

In another embodiment, in conjunction with any of the above or below embodiments, $R^{21}$ is pyridine substituted by 0, 1, 2, 3 or 4 substituents independently selected from $R^b$ and $R^c$.

In another embodiment, in conjunction with any of the above or below embodiments, $R^{31}$ is phenyl substituted by 0, 1, 2, 3 or 4 substituents independently selected from $R^b$ and $R^c$.

In another embodiment, in conjunction with any of the above or below embodiments, $R^{31}$ is pyridine substituted by 0, 1, 2, 3 or 4 substituents independently selected from $R^b$ and $R^c$.

In another embodiment, in conjunction with any of the above or below embodiments, $R^{31}$ is phenyl substituted by 0, 1 or 2 substituents independently selected from $R^c$; $R^{32}$ is, independently at each instance, C$_{1-8}$alkyl or C$_{1-8}$alkoxyl; $R^{33}$ is, independently at each instance, —C(=O)—, —(=O)N$R^a$—, —C(=N$R^a$)N$R^a$—, —O—, —OC$_{2-6}$alkylN$R^a$—, —OC$_{2-6}$alkylO—, —S—, —S(=O)—, —S(=O)$_2$—, —S(=O)$_2$N$R^a$—, —S(=O)$_2$N($R^a$)C(=O)—, —N($R^a$)—, —N($R^a$)C(=O)—, —N($R^a$)C(=O)O—, —N($R^a$)C(=O)N($R^a$)—, —N($R^a$)S(=O)$_2$—, —N$R^a$C$_{2-6}$alkylN($R^a$)— or —N$R^a$C$_{2-6}$alkylO—; and $R^{34}$ is, independently at each instance, phenyl, piperizinyl, pyridyl, piperidinyl, morpholinyl, pyrrolidinyl, pyrrolyl, imidazolyl, pyrrolidinonyl or tetrahydrofuryl.

In another embodiment, in conjunction with any of the above or below embodiments, $R^{31}$ is pyridine substituted by 0, 1 or 2 substituents independently selected from $R^c$; $R^{32}$ is, independently at each instance, C$_{1-8}$alkyl or C$_{1-8}$alkoxyl; $R^{33}$ is, independently at each instance, —C(=O)—, —(=O)NR$^a$—, —C(=N$R^a$)N$R^a$—, —O—, —OC$_{2-6}$alkylN$R^a$—, —OC$_{2-6}$alkylO—, —S—, —S(=O)—, —S(=O)$_2$—, —S(=O)$_2$N$R^a$—, —S(=O)$_2$N($R^a$)C(=O)—, —N($R^a$)—, —N($R^a$)C(=O)—, —N($R^a$)C(=O)O—, —N($R^a$)C(=O)N($R^a$)—, —N($R^a$)S(=O)$_2$—, —N$R^a$C$_{2-6}$alkylN($R^a$)— or —N$R^a$C$_{2-6}$alkylO—; and $R^{34}$ is, independently at each instance, phenyl, piperizinyl, pyridyl, piperidinyl, morpholinyl, pyrrolidinyl, pyrrolyl, imidazolyl, pyrrolidinonyl or tetrahydrofuryl.

In another embodiment, in conjunction with any of the above or below embodiments, $R^6$ is —$R^{62}$.

In another embodiment, in conjunction with any of the above or below embodiments, $R^6$ is —$R^{61}$—$R^{62}$.

In another embodiment, in conjunction with any of the above or below embodiments, $R^6$ is —$R^{62}$—$R^{64}$.

In another embodiment, in conjunction with any of the above or below embodiments, $R^6$ is —$R^{61}$—$R^{62}$—$R^{64}$.

In another embodiment, in conjunction with any of the above or below embodiments, $R^2$ is phenyl substituted by 0, 1 or 2 substituents independently selected from $R^b$ and $R^c$.

In another embodiment, in conjunction with any of the above or below embodiments, $R^1$ is NR$^6$R$^7$; $R^6$ is —$R^{62}$; $R^7$ is H; $R^{61}$ is phenyl or piperidinyl; $R^{62}$ is, independently at each instance, C$_{1-8}$alkyl; $R^{63}$ is, independently at each instance, —C(=O)—, —C(=O )N$R^a$—, —O($R^a$)—, —OC$_{2-6}$alkylN$R^a$—, —OC$_{2-6}$alkylO—, —S—, —S(=O)$_2$N$R^a$—, —N($R^a$)—, —N($R^a$)C(=O)—, —N($R^a$)S(=O)$_2$—, —N($R^a$)S(=O)$_2$N($R^a$)—, —N$R^a$C$_{2-6}$alkylN($R^a$)— or —N$R^a$C$_{2-6}$alkylO—; and $R^{64}$ is, independently at each instance, phenyl, piperizinyl, pyridyl, piperidinyl, morpholinyl, pyrrolidinyl, pyrrolyl, imidazolyl, pyrrolidinonyl or tetrahydrofuryl.

In another embodiment, in conjunction with any of the above or below embodiments, $R^1$ is NR$^6$R$^7$; $R^6$ is —$R^{61}$—$R^{62}$; $R^7$ is H; $R^{61}$ is phenyl or piperidinyl; $R^{62}$ is, independently at each instance, C$_{1-8}$alkyl; $R^{63}$ is, independently at each instance, —C(=O)—, —(=O)N$R^a$—, —O($R^a$)—, —OC$_{2-6}$alkylN$R^a$—, —OC$_{2-6}$alkylO—, —S—, —S(=O)$_2$N$R^a$—, —N($R^a$)—, —N($R^a$)C(=O)—, —N($R^a$)S(=O)$_2$—, —N($R^a$)S(=O)$_2$N($R^a$)—, —N$R^a$C$_{2-6}$alkylN($R^a$)— or —N$R^a$C$_{2-6}$alkylO—; and $R^{64}$ is, independently at each instance, phenyl, piperizinyl, pyridyl, piperidinyl, morpholinyl, pyrrolidinyl, pyrrolyl, imidazolyl, pyrrolidinonyl or tetrahydrofuryl.

In another embodiment, in conjunction with any of the above or below embodiments, $R^1$ is $NR^6R^7$; $R^6$ is —$R^{62}$—$R^{64}$; $R^7$ is H; $R^{61}$ is phenyl or piperidinyl; $R^{62}$ is, independently at each instance, $C_{1-8}$alkyl; $R^{63}$ is, independently at each instance, —C(=O)—, —(=O)NR$^a$—, —O(R$^a$)—, —OC$_{2-6}$alkylNR$^a$—, —OC$_{2-6}$alkylO—, —S—, —S(=O)$_2$NR$^a$—, —N(R$^a$)—, —N(R$^a$)C(=O)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—; and $R^{64}$ is, independently at each instance, phenyl, piperizinyl, pyridyl, piperidinyl, morpholinyl, pyrrolidinyl, pyrrolyl, imidazolyl, pyrrolidinonyl or tetrahydrofuryl.

In another embodiment, in conjunction with any of the above or below embodiments, $R^1$ is $NR^6R^7$; $R^6$ is —$R^{61}$—$R^{62}$—$R^{64}$; $R^7$ is H; $R^{61}$ is phenyl or piperidinyl; $R^{62}$ is, independently at each instance, $C_{1-8}$alkyl; $R^{63}$ is, independently at each instance, —C(=O)—, —(=O)NR$^a$—, —O(R$^a$)—, —OC$_{2-6}$alkylNR$^a$—, —OC$_{2-6}$alkylO—, —S—, —S(=O)$_2$NR$^a$—, —N(R$^a$)—, —N(R$^a$)C(=O)—, —N(R$^a$)S(=O)$_2$—, —N(R$^a$)S(=O)$_2$N(R$^a$)—, —NR$^a$ C$_{2-6}$alkylN(R$^a$)— or —NR$^a$C$_{2-6}$alkylO—; and $R^{64}$ is, independently at each instance, phenyl, piperizinyl, pyridyl, piperidinyl, morpholinyl, pyrrolidinyl, pyrrolyl, imidazolyl, pyrrolidinonyl or tetrahydrofuryl.

In another embodiment, in conjunction with any of the above or below embodiments, $R^2$ is phenyl substituted by 0, 1 or 2 substituents independently selected from $R^b$ and $R^c$.

In another embodiment, in conjunction with any of the above or below embodiments, $R^3$ is phenyl substituted by 0, 1 or 2 substituents independently selected from $R^b$ and $R^c$.

In another embodiment, in conjunction with any of the above or below embodiments, $R^4$ is H.

In another embodiment, in conjunction with any of the above or below embodiments, $R^5$ is H.

In another embodiment, in conjunction with any of the above or below embodiments, $R^5$ is CN.

In another embodiment, in conjunction with any of the above or below embodiments, $R^5$ is $C_{1-8}$alkylNH$_2$.

In another embodiment, in conjunction with any of the above or below embodiments, $R^1$ is $NR^6R^7$ and $R^5$ taken together with $R^1$ form a pyrazole ring substituted with 0, 1, 2 or 3 substituents independently selected from $R^b$ or $R^c$.

In another embodiment, in conjunction with any of the above or below embodiments, $R^1$ is $NR^6R^7$ and $R^6$ taken together with $R^7$ form a piperidine ring substituted with 0, 1, 2 or 3 substituents independently selected from $R^b$ or $R^c$.

In another embodiment, in conjunction with any of the above or below embodiments, $R^1$ is $NR^6R^7$ and $R^6$ taken together with $R^7$ form a piperazine ring substituted with 0, 1, 2 or 3 substituents independently selected from $R^b$ or $R^c$.

In another embodiment, in conjunction with any of the above or below embodiments, $R^1$ is selected from tetrahydro-2-furanylmethylamino, 2-(1-piperazinyl)ethylamino, 2-(4-morpholinyl)ethylamino, 4-tert-butylphenylamino, (3-methylphenyl)methylamino, (3-methoxyphenyl)ethylamino, (4-methoxyphenyl)ethylamino, (4-chorophenyl)ethylamino, (2-methoxycyclobutyl)methylamino, isopropylamino, pyrrolidinylethylamino, piperidinylethylamino, (1-phenylmethyl)-4-piperidinylamino, dihydro-indene-1-ylamino, pyridylethylamino, N,N-diethylamino-1-methylbutyl-amino, 2-(N,N-diethylamino)ethyl-1-piperazinyl, dimethylaminobutylamino, 2-(1H-imidazol-1-yl)ethyl-1-piperazinyl, 3-hydroxypropylamino, 3-(1H-imidazol-1-yl)propylamino, 4-ethylcarboxylate-piperidinyl, butanoic acid-4-amino, 2-hydroxy-butanoic acid-4-amino, N-boc-piperazinylethylamino, N-ethyl-piperazinylethylamino, N-(1,2,2,6,6-pentamethyl)-4-piperidine amino, 1-methyl-2-pyrrolidinylmethylamino, 1-ethyl-2-pyrrolidinylmethylamino, cyclopropylmethylamino, phenethylamino, N-(1,3-dithoilan-2-yl)amino, 2-acetamidoethylamino, (methyloxy)methyloxy and 2-(methyloxy)ethylamino.

In another embodiment, in conjunction with any of the above or below embodiments, $R^3$ is selected from 4-((2-(4-morpholinyl)ethyl)oxy)phenyl, 4-(4-(morpholinyl)methyl)phenyl, 4-((2-(1-pyrrolidinyl)ethyl)oxy)phenyl, 4-((2-(1-piperidinyl)ethyl)oxy)phenyl, 3-fluoro-4-((2-(1-piperidinyl)ethyl)oxy)phenyl, 4-((2-(1H-pyrrol-1-yl)ethyl)oxy)phenyl, 4-((2-(N,N-diisopropylethylamino)ethyl)oxy)phenyl, 4-((2-(1H-imidazol-1-yl)ethyl)oxy)phenyl, 4-((2-(1-methyl-3-piperidinyl)methyl)oxy)phenyl, 4-((1-(methyloxy)ethyl)oxy)phenyl, pyridine, 4-((2-(pyrrolidinone)ethyl)oxy)phenyl, 4-((4-morpholinyl)carbonyl)phenyl, 3-((4-morpholinyl)carbonyl)phenyl, 3-((4-methyl-1-piperazinyl)carbonyl)phenyl, 4-((2-(dimethylamino)ethyl)oxy)phenyl, 3-benyloxyphenyl, 4-(4-isopropyl-1-piperazinyl)phenyl, 4-((4-methyl-1-piperazinyl)sulfonyl)phenyl and triethylsilyl.

In another embodiment, there is provided a compound defined by Formula I

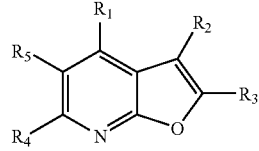

I or a stereoisomer, a tautomer, a solvate a pharmaceutically acceptable salt, a derivative or a prodrug thereof, wherein $R^1$ is selected from tetrahydro-2-furanylmethylamino, 2-(1-piperazinyl)ethylamino, 2-(4-morpholinyl)ethylamino, 4-tert-butylphenylamino, (3-methylphenyl)methylamino, (3-methoxyphenyl)ethylamino, (4-methoxyphenyl)ethylamino, (4-chorophenyl)ethylamino, (2-methoxycyclobutyl)methylamino, isopropylamino, pyrrolidinylethylamino, piperidinylethylamino, (1-phenylmethyl)-4-piperidinylamino, dihydro-indene-1-ylamino, pyridylethylamino, N,N-diethylamino-1-methylbutyl-amino, 2-(N,N-diethylamino)ethyl-1-piperazinyl, dimethylaminobutylamino, 2-(1H-imidazol-1-yl)ethyl-1-piperazinyl, 3-hydroxypropylamino, 3-(1H-imidazol-1-yl)propylamino, 4-ethylcarboxylate-piperidinyl, butanoic acid-4-amino, 2-hydroxy-butanoic acid-4-amino, N-boc-piperazinylethylamino, N-ethyl-piperazinylethylamino, N-(1,2,2,6,6-pentamethyl)-4-piperidine amino, 1-methyl-2-pyrrolidinylmethylamino, 1-ethyl-2-pyrrolidinylmethylamino, cyclopropylmethylamino, phenethylamino, N-(1,3-dithoilan-2-yl)amino, 2-acetamidoethylamino, (methyloxy)methyloxy and 2-(methyloxy)ethylamino.

$R^2$ is phenyl substituted by 0, 1 or 2 substituents independently selected from $R^b$ and $R^c$;

$R^3$ is selected from 4-((2-(4-morpholinyl)ethyl)oxy)phenyl, 4-(4-(morpholinyl)methyl)phenyl, 4-((2-(1-pyrrolidinyl)ethyl)oxy)phenyl, 4-((2-(1-piperidinyl)ethyl)oxy)phenyl, 3-fluoro-4-((2-(1-piperidinyl)ethyl)oxy)phenyl, 4-((2-(1H-pyrrol-1-yl)ethyl)oxy)phenyl, 4-((2-(N,N-diisopropylethylamino)ethyl)oxy)phenyl, 4-((2-(1H-imidazol-1-yl)ethyl)oxy)phenyl, 4-((2-(1-methyl-3-piperidinyl)methyl)oxy)phenyl, 4-((1-(methyloxy)ethyl)oxy)phenyl, pyridine, 4-((2-(pyrrolidinone)ethyl)oxy)phenyl, 4-((4-morpholinyl)carbonyl)phenyl, 3-((4-morpholinyl)carbonyl)phenyl, 3-((4-methyl-1-piperazinyl)

carbonyl)phenyl, 4-((2-(dimethylamino)ethyl)oxy)phenyl, 3-benyloxyphenyl, 4-(4-isopropyl-1-piperazinyl)phenyl, 4-((4-methyl-1-piperazinyl)sulfonyl)phenyl and triethylsilyl;

$R^4$ is H; and
$R^5$ is H, CN or $C_{1-8}$alkyl$NH_2$.

In yet another embodiment, there is provided a compound having the structure

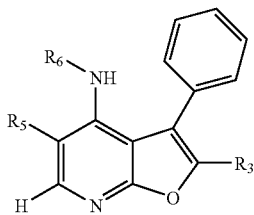

or a stereoisomer, a tautomer, a solvate, a pharmaceutically acceptable salt or derivative, or a prodrug thereof, wherein
$R^3$ is phenyl substituted by 0, 1 or 2 substituents independently selected from $R^b$ and $R^c$;
$R^5$ is H, CN or $C_{1-8}$alkyl$NH_2$; and
$R^6$ is —$R^{62}$, —$R^{61}$—$R^{62}$, —$R^{62}$—$R^{63}$, —$R^{62}$—$R^{64}$ or —$R^{61}$—$R^{62}$—$R^{64}$,
wherein
$R^{61}$ is phenyl or piperidinyl;
$R^{62}$ is, independently at each instance, $C_{1-8}$alkyl;
$R^{63}$ is, independently at each instance, —C(=O)—, —C(=O)NR$^a$—, —O(R$^a$)—, OC$_{2-6}$alkylNR$^a$—, —OC$_{2-6}$alkylO—, —S—, —S(=O)$_2$NR$^a$—, —N(R$^a$)—, —N(R$^a$)C(=O)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—; and
$R^{64}$ is, independently at each instance, phenyl, piperizinyl, pyridyl, piperidinyl, morpholinyl, pyrrolidinyl, pyrrolyl, imidazolyl, pyrrolidinonyl or tetrahydrofuryl.

In yet another embodiment, there are provided the following compounds:
2,3-diphenyl-N-((2S)-tetrahydro-2-furanylmethyl)furo[2,3-b]pyridin-4-amine;
2,3-diphenyl-N-(2-(1-piperazinyl)ethyl)furo[2,3-b]pyridin-4-amine;
2-(4-((2-(4-morpholinyl)ethyl)oxy)phenyl)-3-phenyl-N-(2-(1-piperazinyl)ethyl)furo[2,3-b]pyridin-4-amine;
N-(2-(4-morpholinyl)ethyl)-2-(4-((2-(4-morpholinyl)ethyl)oxy)phenyl)-3-phenylfuro[2,3-b]pyridin-4-amine;
2,3-diphenyl-4-(((2S)-tetrahydro-2-furanylmethyl)amino)furo[2,3-b]pyridine-5-carbonitrile;
3-phenyl-N-(2-(1-piperazinyl)ethyl)-2-(4-((2-(1-pyrrolidinyl)ethyl)oxy)phenyl)furo[2,3-b]pyridin-4-amine;
3-phenyl-N-(2-(1-piperazinyl)ethyl)-2-(4-((2-(1-piperidinyl)ethyl)oxy)phenyl)furo[2,3-b]pyridin-4-amine;
2,3-diphenyl-4-((2-(1-piperazinyl)ethyl)amino)furo[2,3-b]pyridine-5-carbonitrile;
4-chloro-2,3-diphenyl-N-((2S)-tetrahydro-2-furanylmethyl)furo[2,3-b]pyridin-5-amine;
5-(aminomethyl)-2,3-diphenyl-N-(2-(1-piperazinyl)ethyl)furo[2,3-b]pyridin-4-amine;
4-chloro-2,3-diphenyl-N-(2-(1-piperazinyl)ethyl)furo[2,3-b]pyridin-5-amine;
N,N'-bis(4-(1,1-dimethylethyl)phenyl)-2,3-diphenylfuro[2,3-b]pyridine-4,5-diamine;
3-phenyl-N-(2-(1-piperazinyl)ethyl)-2-(4-((2-(1H-pyrrol-1-yl)ethyl)oxy)phenyl)furo[2,3-b]pyridin-4-amine;

2-(4-((2-(bis(1-methylethyl)amino)ethyl)oxy)phenyl)-3-phenyl-N-(2-(1-piperazinyl)ethyl)furo[2,3-b]pyridin-4-amine;
3-(4-((2-(4-morpholinyl)ethyl)oxy)phenyl)-2-phenyl-N-(2-(1-piperazinyl)ethyl)furo[2,3-b]pyridin-4-amine;
2,3-diphenyl-4-((2-(2-pyridinyl)ethyl)amino)furo[2,3-b]pyridine-5-carbonitrile;
2,3-diphenyl-4-((2-(3-pyridinyl)ethyl)amino)furo[2,3-b]pyridine-5-carbonitrile;
4-(((3-methylphenyl)methyl)amino)-2,3-diphenylfuro[2,3-b]pyridine-5-carbonitrile;
4-((1-methylethyl)amino)-2,3-diphenylfuro[2,3-b]pyridine-5-carbonitrile;
2,3-diphenyl-4-((2-(1-pyrrolidinyl)ethyl)amino)furo[2,3-b]pyridine-5-carbonitrile;
2,3-diphenyl-4-((2-(1-piperidinyl)ethyl)amino)furo[2,3-b]pyridine-5-carbonitrile;
2,3-diphenyl-4-((1-(phenylmethyl)-4-piperidinyl)amino)furo[2,3-b]pyridine-5-carbonitrile;
4-((1S)-2,3-dihydro-1H-inden-1-ylamino)-2,3-diphenylfuro[2,3-b]pyridine-5-carbonitrile;
4-((2-((2S)-1-methyl-2-pyrrolidinyl)ethyl)amino)-2,3-diphenylfuro[2,3-b]pyridine-5-carbonitrile;
2,3-diphenyl-4-((2-(4-pyridinyl)ethyl)amino)furo[2,3-b]pyridine-5-carbonitrile;
7,8-diphenyl-1H-furo[2,3-b]pyrazolo[3,4-d]pyridin-3-amine;
4-(((1R)-4-(diethylamino)-1-methylbutyl)amino)-2,3-diphenylfuro[2,3-b]pyridine-5-carbonitrile;
4-(4-(2-(diethylamino)ethyl)-1-piperazinyl)-2,3-diphenylfuro[2,3-b]pyridine-5-carbonitrile;
4-((4-(dimethylamino)butyl)amino)-2,3-diphenylfuro[2,3-b]pyridine-5-carbonitrile;
4-(4-(2-(1H-imidazol-1-yl)ethyl)-1-piperazinyl)-2,3-diphenylfuro[2,3-b]pyridine-5-carbonitrile;
3-phenyl-2-(4-((2-(1-piperidinyl)ethyl)oxy)phenyl)-N-(2-(4-pyridinyl)ethyl)furo[2,3-b]pyridin-4-amine;
2-(4-((2-(1H-imidazol-1-yl)ethyl)oxy)phenyl)-3-phenyl-N-(2-(1-piperazinyl)ethyl)furo[2,3-b]pyridin-4-amine;
4-((3-hydroxypropyl)amino)-2,3-diphenylfuro[2,3-b]pyridine-5-carbonitrile;
4-((2-(1H-imidazol-1-yl)ethyl)amino)-2,3-diphenylfuro[2,3-b]pyridine-5-carbonitrile;
4-amino-2,3-diphenylfuro[2,3-b]pyridine-5-carbonitrile;
N-(3-(1H-imidazol-1-yl)propyl)-3-phenyl-2-(4-((2-(1-piperidinyl)ethyl)oxy)phenyl)furo[2,3-b]pyridin-4-amine;
N-(7,8-diphenyl-1H-furo[2,3-b]pyrazolo[3,4-d]pyridin-3-yl)acetamide;
ethyl 1-(5-cyano-2,3-diphenylfuro[2,3-b]pyridin-4-yl)-4-piperidinecarboxylate;
3-phenyl-2-(4-((2-(1-piperidinyl)ethyl)oxy)phenyl)-N-(2-(3-pyridinyl)ethyl)furo[2,3-b]pyridin-4-amine;
N~1~,N~1~-dimethyl-N~3~-(3-phenyl-2-(4-((2-(1-piperidinyl)ethyl)oxy)phenyl)furo[2,3-b]pyridin-4-yl)-1,3-propanediamine;
2-(4-(((1-methyl-3-piperidinyl)methyl)oxy)phenyl)-3-phenyl-N-(2-(1-piperazinyl)ethyl)furo[2,3-b]pyridin-4-amine;
4-((5-cyano-2,3-diphenylfuro[2,3-b]pyridin-4-yl)amino)butanoic acid;
(2S)-4-((5-cyano-2,3-diphenylfuro[2,3-b]pyridin-4-yl)amino)-2-hydroxybutanoic acid;
1,1-dimethylethyl 4-(2-((5-cyano-3-phenyl-2-(4-((2-(1-pyrrolidinyl)ethyl)oxy)phenyl)furo[2,3-b]pyridin-4-yl)amino)ethyl)-1-piperazinecarboxylate;

3-phenyl-4-((2-(1-piperazinyl)ethyl)amino)-2-(4-((2-(1-pyr-rolidinyl)ethyl)oxy)phenyl)furo[2,3-b]pyridine-5-carbonitrile;
N-(7,8-diphenyl-1H-furo[2,3-b]pyrazolo[3,4-d]pyridin-3-yl)benzamide;
7-methyl-1,2-diphenylfuro[3'',2'':5',6']pyrido[4',3':3,4]pyrazolo[1,5-a]pyrimidin-9(11H)-one;
4-((2-(4-ethyl-1-piperazinyl)ethyl)amino)-2,3-diphenylfuro[2,3-b]pyridine-5-carbonitrile;
2-(4-((2-(methyloxy)ethyl)oxy)phenyl)-3-phenyl-N-(2-(1-piperazinyl)ethyl)furo[2,3-b]pyridin-4-amine;
N-(7,8-diphenyl-1H-furo[2,3-b]pyrazolo[3,4-d]pyridin-3-yl)-N'-ethylurea;
N-(1,1-dimethylethyl)-N'-(7,8-diphenyl-1H-furo[2,3-b]pyrazolo[3,4-d]pyridin-3-yl)urea;
N-(1,2,2,6,6-pentamethyl-4-piperidinyl)-3-phenyl-2-(4-((2-(1-piperidinyl)ethyl)oxy)phenyl)furo[2,3-b]pyridin-4-amine;
N-(2-(1-methyl-2-pyrrolidinyl)ethyl)-3-phenyl-2-(4-((2-(1-piperidinyl)ethyl)oxy)phenyl)furo[2,3-b]pyridin-4-amine;
N-(2,6-dichlorophenyl)-N'-(7,8-diphenyl-1H-furo[2,3-b]pyrazolo[3,4-d]pyridin-3-yl)urea;
3-phenyl-N-(2-(1-piperazinyl)ethyl)-2-(3-pyridinyl)furo[2,3-b]pyridin-4-amine;
1-(2-((4-(3-phenyl-4-(((2S)-tetrahydro-2-furanylmethyl)amino)furo[2,3-b]pyridin-2-yl)phenyl)oxy)ethyl)-2-pyrrolidinone;
2-(4-(4-morpholinylcarbonyl)phenyl)-3-phenyl-N-((2S)-tetrahydro-2-furanylmethyl)furo[2,3-b]pyridin-4-amine;
N-(cyclopropylmethyl)-2-(4-((2-(dimethylamino)ethyl)oxy)phenyl)-3-phenylfuro[2,3-b]pyridin-4-amine;
2-(4-((2-(dimethylamino)ethyl)oxy)phenyl)-N-(2-(4-morpholinyl)ethyl)-3-phenylfuro[2,3-b]pyridin-4-amine;
2-(4-((2-(dimethylamino)ethyl)oxy)phenyl)-3-phenyl-N-(2-phenylethyl)furo[2,3-b]pyridin-4-amine;
2-(4-((2-(dimethylamino)ethyl)oxy)phenyl)-N-(1,3-dithiolan-2-ylmethyl)-3-phenylfuro[2,3-b]pyridin-4-amine;
N-(2-((3-phenyl-2-(4-((2-(1-piperidinyl)ethyl)oxy)phenyl)furo[2,3-b]pyridin-4-yl)amino)ethyl)acetamide;
2-(3-fluoro-4-((2-(1-piperidinyl)ethyl)oxy)phenyl)-3-phenyl-N-(2-(1-piperazinyl)ethyl)furo[2,3-b]pyridin-4-amine;
2-(4-(4-morpholinylmethyl)phenyl)-3-phenyl-N-(2-(1-piperazinyl)ethyl)furo[2,3-b]pyridin-4-amine;
2-(3-((4-methyl-1-piperazinyl)carbonyl)phenyl)-3-phenylfuro[2,3-b]pyridine;
2-(3-((4-methyl-1-piperazinyl)carbonyl)phenyl)-3-phenyl-N-(2-(1-piperazinyl)ethyl)furo[2,3-b]pyridin-4-amine;
2-(3-(4-morpholinylcarbonyl)phenyl)-3-phenyl-N-(2-(1-piperazinyl)ethyl)furo[2,3-b]pyridin-4-amine;
3-phenyl-2-(3-((phenylmethyl)oxy)phenyl)-N-(2-(1-piperazinyl)ethyl)furo[2,3-b]pyridin-4-amine;
2-(3-(4-morpholinylcarbonyl)phenyl)-3-phenylfuro[2,3-b]pyridine;
2-(4-(4-(1-methylethyl)-1-piperazinyl)phenyl)-3-phenyl-N-(2-(1-piperazinyl)ethyl)furo[2,3-b]pyridin-4-amine;
2-(4-((4-methyl-1-piperazinyl)sulfonyl)phenyl)-3-phenyl-N-(2-(1-piperazinyl)ethyl)furo[2,3-b]pyridin-4-amine;
ethyl 2-(4-((2-(dimethylamino)ethyl)oxy)phenyl)-4-hydroxy-3-phenylfuro[2,3-b]pyridine-5-carboxylate;
3-phenyl-N-((2S)-tetrahydro-2-furanylmethyl)-2-(triethylsilyl)furo[2,3-b]pyridin-4-amine;
4-(((methyloxy)methyl)oxy)-3-phenyl-2-(triethylsilyl)furo[2,3-b]pyridine;
ethyl 4-(((methyloxy)methyl)oxy)-3-phenyl-2-(triethylsilyl)furo[2,3-b]pyridine-5-carboxylate;
2-(4-((2-(dimethylamino)ethyl)oxy)phenyl)-3-phenyl-N-(2-(1-piperidinyl)ethyl)furo[2,3-b]pyridin-4-amine;
2-(4-((2-(dimethylamino)ethyl)oxy)phenyl)-N-((1-ethyl-2-pyrrolidinyl)methyl)-3-phenylfuro[2,3-b]pyridin-4-amine;
N-(2-(4-chlorophenyl)ethyl)-2-(4-((2-(dimethylamino)ethyl)oxy)phenyl)-3-phenylfuro[2,3-b]pyridin-4-amine;
2-(4-((2-(dimethylamino)ethyl)oxy)phenyl)-N-(2-(4-(methyloxy)phenyl)ethyl)-3-phenylfuro[2,3-b]pyridin-4-amine;
2-(4-((2-(dimethylamino)ethyl)oxy)phenyl)-N-(2-(2-(methyloxy)phenyl)ethyl)-3-phenylfuro[2,3-b]pyridin-4-amine;
2-(4-((2-(dimethylamino)ethyl)oxy)phenyl)-5-fluoro-N-((2-(methyloxy)cyclobutyl)methyl)-3-phenylfuro[2,3-b]pyridin-4-amine;
2-(4-((2-(dimethylamino)ethyl)oxy)phenyl)-5-fluoro-3-phenyl-N-((2S)-tetrahydro-2-furanylmethyl)furo[2,3-b]pyridin-4-amine;
2-(4-((2-(dimethylamino)ethyl)oxy)phenyl)-5-fluoro-3-phenyl-N-(2-(2-pyridinyl)ethyl)furo[2,3-b]pyridin-4-amine;
2-{4-[2-(dimethylamino)ethoxy]phenyl}-N-[(3-methylthien-2-yl)methyl]-3-phenylfuro[2,3-b]pyridin-4-amine;
(2R)-2-{[(2-{4-[2-(dimethylamino)ethoxy]phenyl}-3-phenylfuro[2,3-b]pyridin-4-yl)amino]methyl}cyclopentanone;
2-{4-[2-(dimethylamino)ethoxy]phenyl}-3-phenyl-N-[(2S)-tetrahydrofuran-2-ylmethyl]furo[2,3-b]pyridin-4-amine;
3-phenyl-2-[4-(2-pyrrolidin-1-ylethoxy)phenyl]-N-[(2S)-tetrahydrofuran-2-ylmethyl]furo[2,3-b]pyridin-4-amine; and
N-(2-(methyloxy)ethyl)-3-phenyl-2-(4-((2-(1-pyrrolidinyl)ethyl)oxy)phenyl)furo[2,3-b]pyridin-4-amine.

The compounds of Formula I, and stereoisomers, solvates, tautomers, pharmaceutically acceptable salts and derivatives, and prodrugs of these compounds are useful for treating mammals with various conditions and/or disease states, as previously described. To this end, and in another embodiment, the invention provides pharmaceutical compositions comprising one or more of the compounds of Formula I, which includes compounds according to any one of the numerous embodiments above, and a pharmaceutically acceptable carrier or diluent.

The compounds of Formula I, or pharmaceutical composition comprising the compound(s), may be administered in an effective amount to the subject to modulate one or more targets in the subject thereby treating the target-mediated disease or condition. Accordingly, another embodiment of the invention relates to a method of treating inflammation in a mammal, the method comprising administering to the mammal a therapeutically effective amount of a compound according to any one of the above embodiments.

Another embodiment of the invention relates to a method of inhibiting T cell activation in a mammal, the method comprising administering to the mammal a therapeutically effective amount of a compound according to any one of the above embodiments.

Another embodiment of the invention relates to a method of treating arthritis, rheumatoid arthritis, psoriatic arthritis, or osteoarthritis in a mammal, the method comprising administering to the mammal a therapeutically effective amount of a compound according to any one of the above embodiments.

Another embodiment of the invention relates to a method of treating organ transplant, acute transplant or heterograft or homograft rejection, or transplantation tolerance induction in a mammal, the method comprising administering to the mammal a therapeutically effective amount of a compound according to any one of the above embodiments.

Another embodiment of the invention relates to a method of treating ischemic or reperfusion injury, myocardial infarction, or stroke in a mammal, the method comprising administering to the mammal a therapeutically effective amount of a compound according to any one of the above embodiments.

Another embodiment of the invention relates to a method of treating multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal, the method comprising administering to the mammal a therapeutically-effective amount of a compound according to any one of the above embodiments.

Another embodiment of the invention relates to a method of treating colon carcinoma or thymoma in a mammal, the method comprising administering to the mammal a therapeutically-effective amount of a compound according to any one of the above embodiments.

Another embodiment of the invention relates to a method of treating a proliferative disease in a mammal, the method comprising administering to the mammal a therapeutically effective amount of a compound according to any one of the above embodiments.

Another embodiment of the invention relates to the method of treating a proliferative disease in a mammal, the method further comprising administering to the mammal a therapeutically effective amount of a second antiproliferative agent with the compound which was administered to the mammal.

In another embodiment, the proliferative disease is cancer.

In another embodiment, the proliferative disease is breast cancer, lung cancer, liver cancer, kidney cancer, ovarian cancer, prostate cancer, psoriasis, prostatic hyperplasia, or a benign tumor.

Another embodiment of the invention relates to a method for treating a tyrosine kinase-mediated disorder in a mammal, comprising administering to the mammal a therapeutically effective amount of a compound according to any one of the above embodiments.

In another embodiment, the tyrosine kinase is Lck or ACK-1.

Various other embodiments of the invention relate to the manufacture of a medicament for the purposes of administering the compound of Formula I, or pharmaceutical composition comprising same, to the mammal for treatment thereof, as described herein.

For example, and in another embodiment, the invention relates to the manufacture of a medicament comprising a compound according to any one of the above embodiments.

Another embodiment of the invention relates to a method of manufacturing a medicament for the treatment of a tyrosine kinase-mediated disease, the method comprising combining a compound according to any one of the above embodiments with a pharmaceutical carrier to form the medicament.

Another embodiment of the invention relates to a method of manufacturing a medicament for the treatment of inflammation, the method comprising combining a compound according to any one of the above embodiments with a pharmaceutical carrier to form the medicament.

Another embodiment of the invention relates to a method of manufacturing a medicament for the inhibition of T cell activation and proliferation, the method comprising combining a compound according to any one of the above embodiments with a pharmaceutical carrier to form the medicament.

Another embodiment of the invention relates to the manufacture of a medicament for the treatment of arthritis, rheumatoid arthritis, psoriatic arthritis, or osteoarthritis in a mammal comprising a therapeutically-effective amount of a compound according to any one of the above embodiments.

Another embodiment of the invention relates to a method of manufacturing a medicament for the treatment of organ transplant, acute transplant or heterograft or homograft rejection, or transplantation tolerance induction in a mammal, the method comprising combining a compound according to any one of the above embodiments with a pharmaceutical carrier to form the medicament.

Another embodiment of the invention relates to a method of manufacturing a medicament for the treatment of ischemic or reperfusion injury, myocardial infarction, or stroke in a mammal, the method comprising combining a compound according to any one of the above embodiments with a pharmaceutical carrier to form the medicament.

Another embodiment of the invention relates to a method of manufacturing a medicament for the treatment of multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal, the method comprising combining a compound according to any one of the above embodiments with a pharmaceutical carrier to form the medicament.

Another embodiment of the invention relates to a method of manufacturing a medicament for the treatment of colon carcinoma or thymoma in a mammal, the method comprising combining a compound according to any one of the above embodiments with a pharmaceutical carrier to form the medicament.

Another embodiment of the invention relates to a method of making a compound as described herein, comprising the steps of:

reacting a compound having the structure

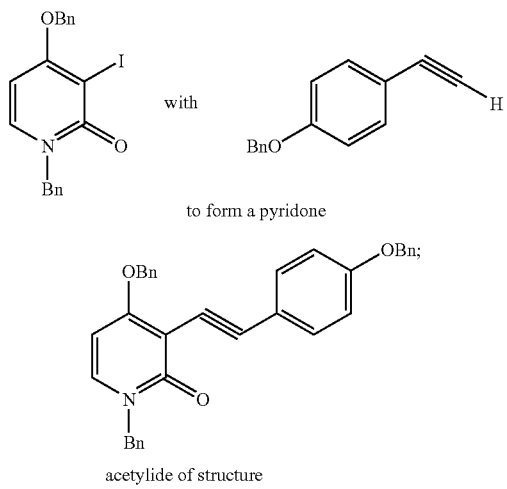

to form a pyridone acetylide of structure

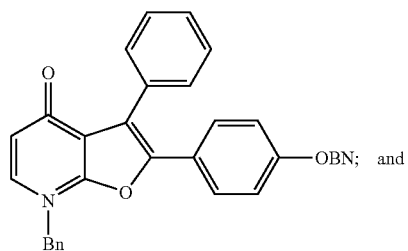

reacting the pyridone acetylide with Ph-I to form a furanopyridone of structure

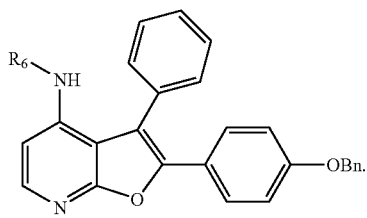

reacting the furanopyridone with a chloride source followed by a primary amine having the structure $R^6NH_2$ in the presence of an base to form a compound of structure:

Unless otherwise specified, the following terms found in the specification and claims have the following meanings and/or definitions:

ACK1: Activated p21lcdc42Hs associated kinase
aq: Aqueous
ATP: Adenosine triphosphate
BSA: Bovine Serum Albumin
DBU: 1,8-diazabicyclo[5.4.0]undec-7-ene
DCE: Dichloroethane
DCM: Dichloromethane
DIEA: Diisopropylethylamine
DMA: N,N-Dimethylacetamide
DMEM: Dulbecco modified Eagle medium
DMF: N,N-Dimethylformamide
DMSO: Dimethylsulfoxide
dppf: 1,1'(diphenylphosphino)ferrocene
DTT: Dithiothreitol
EDTA: Ethylene diamine tetraacetic acid
EtOAc: Ethyl acetate
EtOH: Ethanol
FCS: Fetal Calf Serum
g: Gram(s)
h: Hour(s)
HBTU: O-Benzotriazol-1-yl-N,N,N',N'-tetramethyluronium hexafluorophosphate
Hepes: N-[2-Hydroxyethyl]piperazine-N'-[2-ethanesulfonic acid]
$IC_{50}$ value: The concentration of an inhibitor that causes a 50% reduction in a measured activity.
LiHMDS: Lithium bis(trimethylsilyl)amide
MeI: Methyl iodide
MeCN: Acetonitrile
MeOH: Methanol
min: Minute(s)
mmol: Millimole(s)
Ni-NTA: Nickel-nitriloacetic acid
NIS: N-Iodosuccinimide
NMP: N-methylpyrrolidone
rt: Room temperature
TFA: Trifluoroacetic acid
THF: Tetrahydrofuran Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the invention. Procedures for inserting such labels into the compounds of the invention will be readily apparent to those skilled in the art based on the disclosure herein.

In general, "substituted" as used herein refers to a group as defined below in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfoxide groups, sulfone groups, and sulfonyl groups such as sulfonyl halides and sulfonomides; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carbonyl, carboxyl, and ester groups; and nitrogen in groups such as imines, oximes, hydrazones, and nitriles.

Substituents, including alkyl and ring groups, may be either monovalent or polyvalent depending on the context of their usage. For example, if description contained the group $R^{21}$—$R^{22}$—$R^{24}$ and $R^{22}$ was defined as $C_{1-6}$alkyl, then the $R^{22}$ alkyl would be considered polyvalent because it must be bonded to at least $R^{21}$ and $R^{24}$. Alternatively, if $R^{21}$ was defined as $C_{1-6}$alkyl, then the $R^{21}$ alkyl would be monovalent (excepting any further substitution language).

In general, "alkyl" as used herein either alone or within other terms such as "haloalkyl" and "alkylamino", refers to linear or branched radicals having one to about twelve carbon atoms. Examples of such radicals include methyl, ethyl, n-propyl, isopropyl, n-butyl, isobutyl, sec-butyl, tert-butyl, pentyl, isoamyl, hexyl and the like.

In general, "$C_{\alpha-\beta}$alkyl" as used herein refers to an alkyl group comprising from α to β carbon atoms in a branched, cyclical or linear relationship or any combination of the three. The alkyl groups described in this section may also contain double or triple bonds. Examples of $C_{1-8}$alkyl include, but are not limited to the following:

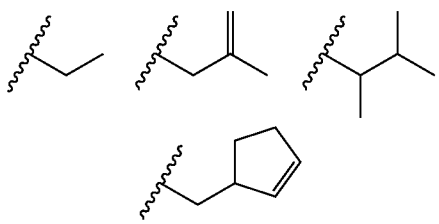

In general, "Halogen" and "halo" as used herein, refers to a halogen atoms selected from F, Cl, Br and I.

In general, "haloalkyl", as used herein refers to radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

In general, "$C_{\alpha-\beta}$haloalkyl" as used herein refers to an alkyl group, as described above, wherein any number—at least one—of the hydrogen atoms attached to the alkyl chain are replaced by F, Cl, Br or I. Examples of haloalkyl includes, without limitation, trifluoromethyl, pentafluoroethyl and the like.

In general, "hydroxyalkyl" as used herein refers to linear or branched alkyl radicals having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

In general, "alkoxy" as used herein refers to linear or branched oxy-containing radicals each having alkyl portions of one to about ten carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of lower haloalkoxy radicals having one to three carbon atoms include fluoromethoxy, chloromethoxy, trifluoromethoxy, trifluoroethoxy, fluoroethoxy and fluoropropoxy.

In general, "sulfonyl", as used herein whether alone or linked to other terms such as alkylsulfonyl, refers respectively to divalent radicals —$SO_2$—.

In general, "aryl", as used herein alone or in combination, refers to a carbocyclic aromatic system containing one or two rings wherein such rings may be attached together in a fused manner. The term "aryl" includes, without limitation, aromatic radicals such as phenyl, naphthyl, indenyl, tetrahydronaphthyl, and indanyl. The "aryl" group may have 1 to 3 substituents such as alkyl, hydroxyl, halo, haloalkyl, nitro, cyano, alkoxy and alkylamino. "Aryl" also includes the moiety wherein the carbocycle is fused with a $C_{3-6}$cycloalkyl bridge, wherein the bridge optionally includes 1, 2 or 3 heteroatoms selected from N, O and S. For example, phenyl substituted with —O—$CH_2$—O— forms the aryl benzodioxolyl substituent.

In general, "heterocyclyl" as used herein, refers to saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, oxo, alkoxy, amino and alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Further examples of suitable heterocycles, some of which have been described above, include, without limitation, the following:

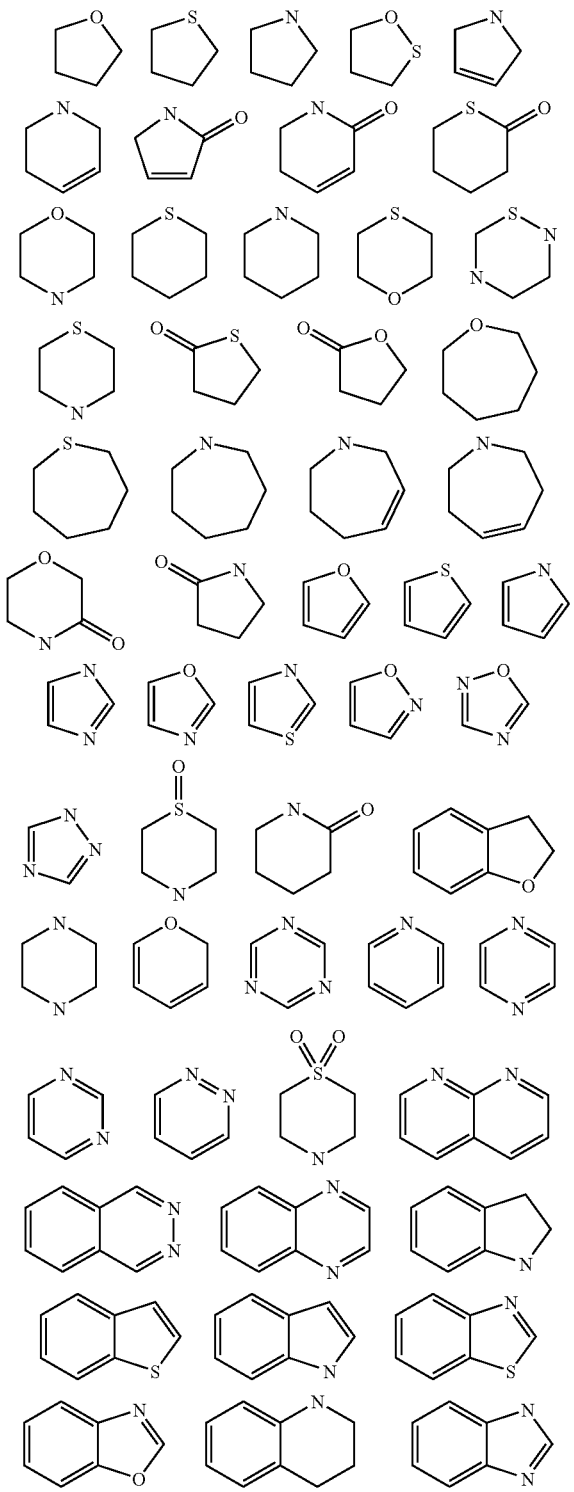

-continued

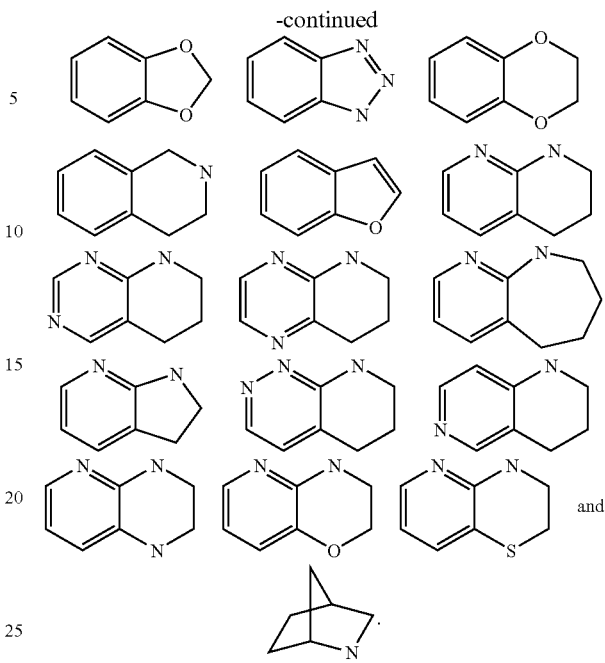

and

"Saturated or unsaturated" means a substitutent that is completely saturated, completely unsaturated, or has any degree of unsaturation in between. Examples of a saturated or unsaturated 6-membered ring carbocycle would include phenyl, cyclohexyl, cyclohexenyl and cyclohexadienyl.

In general, "salt" refers to a salt form of a free base compound of the present invention, as appreciated by persons of ordinary skill in the art. Salts may be prepared by conventional means, known to those skilled in the art. In general, "pharmaceutically-acceptable", when used in reference to a salt, refers to salt forms of a given compound, which are within governmental regulatory safety guidelines for ingestion and/or administration to a subject. The term "pharmaceutically-acceptable salts" embraces salts commonly used to form alkali metal salts and to form addition salts of free acids or free bases. The nature of the salt is not critical, provided that it is pharmaceutically-acceptable.

Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formula I include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid, fumaric, pamoic, citric acid and the like. Other examples include salts with alkali metals or alkaline earth metals, such as sodium, potassium, calcium or magnesium or with organic bases. Preferred salts include hydrochloride, phosphate and edisylate. Additional examples of such salts can be found in Berge et al., J. Pharm. Sci., 66, 1 (1977).

In general, "Derivative" as used herein, refers to simple modifications, readily apparent to those of ordinary skill in the art, on the parent core structure of Formula I, which does not significantly affect (generally decrease) the activity of the compound in-vitro as well as in vivo, in a subject. The term, "derivative" as used herein, is contemplated to include pharmaceutically acceptable derivatives of compounds of Formula I.

In general, "Pharmaceutically acceptable" when used with reference to a derivative, is consistent in meaning with reference to a salt, and refers to a derivative that is pharmacologically safe for consumption, generally as determined by a governmental or authorized regulatory body.

In general, "Leaving group" as used herein, refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

In general, "Protecting group" as used herein, refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups, including aralkyl groups for example, are also suitable for protecting carboxy, hydroxy and mercapto groups. Alkyl groups are also suitable groups for protecting hydroxy and mercapto groups, such as tert-butyl.

Silyl protecting groups are groups containing silicon atoms, which are optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

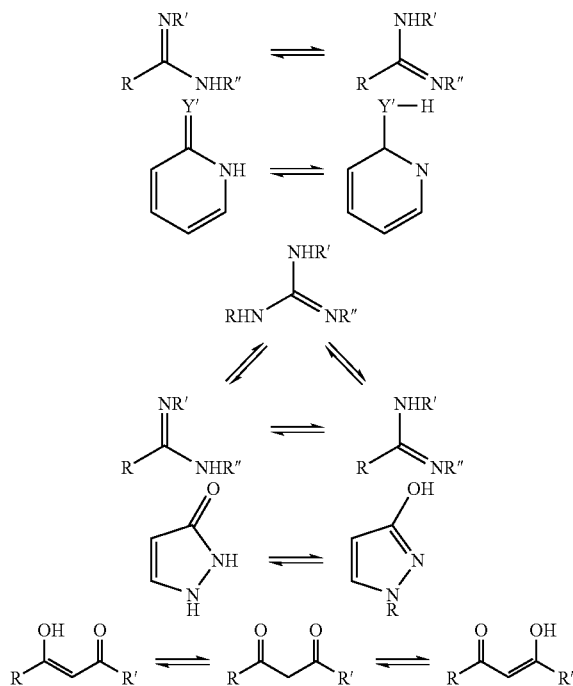

and though one form is named, described, displayed and/or claimed herein, all the tautomeric forms are intended to be inherently included in such name, description, display and/or claim.

Prodrugs of the compounds of this invention are also contemplated by this invention. A "prodrug" is a compound, which when administered to the body of a subject (such as a mammal), breaks down in the subject's metabolic pathway to provide an active compound of Formula I. More specifically, a prodrug is an active or inactive compound that is modified chemically through in vivo physiological action, such as hydrolysis, metabolism and the like, into a compound of this invention following administration of the prodrug to a subject or patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

In general, "stereoisomer" as used herein refers to a compound having one or more asymmetric centers. Chiral centers in a compound generally cause that compound to exist in many different conformations or stereoisomers. The term "stereoisomers" includes enantiomers, diastereomers, atropisomers and geometric isomers. Stereoisomers generally possess different chemical properties and/or biological activity, as appreciated by those skilled in the art. For example, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the present invention necessarily include mixtures of stereoisomers, including racemic mixtures, individual stereoisomers, and optically active forms.

In general, "solvate" when used with reference to a compound refers to a compound which is associated with one or more molecules of a solvent, such as an organic solvent, inorganic solvent, aqueous solvent or mixtures thereof. The compounds of Formula I may also be solvated, especially hydrated. Hydration may occur during manufacturing of the compounds or compositions comprising the compounds, or the hydration may occur over time due to the hygroscopic nature of the compounds. Compounds of the invention may exist as organic solvates as well, including DMF, ether, and alcohol solvates among others. The identification and preparation of any particular solvate is within the skill of the ordinary artisan of synthetic organic or medicinal chemistry.

In general, "Cytokine" as used herein, refers to a secreted protein that affects the functions of other cells, particularly as it relates to the modulation of interactions between cells of the immune system or cells involved in the inflammatory response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

In general, "treatment" as used herein, includes therapeutic treatment as well as prophylactic treatment (either preventing the onset of disorders altogether or delaying the onset of a pre-clinically evident stage of disorders in individuals).

In general, "therapeutically-effective" as used herein, is intended to qualify the amount of each agent, which will achieve the goal of treatment, for example, improvement in disorder severity and the frequency of incidence over treatment of each agent by itself, while avoiding adverse side effects typically associated with alternative therapies.

In general, "Lck- or ACK-1-mediated disease or disease state" refers to all disease states wherein Lck and/or ACK-1 plays a role, either directly as Lck and/or ACK-1 itself, or by Lck and/or ACK-1 inducing another cytokine or disease-causing agent to be released.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

Synthesis

Compounds of Formula I can be synthesized according to one or more of the following schematic procedures and specific methods wherein the substituents are as defined for Formula I, above, except where further noted. The procedures and methods as shown relate to preparation of compounds having unspecified stereochemistry. However, such procedures and methods are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods.

Scheme 1: General Method for Synthesis of Furano-pyridinones

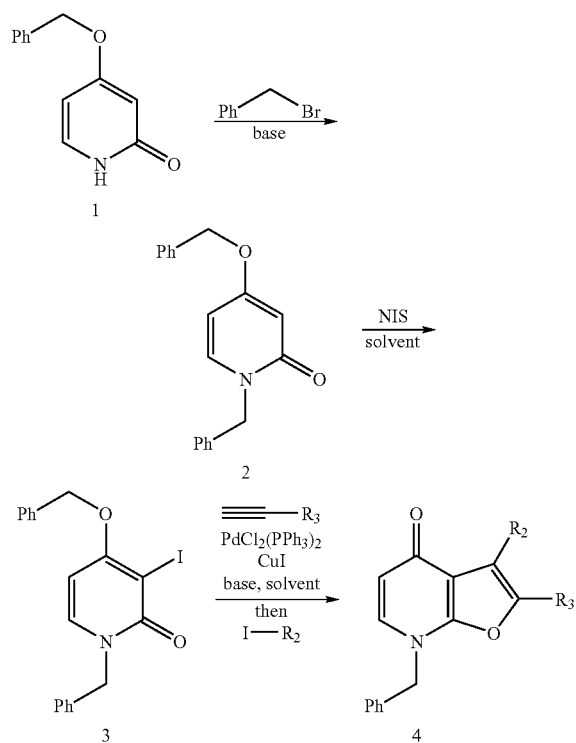

Scheme 1 describes a general method or preparing R² and R³ substituted furano-pyridones which can be converted into the corresponding furano-pyridines. A benzyloxy-substituted pyridone 1 can be protected with an easily removable benzyl group under basic conditions to afford 2. Compound 2 can then be iodinated using a suitable source of iodine, such as N-iodo-succinimide under mild conditions. The iodinated adduct 3 can then be acetylated via a copper acetylide intermediate in the presence of a suitable palladium catalyst, such as dichloro-diphenylphosphine palladium, in one step in suitable solvent and base to install desirable R³ groups on the furan ring. The reaction can then be quenched with a desirable iodide-R² to afford compound 4. In this fashion desired R² and R³ groups can be built into the scaffold simultaneously.

The specific methods below exemplify the synthesis of one possible compound 4 (designated as 4a) which can be made by this route.

Specific Methods for Scheme 1

1-Benzyl-4-benzyloxy-2-pyridone (2)

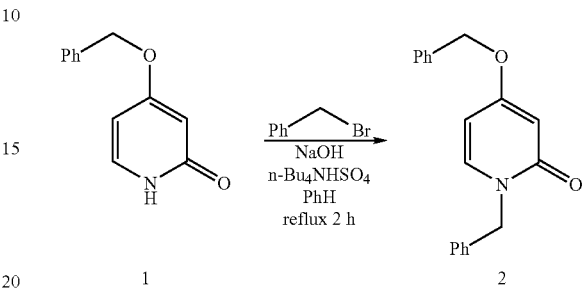

In following a method similar to that described in Katigiri, N; Sato, M.; Yoneda, N.; Saikawa, S.; Sakamoto, T.; Muto, M.; Kaneko, C. J. Chem. Soc. Perkin Trans. 1, 1289-1296, 1986, a solution of 4-benzyloxy-2-pyridone 1 (1.00 g, 5.00 mmol), benzylbromide (4.28 g, 2.97 mL, 25.0 mmol), finely powdered sodium hydroxide (1.00 g, 25.0 mmol), and tetrabutylammonium hydrogen sulfate (0.679 g, 2.00 mmol) in benzene (180 mL) was heated at reflux for 2 h and then cooled to room temperature. The reaction mixture was concentrated and the residue was partitioned between dichloromethane and water. The aqueous phase was separated and extracted with dichloromethane. The combined organic phases were washed with water and saturated aqueous sodium chloride solution, dried over anhydrous sodium sulfate, filtered, and concentrated to afford a brown solid. This solid was recrystallized from ethyl acetate to afford 1-benzyl-4-benzyloxy-2-pyridone 2 as a tan solid. MS (MH⁺) 292.2; Calculated 291 for $C_{19}H_{17}NO_2$.

1-Benzyl-4-benzyloxy-3-iodo-2-pyridone (3)

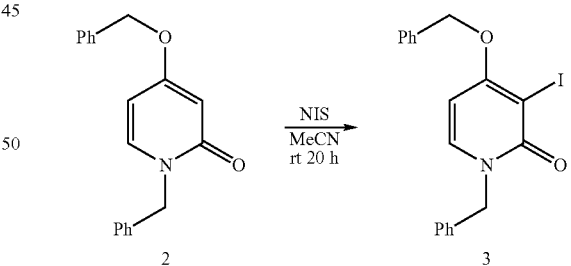

In accordance with a method similar to that described in Bossharth, E.; Desbordes, P; Monteiro, N.; Balme, G. Org. Lett., 5, 2441-2444, 2003, N-Iodosuccinimide (1.390 g, 6.18 mmol) was added to a solution of 1-benzyl-4-benzyloxy-2-pyridone 2 (1.00 g, 3.43 mmol) in acetonitrile (69 mL). The mixture was covered with aluminum foil and stirred at room temperature for 20 h. The reaction mixture was concentrated to afford a crude orange oil. This oil was purified via column chromatography on silica gel (gradient elution with 0-50% ethyl acetate/hexane) to afford an orange solid. Trituration with 50% ethyl acetate/hexane afforded 1-benzyl-4-benzyloxy-3-iodo-2-pyridone 3 as an off-white solid. MS (MH⁺) 418.0; Calculated 417 for $C_{19}H_{16}INO_2$.

7-Benzyl-2-(4-benzyloxy-phenyl)-3-phenyl-7H-furo[2,3-b]pyridin-4-one (4a)

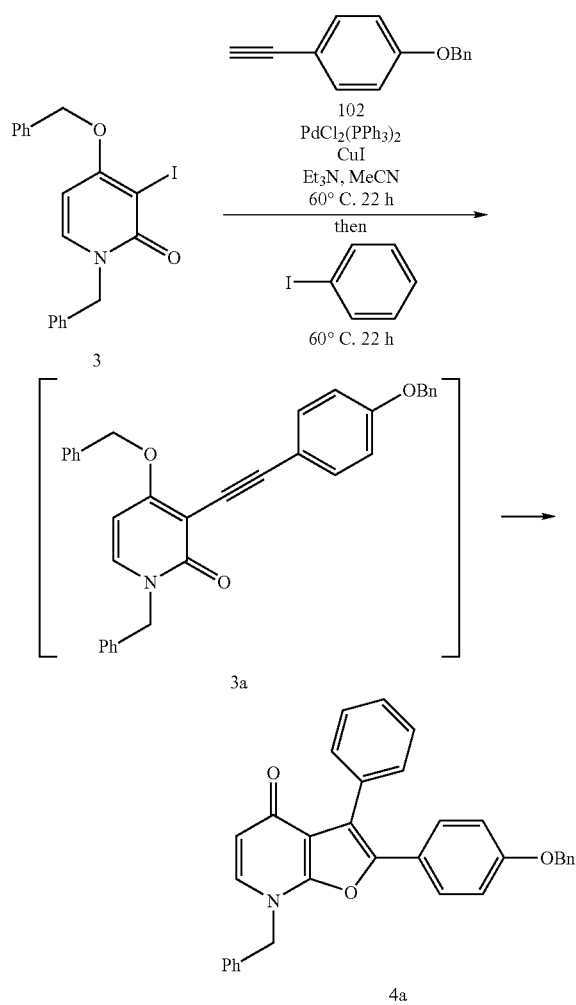

4a

In accordance with a method similar to that described in Bossharth, E.; Desbordes, P; Monteiro, N.; Balme, G. Org. Lett., 5, 2441-2444, 2003, A 150-mL resealable tube was charged with 1-benzyl-4-benzyloxy-3-iodo-2-pyridone 3 (4.500 g, 10.78 mmol), acetonitrile (75 mL), and triethylamine (9 mL). Dichlorobis(triphenylphosphine)palladium (II) (0.378 g, 0.539 mmol), copper (I) iodide (0.103 g, 0.539 mmol), and 4-benzyloxy-phenylacetylene 102 (2.899 g, 13.92 mmol) were added. The system was purged with argon, the tube was sealed, and the mixture stirred at 60° C. for 22 h. An aliquot was removed to confirm the presence of the 3-alkynylpyridone 3a by LC/MS. MS (MH⁺) 498.2; Calculated 497 for $C_{34}H_{27}NO_3$.

Iodobenzene (3.299 g, 1.81 mL, 16.17 mmol) was added and the system was again purged with argon and sealed. The mixture stirred at 60° C. for 22 h to afford a yellow suspension. The mixture was filtered, and the filter cake was washed with acetonitrile and filtered to afford 7-benzyl-2-(4-benzy-loxy-phenyl)-3-phenyl-7H-furo[2,3-b]pyridin-4-one 4a as an off-white solid. MS (MH⁺) 484.1; Calculated 483 for $C_{33}H_{25}NO_3$.

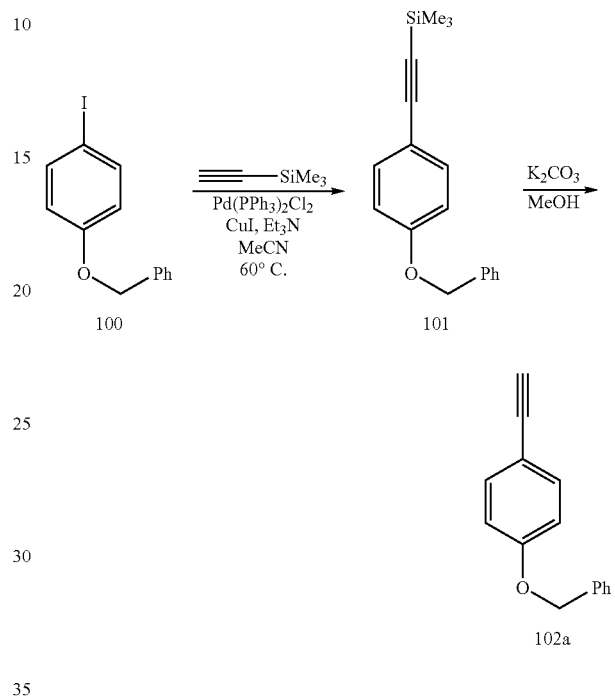

1-Benzyloxy-4-ethynyl-benzene (102a)

A resealable tube was charged with 1-benzyloxy-4-iodo-benzene 100 (5.00 g, 16.1 mmol), acetonitrile (80 mL), and triethylamine (10 mL). Dichlorobis(triphenylphosphine)palladium (II) (0.733 g, 1.05 mmol), copper (I) iodide (0.200 g, 1.05 mmol), and (trimethylsilyl)acetylene (2.06 g, 2.96 mL, 20.9 mmol) were added. The system was purged with argon, the tube was sealed, and the mixture stirred at 60° C. for 17 h. The reaction mixture was filtered twice through a pad of Celite along with ethyl acetate. The filtrate was concentrated to afford (4-benzyloxy-phenylethynyl)trimethylsilane (101) as an orange brown solid which was used without purification.

Potassium carbonate (11.1 g, 80.5 mmol) was added to a solution of the (4-benzyloxy-phenylethynyl)trimethylsilane 101 (13, from above) in methanol (70 mL). The mixture stirred at room temperature for 16 h and was partitioned between ethyl acetate and water. The aqueous phase was separated and extracted with ethyl acetate. The combined organic phases were washed with saturated aqueous sodium chloride solution, dried over anhydrous sodium sulfate, filtered and concentrated to afford a dark brown solid. This material was purified via column chromatography (eluting with 0-5% ethyl acetate-hexane) to afford 1-benzyloxy-4-ethynyl-benzene 102a as an off-white solid.

Scheme 3: General Method for Synthesis of
4-Amino-{2-[2-phenyl)-3-phenyl-substituted furano[2,3-b]pyridines

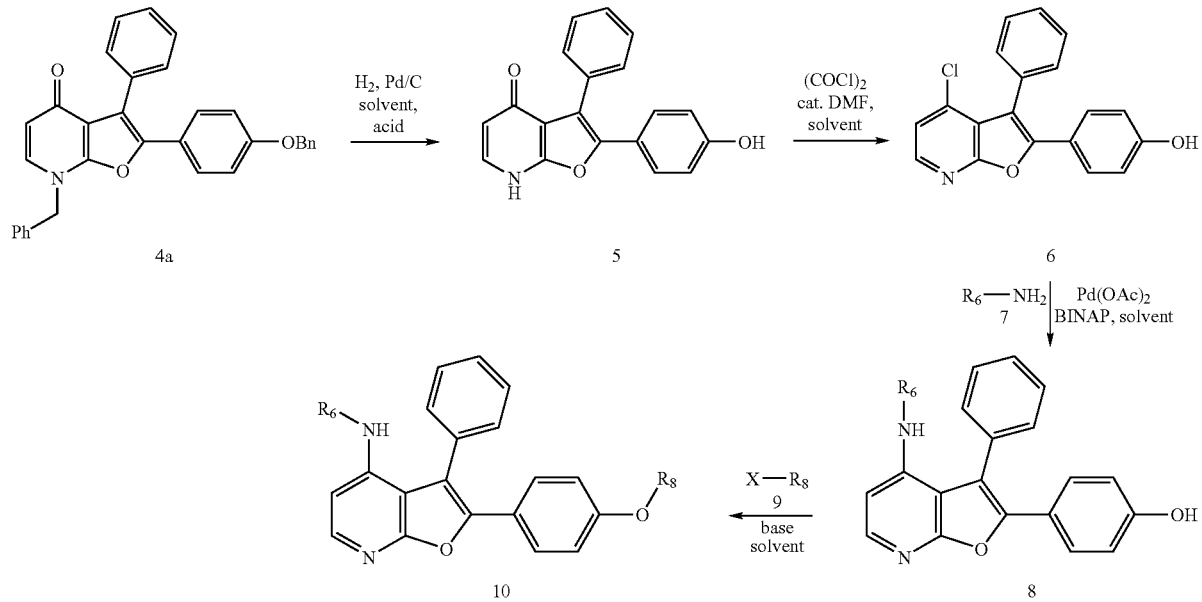

4-Amino-{2-[2-phenyl)-3-phenyl-substituted furano[2,3-b]pyridines 10 can be prepared deprotecting the hydroxyl of compound 4a (prepared in the scheme 1), converting the carbonyl on the pyridine ring of adduct 5 to the corresponding leaving group (also referred to herein as "LG"), such as chloride 6 with a suitable chloride source such as oxalyl chloride in DMF. The LG can then be displaced (using palladium chemistry with a chloride) with a suitable nucleophile, such as an $NH_2R^6$ (as shown in 7), an $NHR^6R^7$, an $OR^6$ or $SR^6$ (not shown) to provide the desired $R^6$ and $R^7$ substitutions in place, as shown on compound 8. The phenyl hydroxyl can then be functionalized with the desired substitution via reaction with a compound $R^8$-LG as shown in 9 in the presence of a base, such as cesium chloride to afford compound 10. The specific methods below exemplify the synthesis of possible compounds 10 (designated as 10a and 10b) which can be made by this route.

Specific Methods for Scheme 3

2-(4-Hydroxy-phenyl)-3-phenyl-7H-furo[2,3-b]pyridin-4-one (5)

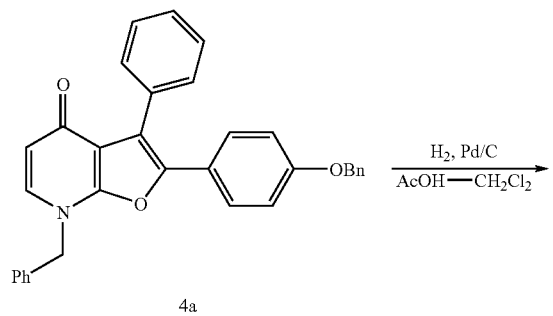

-continued

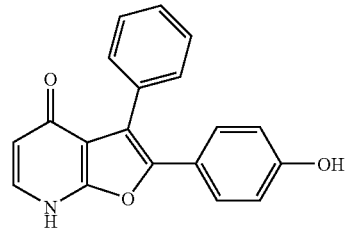

5

A 500-mL round bottom flask equipped with a rubber septum and hydrogen (g) balloon was charged with 7-benzyl-2-(4-benzyloxy-phenyl)-3-phenyl-7H-furo[2,3-b]pyridin-4-one (4a) (1.20 g, 2.50 mmol), dichloromethane (100 mL), acetic acid (100 mL), and ethyl acetate (20 mL). Palladium on carbon (10 wt %, 0.200 g) was added, and the system was evacuated and purged with hydrogen three times. The mixture stirred at room temperature for 24 h and was filtered through Celite. The filtrate was concentrated and the residue was partitioned between ethyl acetate and saturated aqueous sodium bicarbonate. The aqueous phase was separated and extracted with ethyl acetate. The combined organic phases were washed with saturated aqueous sodium chloride, dried over anhydrous sodium sulfate, filtered and concentrated to afford 2-(4-hydroxy-phenyl)-3-phenyl-7H-furo[2,3-b]pyridin-4-one 5 as an off-white solid. MS (MH$^+$) 304.1; Calculated 303 for $C_{19}H_{13}NO_3$.

4-(4-Chloro-3-phenyl-furo[2,3-b]pyridin-2-yl)-phenol (6)

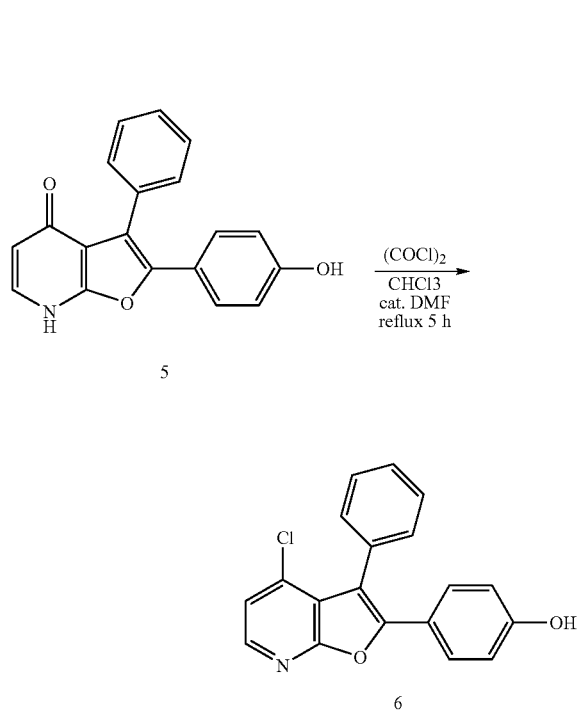

A 25-ml round bottom flask equipped with a reflux condenser fitted with a nitrogen inlet adapter was charged with 2-(4-hydroxy-phenyl)-3-phenyl-7H-furo[2,3-b]pyridin-4-one (5) (0.280 g, 0.923 mmol) and chloroform (9.0 mL). Oxalyl chloride (0.469 g, 0.32 mL, 3.69 mmol) and DMF (0.05 mL) were added and the mixture stirred at room temperature until the evolution of gas ceased (approx. 1 min). The mixture was heated at reflux for 5 h. The reaction mixture was concentrated to afford an orange brown solid which was purified via column chromatography on silica gel (eluting with 0-25% ethyl acetate-hexane) to afford 4-(4-chloro-3-phenyl-furo[2,3-b]pyridin-2-yl)-phenol 6 as an orange solid. MS (MH$^+$) 322.0; Calculated 321 for $C_{19}H_{12}ClNO_2$.

4-{2-[2-(4-Hydroxy-phenyl)-3-phenyl-furo[2,3-b]pyridin-4-ylamino]-ethyl}-piperazine-1-carboxylic acid tert-butyl ester (7a)

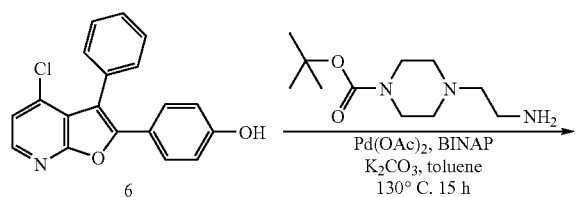

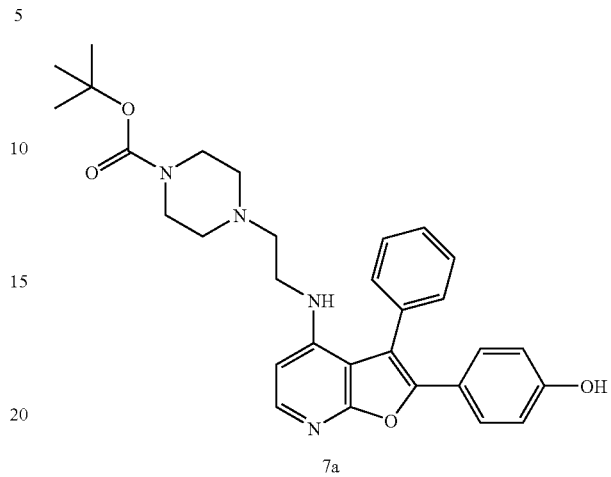

A vial was charged with palladium (II) acetate (0.012 g, 0.054 mmol) and 2,2'-bis(diphenylphosphino)-1,1'-binaphthyl (0.034 g, 0.054 mmol). Toluene (1.0 mL) was added and the system was flushed with argon. The vial was capped and the mixture stirred at room temperature for 15 min.

A resealable tube was charged with 4-(4-chloro-3-phenyl-furo[2,3-b]pyridin-2-yl)-phenol (6) (0.174 g, 0.541 mmol), 4-N-(tert-butoxycarbonyl)-1-aminoethylpiperazine (0.248 g, 1.08 mmol), and potassium carbonate (1.495 g, 10.82 mmol). The Pd/BINAP solution was added along with 1.0 mL of toluene, and the system was flushed with argon. The tube was sealed and the mixture stirred at 130° C. for 15 h. The reaction mixture was partitioned between ethyl acetate and saturated aqueous sodium bicarbonate solution. The aqueous phase was separated and extracted with ethyl acetate. The combined organic phases were washed with saturated aqueous sodium chloride solution, dried over anhydrous sodium sulfate, filtered and concentrated to afford a brown solid. This material was purified via column chromatography on silica gel (eluting with 0-50% (90:10:1, dichloromethane/methanol/ammonium hydroxide)-dichloromethane) to afford 4-{2-[2-(4-hydroxy-phenyl)-3-phenyl-furo[2,3-b]pyridin-4-ylamino]-ethyl}-piperazine-1-carboxylic acid tert-butyl ester 7a as a tan solid. MS (MH$^+$) 515.2; Calculated 514 for $C_{30}H_{34}N_4O_4$.

4-(2-{2-[4-(2-Diisopropylamino-ethoxy)-phenyl]-3-phenyl-furo[2,3-b]pyridin-4-ylamino}-ethyl)-piperazine-1-carboxylic acid tert-butyl ester (10a)

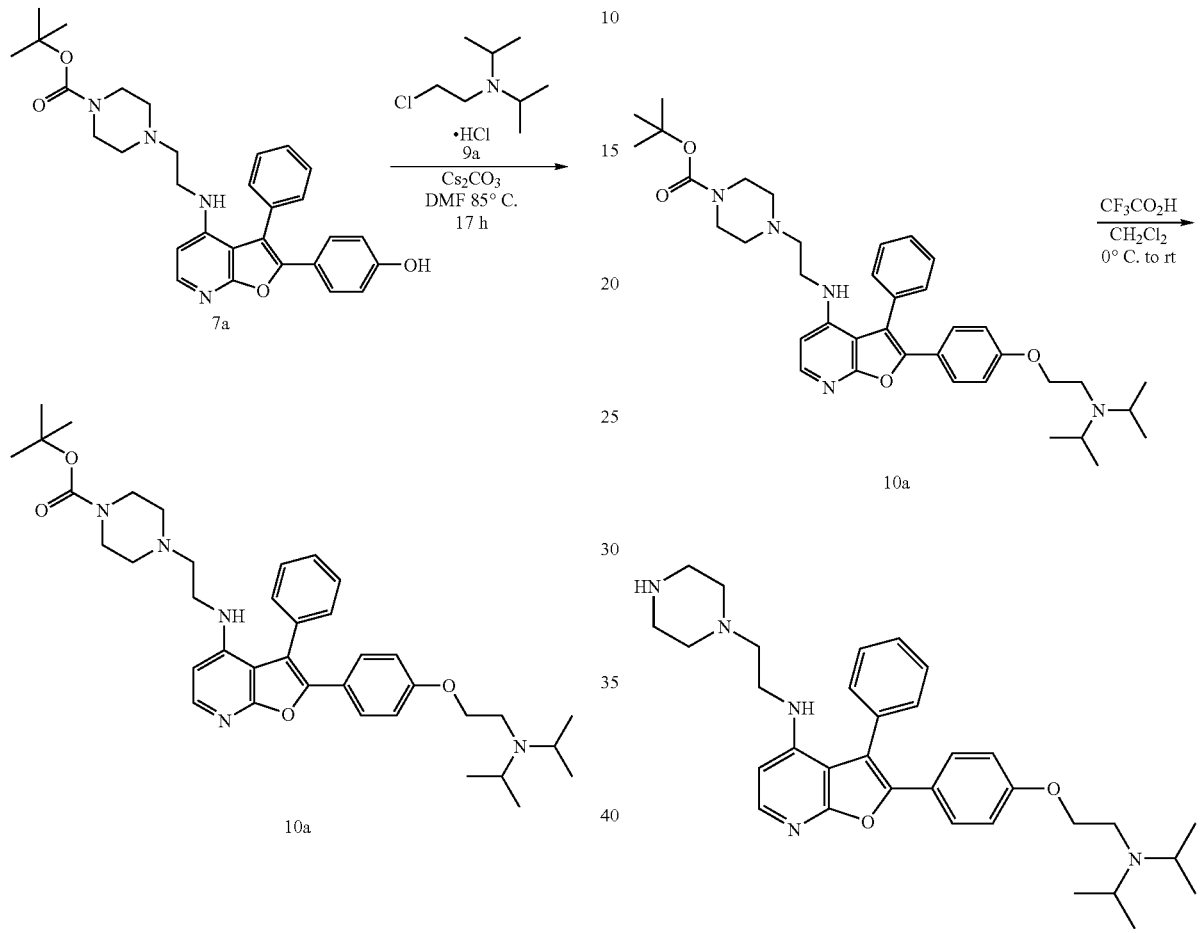

{2-[4-(2-Diisopropylamino-ethoxy)-phenyl]-3-phenyl-furo[2,3-b]pyridin-4-yl}-(2-piperazin-1-yl-ethyl)-amine (10b)

A resealable tube was charged with 4-{2-[2-(4-hydroxy-phenyl)-3-phenyl-furo[2,3-b]pyridin-4-ylamino]-ethyl}-piperazine-1-carboxylic acid tert-butyl ester 8a (0.070 g, 0.136 mmol), 2-diisopropylaminoethylchloride hydrochloride 9a (0.029 g, 0.143 mmol), cesium carbonate (0.222 g, 0.680 mmol), and DMF (2.0 mL). The system was purged with argon and the tube was sealed. The mixture stirred at 85° C. for 17 h. The reaction mixture was then partitioned between ethyl acetate and water. The aqueous phase was separated and extracted with ethyl acetate. The combined organic phases were washed with saturated aqueous sodium chloride solution, dried over anhydrous sodium sulfate, filtered, and concentrated to afford a green oil. This oil was purified via preparative thin layer chromatography (eluting with 95:5:0.5, dichloromethane/methanol, ammonium hydroxide) to afford 4-(2-{2-[4-(2-diisopropylamino-ethoxy)-phenyl]-3-phenyl-furo[2,3-b]pyridin-4-ylamino}-ethyl)-piperazine-1-carboxylic acid tert-butyl ester 10a as a yellow oil. MS (MH$^+$) 642.4; Calculated 641 for $C_{38}H_{51}N_5O_4$.

A solution of 4-(2-{2-[4-(2-diisopropylamino-ethoxy)-phenyl]-3-phenyl-furo[2,3-b]pyridin-4-ylamino}-ethyl)-piperazine-1-carboxylic acid tert-butyl ester 10a (0.075 g, 0.117 mmol) in dichloromethane (2.0 mL) was cooled to 0° C. Trifluoroacetic acid (1.0 mL) was added and the solution stirred under a nitrogen atmosphere at 0° C. and was allowed to warm to room temperature over 2 h. The reaction mixture was concentrated and the residue was partitioned between dichloromethane and saturated aqueous sodium bicarbonate solution. The organic phase was separated and washed with saturated aqueous sodium chloride solution, dried over anhydrous sodium sulfate, filtered and concentrated to afford {2-[4-(2-diisopropylamino-ethoxy)-phenyl]-3-phenyl-furo[2,3-b]pyridin-4-yl}-(2-piperazin-1-yl-ethyl)-amine 10b as an off-white solid. MS (MH$^+$) 542.3; Calculated 541 for $C_{33}H_{43}N_5O_2$.

Scheme 4: Second Specific Method for Synthesis of
4-Amino-(2-(2-phenyl-substituted )-3-phenyl-substituted) furano[2,3-b]pyridines

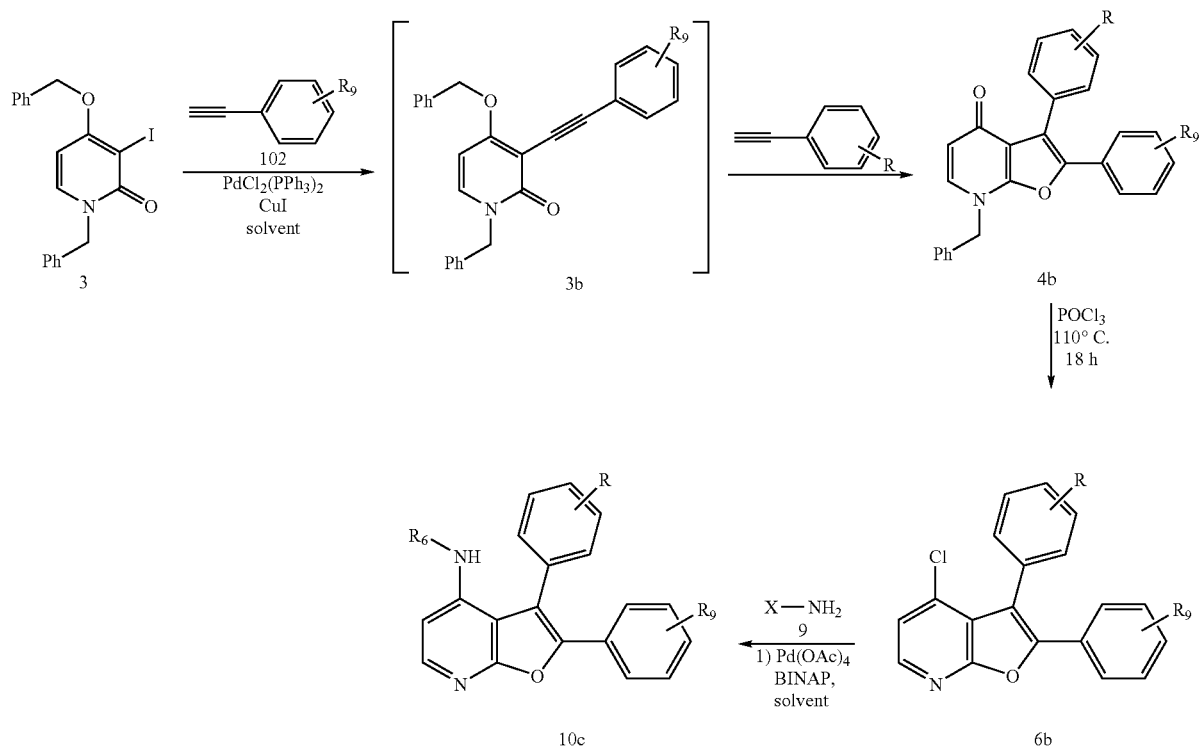

4-Amino-{2-[2-phenyl-substituted)-3-phenyl-substituted furano[2,3-b]pyridines 10c can be prepared by acetylating the iodinated adduct 3 via a copper acetylide intermediate (not shown) in the presence of a suitable palladium catalyst, such as dichloro-diphenylphosphine palladium, followed by quenching the intermediate 3b with a desirable iodide-phenyl-substituted $R^2$ groups, in one reaction step with a suitable solvent and base to install desirable $R^3$ groups on the furan ring. In this fashion desired $R^2$ and $R^3$ groups can advantageously be built into the scaffold simultaneously, as illustrated by compound 4b. Compound 4b can be converted to the corresponding chloro-furano-pyridine 6b with a suitable chloride source such as phosphorus-oxychloride in a suitable solvent. Alternatively, other LG-substituted-furano-pyridines can be made, as appreciated by those skilled in the art. The LG can then be displaced (using palladium chemistry in the case of a chloride) with a suitable nucleophile, such as an $NH_2R^6$ (as shown in 7), an $NHR^6R^7$, an $OR^6$ or $SR^6$ (not shown) to provide the desired $R^6$ and $R^7$ substitutions in place, as shown on compound 10c. The specific methods below exemplify the synthesis of one possible compound 10c (designated as 10d) which can be made by this route.

Specific Methods for Scheme 4

7-Benzyl-2-[4-(2-morpholin-4-yl-ethoxy)-phenyl]-3-phenyl-7H-furo[2,3-b]pyridin-4-one (4c)

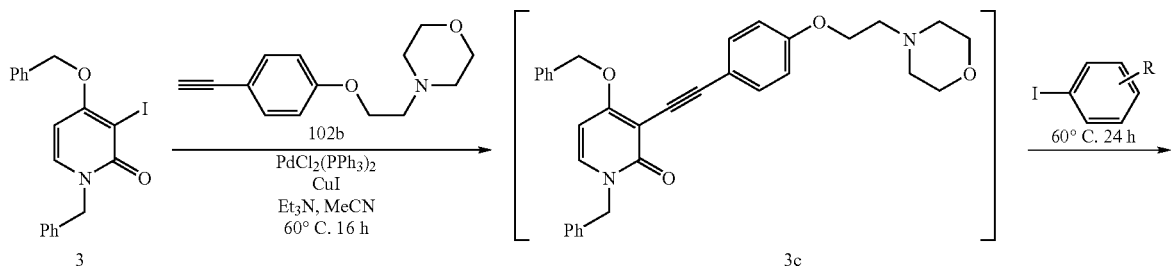

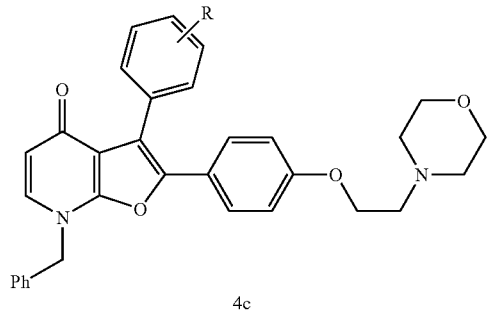

4c

In accordance with a method similar to that described in Bossharth, E.; Desbordes, P; Monteiro, N.; Balme, G. Org. Lett., 5, 2441-2444, 2003, a 15-mL resealable tube was charged with 1-benzyl-4-benzyloxy-3-iodo-2-pyridone (3) (0.300 g, 0.719 mmol), acetonitrile (5 mL), and triethylamine (0.60 mL). Dichlorobis(triphenylphosphine)palladium (II) (0.025 g, 0.036 mmol), copper (I) iodide (0.007 g, 0.036 mmol), and the phenylacetylene 102b (0.199 g, 0.935 mmol) were added. The system was purged with argon, the tube was sealed, and the mixture stirred at 60° C. for 16 h. An aliquot was removed to confirm the presence of the 3-alkynylpyridone (3c) by LC/MS. MS (MH+) 521.2; Calculated 520 for $C_{33}H_{32}N_2O_4$.

Iodobenzene (0.220 g, 0.12 mL, 1.08 mmol) was added and the system was again purged with argon and sealed. The mixture stirred at 60° C. for 24 h to afford a yellow-brown suspension. The mixture was filtered, and the filter cake was triturated with acetonitrile and filtered to afford 7-benzyl-2-[4-(2-morpholin-4-yl-ethoxy)-phenyl]-3-phenyl-7H-furo[2,3-b]pyridin-4-one 4c as an off-white solid. MS (MH+) 507.2; Calculated 506 for $C_{32}H_{30}N_2O_4$.

4-Chloro-2-[4-(2-morpholin-4-yl-ethoxy)-phenyl]-3-phenyl-furo[2,3-b]pyridine (6c)

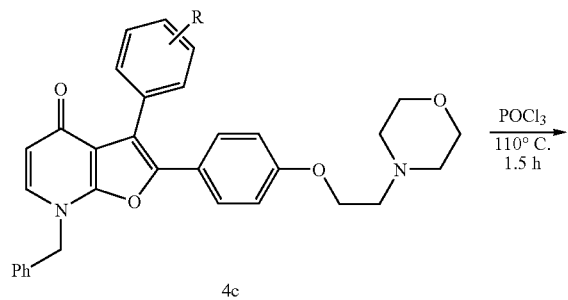

4c

6c

A resealable tube was charged with 7-benzyl-2-[4-(2-morpholin-4-yl-ethoxy)-phenyl]-3-phenyl-7H-furo[2,3-b]pyridin-4-one (4c) (0.100 g, 0.197 mmol) and phosphorous oxychloride (2.0 mL). The system was flushed with argon and the tube was sealed. The mixture stirred at 110° C. for 1.5 h. The reaction mixture was concentrated, and the residue was partitioned between dichloromethane and ice water. The aqueous phase was separated and extracted with dichloromethane. The combined organic phases were washed with saturated aqueous sodium bicarbonate solution, dried over anhydrous sodium sulfate, filtered, and concentrated to afford an orange brown oil. This oil was purified via preparative thin layer chromatography (eluting with 90:10:1, dichloromethane/methanol/ammonium hydroxide) to afford 4-chloro-2-[4-(2-morpholin-4-yl-ethoxy)-phenyl]-3-phenyl-furo[2,3-b]pyridine 6c as an off white solid. MS (MH+) 435.0; Calculated 434 for $C_{25}H_{23}ClN_2O_3$.

4-(2-{2-[4-(2-Morpholin-4-yl-ethoxy)-phenyl]-3-phenyl-furo[2,3-b]pyridin-4-ylamino}-ethyl)-piperazine-1-carboxylic acid tert-butyl ester (10d)

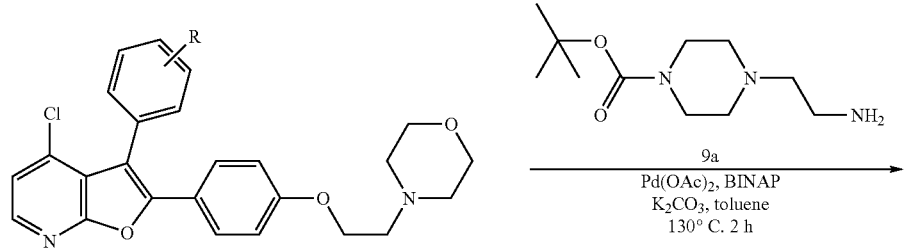

6c

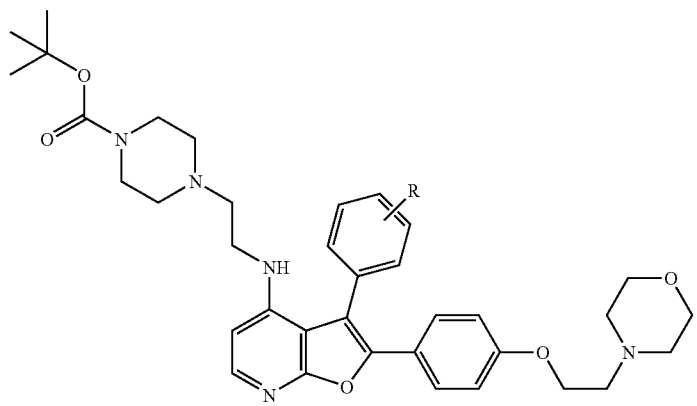

10d

A vial was charged with palladium (II) acetate (0.003 g, 0.011 mmol) and 2,2'-bis(diphenylphosphino)-1,1'-binaphthyl (0.007 g, 0.011 mmol). Toluene (0.5 mL) was added and the system was flushed with argon. The vial was capped and the mixture stirred at room temperature for 15 min.

A resealable tube was charged with 4-chloro-2-[4-(2-morpholin-4-yl-ethoxy)-phenyl]-3-phenyl-furo[2,3-b]pyridine 6c (0.048 g, 0.110 mmol), 4-N-(tert-butoxycarbonyl)-1-aminoethylpiperazine 9a (0.051 g, 0.221 mmol), and potassium carbonate (0.304 g, 2.20 mmol). The Pd/BINAP solution was added along with 1.5 mL of toluene, and the system was flushed with argon. The tube was sealed and the mixture stirred at 130° C. for 2 h. The reaction mixture was partitioned between ethyl acetate and saturated aqueous sodium bicarbonate solution. The aqueous phase was separated and extracted with ethyl acetate. The combined organic phases were washed with saturated aqueous sodium chloride solution, dried over anhydrous sodium sulfate, filtered and concentrated to afford an orange brown oil. This oil was purified via preparative thin layer chromatography (eluting twice with 95:5:0.5, dichloromethane/methanol/ammonium hydroxide) to afford 4-(2-{2-[4-(2-morpholin-4-yl-ethoxy)-phenyl]-3-phenyl-furo[2,3-b]pyridin-4-ylamino}-ethyl)-piperazine-1-carboxylic acid tert-butyl ester 10d as an off white solid. MS (MH$^+$) 628.1; Calculated 627 for $C_{36}H_{45}N_5O_5$.

2-(4-((2-(4-Morpholinyl)ethyl)oxy)phenyl)-3-phenyl-N-(2-(1-piperazinyl)ethyl)furo[2,3-b]pyridin-4-amine (10e)

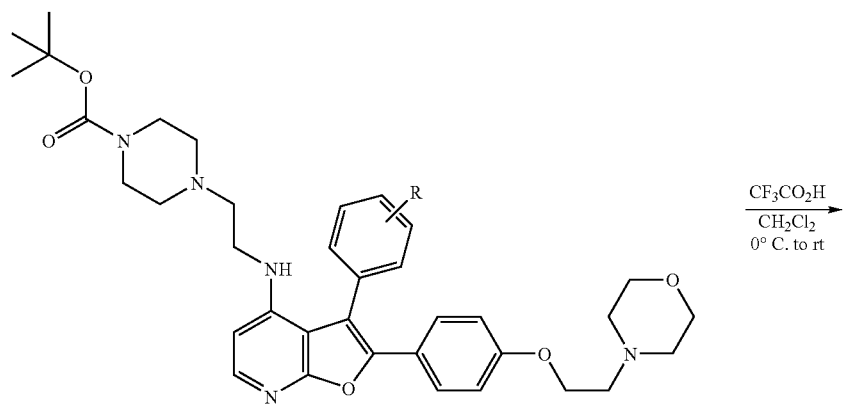

10d $\xrightarrow[\text{CH}_2\text{Cl}_2]{\text{CF}_3\text{CO}_2\text{H}}$
0° C. to rt

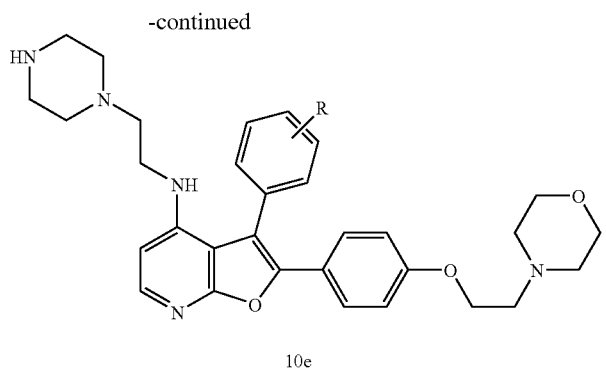

10e

A solution of 4-(2-{2-[4-(2-morpholin-4-yl-ethoxy)-phenyl]-3-phenyl-furo[2,3-b]pyridin-4-ylamino}-ethyl)-piperazine-1-carboxylic acid tert-butyl ester 10d (0.062 g, 0.099 mmol) in dichloromethane (1.0 mL) was cooled to 0° C. Trifluoroacetic acid (0.5 mL) was added and the solution stirred under a nitrogen atmosphere at 0° C. for 15 min and then at room temperature for 2.5 h. The reaction mixture was concentrated and the residue was partitioned between ethyl acetate and saturated aqueous sodium bicarbonate solution. The organic phase was separated and washed with saturated aqueous sodium chloride solution, dried over anhydrous sodium sulfate, filtered and concentrated to afford 2-(4-((2-(4-morpholinyl)ethyl)oxy)phenyl)-3-phenyl-N-(2-(1-piperazinyl)ethyl)furo[2,3-b]pyridin-4-amine 10e as an off-white solid. MS (MH$^+$) 528.3; Calculated 527 for $C_{31}H_{37}N_5O_3$.

57.0 mmol), and acetonitrile (50 mL). The system was flushed with argon, the tube was sealed, and the mixture stirred at 85° C. for 20 h. The reaction mixture was partitioned between ethyl acetate and water. The aqueous phase was separated and extracted with ethyl acetate. The combined organic phases were washed with saturated aqueous sodium chloride solution, dried over anhydrous sodium sulfate, filtered and concentrated to afford a pale orange oil. This oil was purified via column chromatography (eluting with 0-100% ethyl acetate-hexane) to afford 4-[2-(4-iodo-phenoxy)-ethyl]-morpholine 100b as a pale yellow oil. MS (MH$^+$) 334.0; Calculated 333 for $C_{12}H_{16}INO_2$.

4-[2-(4-Ethynyl-phenoxy)-ethyl]-morpholine (102b)

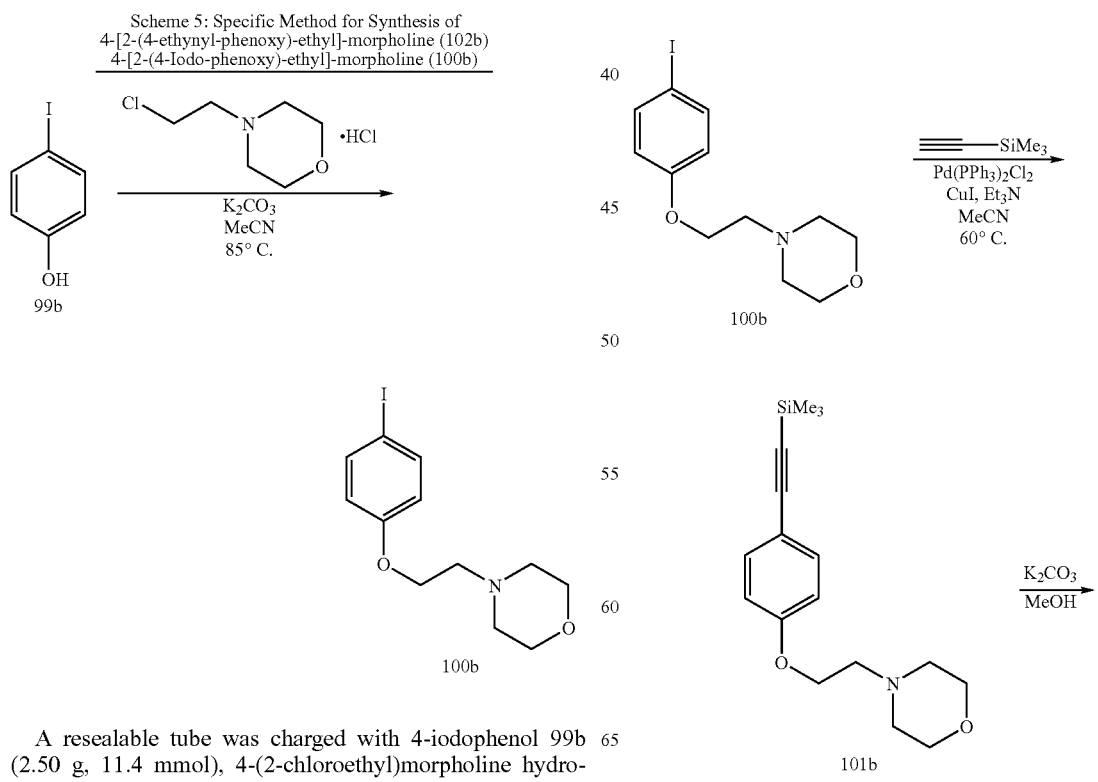

A resealable tube was charged with 4-iodophenol 99b (2.50 g, 11.4 mmol), 4-(2-chloroethyl)morpholine hydrochloride (2.14 g, 11.5 mmol), potassium carbonate (7.88 g,

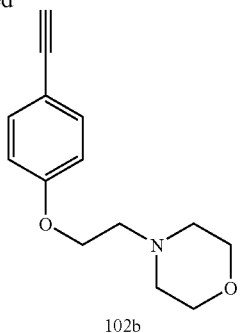

102b

A resealable tube was charged with 4-[2-(4-iodo-phenoxy)-ethyl]-morpholine 100b (2.00 g, 6.00 mmol), acetonitrile (40 mL), and triethylamine (5 mL). Dichlorobis(triphenylphosphine)palladium (II) (0.211 g, 0.30 mmol), copper (I) iodide (0.057 g, 0.30 mmol), and (trimethylsilyl)acetylene (0.766 g, 1.10 mL, 7.80 mmol) were added. The system was purged with argon, the tube was sealed, and the mixture stirred at 60° C. for 16 h. The reaction mixture was concentrated to afford 4-[2-(4-trimethylsilanylethynyl-phenoxy)-ethyl]-morpholine 101b as a dark brown solid which was used without purification. MS (MH+) 304.2; Calculated 303 for $C_{17}H_{25}NO_2Si$.

Potassium carbonate (4.15 g, 30.0 mmol) was added to a solution of the 4-[2-(4-trimethylsilanylethynyl-phenoxy)-ethyl]-morpholine 101b in methanol (25 mL). The mixture stirred at room temperature for 2.5 h and was then filtered through a pad of Celite along with dichloromethane. The filtrate was concentrated and partitioned between dichloromethane and water. The aqueous phase was separated and extracted with dichloromethane. The combined organic phases were washed with saturated aqueous sodium chloride solution, dried over anhydrous sodium sulfate, filtered and concentrated to afford an orange oil. This oil was purified via column chromatography (eluting with 50-100% ethyl acetate-hexane) to afford 4-[2-(4-ethynyl-phenoxy)-ethyl]-morpholine 102b as an orange solid. MS (MH+) 232.2; Calculated 231 for $C_{14}H_{17}NO_2$.

Scheme 6: Alternative General Method for Synthesis of
4-Amino-(2-(2-phenyl-substituted)-3-phenyl-substituted) furano[2,3-b]pyridines

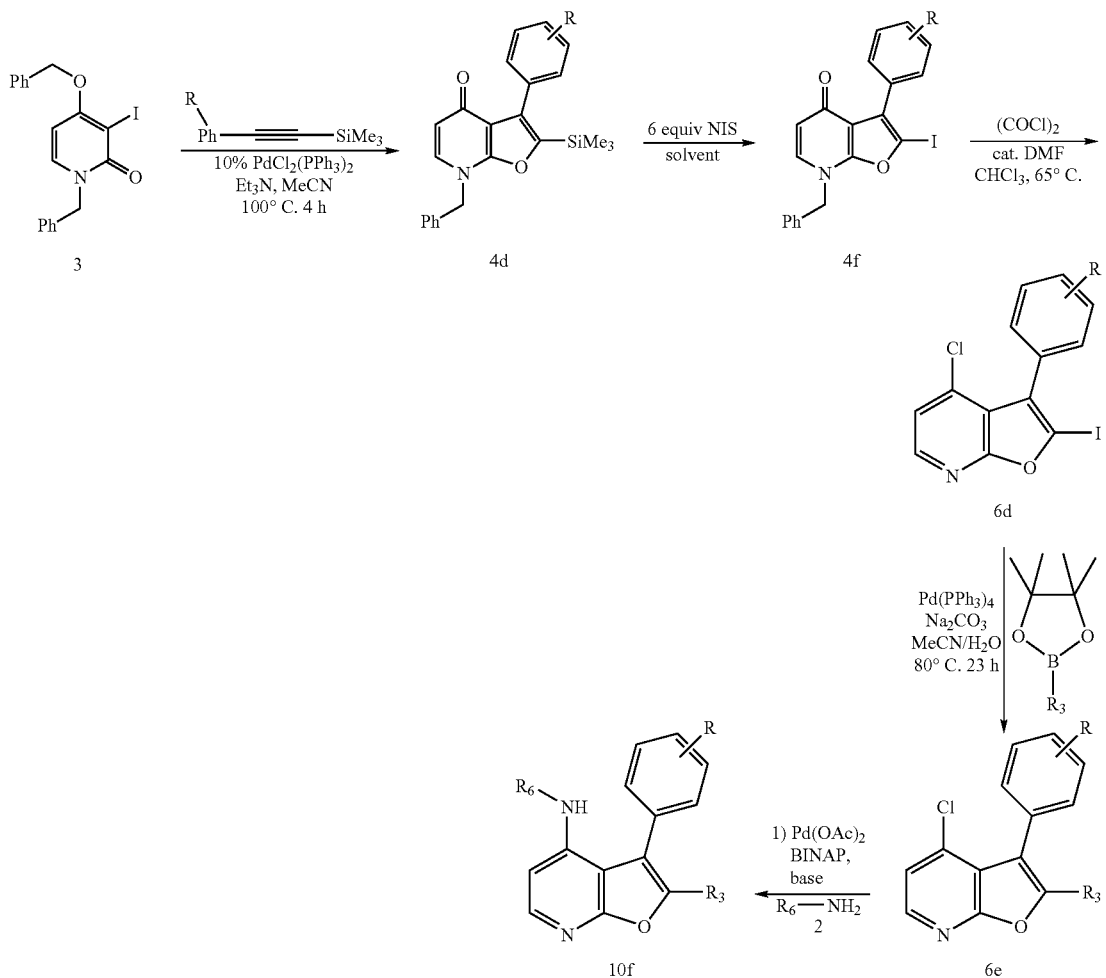

4-Amino-{2-[2-phenyl-substituted)-3-phenyl-substituted furano[2,3-b]pyridines 10f can alternatively be prepared by first forming a silyl-substituted furan-pyridone via reaction of the iodinated adduct 3 with a phenyl-substituted trialkyl-silyl acetylide in the presence of a suitable palladium catalyst, such as dichloro-diphenylphosphine palladium. This method installs desirable phenyl-substituted $R^2$ groups on the furan ring, while allowing modification of the $R^3$ substitution, or the 2-position on the furan ring. The 2-position of the furan ring can be derivatized by converting the trialkylsilyl group to the corresponding iodo with an iodine source, such as NIS, in a suitable solvent to afford compound 4f. Compound 4f can be converted to the corresponding chloro-furano-pyridine 6d in a fashion as previously described herein, i.e., with a suitable chloride source such as oxalylchloride, or other LG in a suitable solvent. The iodo compound 6d can be treated with a desirable boronic acid in a Suzuki-type reaction conditions to build the $R^3$ substitution onto the furan ring. The chloride, or LG, can then be displaced (using palladium chemistry in the case of a chloride) with a suitable nucleophile, such as an $NH_2R^6$ (as shown in 7), an $NHR^6R^7$, an $OR^6$ or $SR^6$ (not shown) to provide the desired $R^6$ and $R^7$ substitutions in place, as shown on compound 10f. The specific methods below exemplify the synthesis of one possible compound 10f (designated as 10g) which can be made by this route.

Specific Methods for Scheme 6

7-benzyl-2-iodo-3-phenylfuro[2,3-b]pyridin-4(7H)-one (4f)

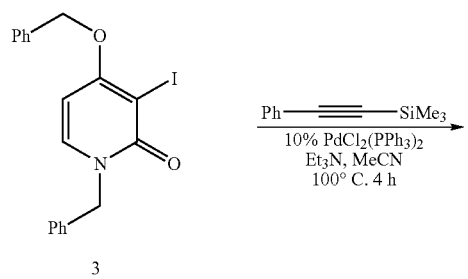

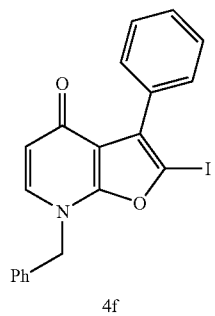

4f

A resealable tube was charged with 1-benzyl-4-benzyloxy-3-iodo-2-pyridone 3 (5.000 g, 11.98 mmol), acetonitrile (100 mL), and triethylamine (6.06 g, 8.35 mL, 59.9 mmol). Dichlorobis(triphenylphosphine)palladium (II) (0.841 g, 1.20 mmol) and 1-phenyl-2-(trimethylsilyl)acetylene were added and argon was bubbled through the solution. The tube was sealed and the mixture stirred at 100° C. for 4 h. The reaction mixture was concentrated to afford 7-benzyl-3-phenyl-2-(trimethylsilyl)furo[2,3-b]pyridin-4(7H)-one 4d as a brown oil. MS (MH+) 374.2; Calculated 373 for $C_{23}H_{23}NO_2Si$.

The 7-benzyl-3-phenyl-2-(trimethylsilyl)furo[2,3-b]pyridin-4(7H)-one 4d was taken up in N,N-dimethylformamide (50 mL), and N-Iodosuccinimide (15.704 g, 69.95 mmol) was added. The mixture stirred at room temperature for 1.5 h and was then concentrated. The residue was partitioned between dichloromethane and an aqueous solution of sodium thiosulfate. The aqueous phase was separated and extracted with dichloromethane. The combined organic phases were washed with brine, dried over anhydrous sodium sulfate, filtered, and concentrated to afford an orange brown oil. Purification via column chromatography on silica gel (eluting with ethyl acetate) afforded 7-benzyl-2-iodo-3-phenylfuro[2,3-b]pyridin-4(7H)-one 4f as a brown solid. MS (MH+) 428.0; Calculated 427 for $C_{20}H_{14}INO_2$.

4-chloro-2-iodo-3-phenylfuro[2,3-b]pyridine (6d)

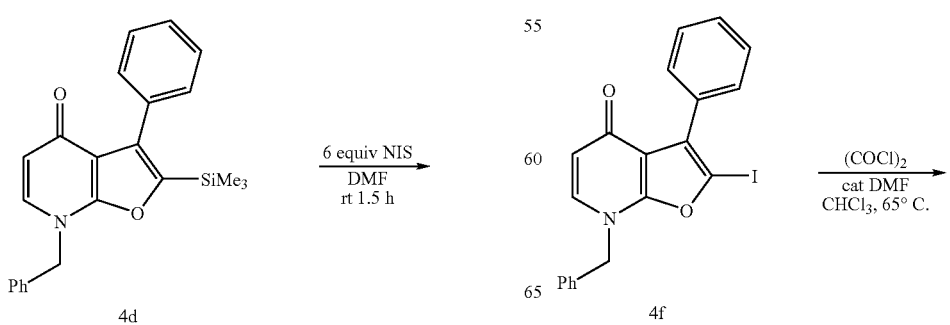

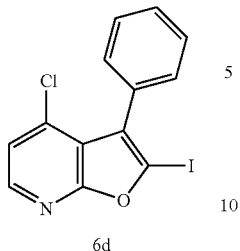

A 100-ml round bottomed flask equipped with a reflux condenser fitted with a nitrogen inlet adapter was charged with 7-benzyl-2-iodo-3-phenylfuro[2,3-b]pyridin-4(7H)-one 4f (3.08 g, 3.46 mmol) and chloroform (35 mL). Oxalyl chloride (1.76 g, 1.21 mL, 13.84 mmol) and N,N-dimethylformamide (0.20 mL) were added, and the reaction was heated at reflux for 18 h. The reaction mixture was concentrated, and the residue was partitioned between dichloromethane and saturated aqueous sodium bicarbonate solution. The aqueous phase was separated and extracted with dichloromethane. The combined organic phases were washed with brine, dried over anhydrous sodium sulfate, filtered, and concentrated to afford a black oil. Purification via column chromatography on silica gel (gradient elution with 0-25% ethyl acetate-hexane) afforded 4-chloro-2-iodo-3-phenylfuro[2,3-b]pyridine 6d as a brown oil. MS (MH+) 356.0; Calculated 355 for $C_{13}H_7ClINO$.

4-chloro-2-(3-fluoro-4-(2-(piperidin-1-yl)ethoxy)phenyl)-3-phenylfuro[2,3-b]pyridine (6e)

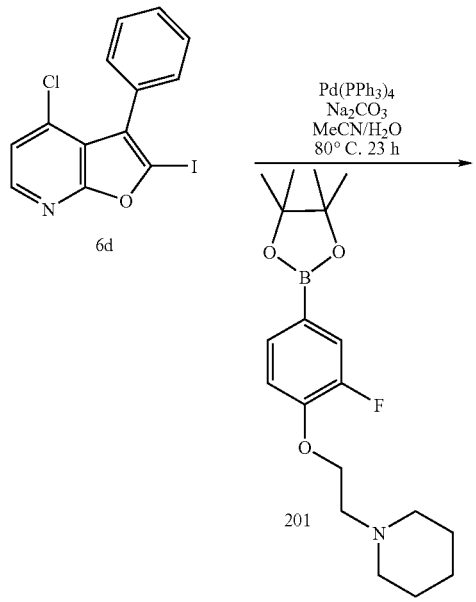

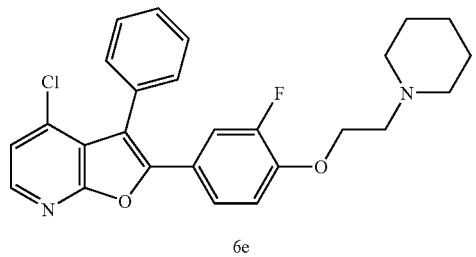

A resealable tube was charged with 4-chloro-2-iodo-3-phenylfuro[2,3-b]pyridine 6d (0.100 g, 0.281 mmol), 1-(2-(2-fluoro-4-(4,4,5,5-tetramethyl-1,3,2-dioxaborolan-2-yl)phenoxy)ethyl)piperidine 201 (0.200 g, 0.576 mmol), sodium carbonate (0.074 g, 0.703 mmol), acetonitrile (4 mL), and water (1 mL). Tetrakis(triphenylphosphine)palladium (0) (0.032 g, 0.028 mmol) was added and the system was purged with argon. The tube was sealed and the mixture stirred at 80° C. for 23 h. The reaction mixture was cooled to room temperature and partitioned between ethyl acetate and saturated aqueous sodium bicarbonate solution. The aqueous phase was separated and extracted with ethyl acetate. The combined organic phases were washed with brine, dried over anhydrous sodium sulfate, filtered, and concentrated to afford a brown oil. Purification via preparative thin layer chromatography (eluting with 95:5:0.5 dichloromethane/methanol/ammonium hydroxide) afforded 4-chloro-2-(3-fluoro-4-(2-(piperidin-1-yl)ethoxy)phenyl)-3-phenylfuro[2,3-b]pyridine 6f as a yellow orange oil. MS (MH+) 451.1; Calculated 450 for $C_{26}H_{24}ClFN_2O_2$.

tert-Butyl 4-(2-(2-(3-fluoro-4-(2-(piperidin-1-yl)ethoxy)phenyl)-3-phenylfuro[2,3-b]pyridin-4-ylamino)ethyl)piperazine-1-carboxylate (step 1 intermediate-not shown)

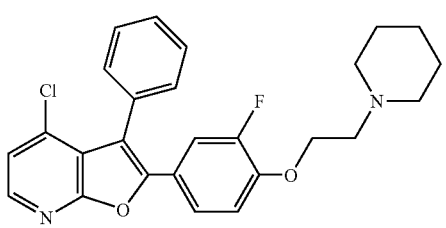

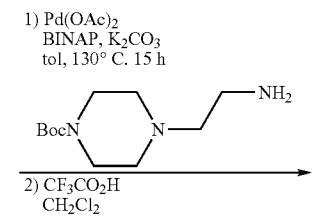

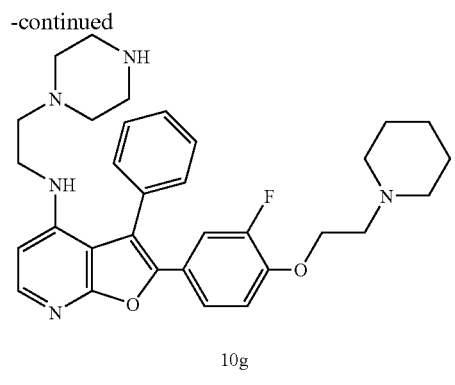

10g

A vial was charged with palladium (II) acetate (0.005 g, 0.021 mmol) and 2,2'-bis(diphenylphosphino)-1,1'-binaphthyl (0.013 g, 0.021 mmol). Toluene (0.5 mL) was added and the system was flushed with argon. The vial was capped and the mixture stirred at room temperature for 15 min.

A resealable tube was charged with 4-chloro-2-(3-fluoro-4-(2-(piperidin-1-yl)ethoxy)phenyl)-3-phenylfuro[2,3-b]pyridine 6e (0.096 g, 0.213 mmol), 4-N-(tert-butoxycarbonyl)-1-aminoethylpiperazine (0.098 g, 0.426 mmol), potassium carbonate (0.589 g, 4.26 mmol), and toluene (3 mL). The Pd/BINAP solution was added along with 1.5 mL of toluene, and the system was flushed with argon. The tube was sealed and the mixture stirred at 130° C. for 20 h. The reaction mixture was partitioned between ethyl acetate and saturated aqueous sodium bicarbonate solution. The aqueous phase was separated and extracted with ethyl acetate. The combined organic phases were washed with saturated aqueous sodium chloride solution, dried over anhydrous sodium sulfate, filtered and concentrated to afford an orange brown oil. This oil was purified via preparative thin layer chromatography (eluting with 95:5:0.5, dichloromethane/methanol/ammonium hydroxide) to afford tert-butyl 4-(2-(2-(3-fluoro-4-(2-(piperidin-1-yl)ethoxy)phenyl)-3-phenylfuro[2,3-b]pyridin-4-ylamino)ethyl)piperazine-1-carboxylate (not shown) as a yellow oil. MS (MH$^+$) 644.4; Calculated 643 for $C_{37}H_{46}FN_5O_4$.

2-(3-fluoro-4-(2-(piperidin-1-yl)ethoxy)phenyl)-3-phenyl-N-(2-(piperazin-1-yl)ethyl)furo[2,3-b]pyridin-4-amine (step 2-10g)

A solution of tert-butyl 4-(2-(2-(3-fluoro-4-(2-(piperidin-1-yl)ethoxy)phenyl)-3-phenylfuro[2,3-b]pyridin-4-ylamino)ethyl)piperazine-1-carboxylate (0.058 g, 0.090 mmol) in dichloromethane (2.0 mL) was cooled to 0° C. Trifluoroacetic acid (1.0 mL) was added and the solution stirred under a nitrogen atmosphere at 0° C. for 2 h. The reaction mixture was concentrated and the residue was partitioned between ethyl acetate and saturated aqueous sodium bicarbonate solution. The organic phase was separated and washed with saturated aqueous sodium chloride solution, dried over anhydrous sodium sulfate, filtered and concentrated to afford a yellow oil. This oil was purified via preparative thin layer chromatography (eluting with 90:10:1, dichloromethane/methanol/ammonium hydroxide) to afford 2-(3-fluoro-4-(2-(piperidin-1-yl)ethoxy)phenyl)-3-phenyl-N-(2-(piperazin-1-yl)ethyl)furo[2,3-b]pyridin-4-amine 10 g as a white solid. MS (MH$^+$) 544.3; Calculated 543 for $C_{32}H_{38}FN_5O_2$.

Scheme 7:
Synthesis of 1-(2-(2-fluoro-4-(4,4,5,5-tetramethyl-1,3,2-dioxaborolan-2-yl)phenoxy)ethyl)piperidine 201

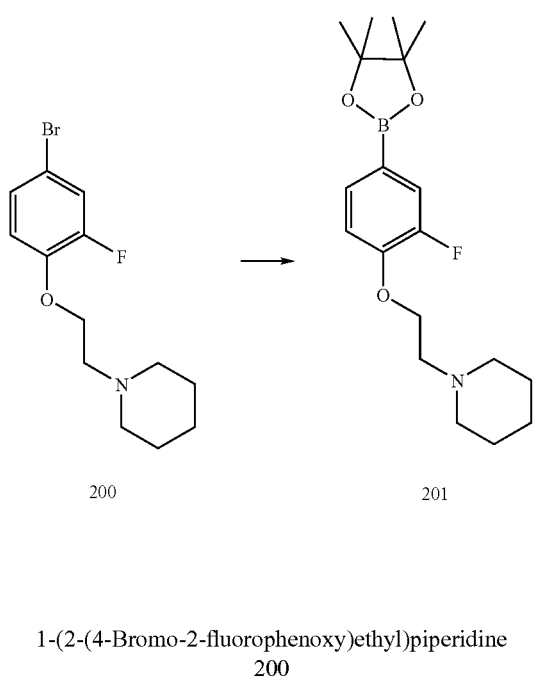

1-(2-(4-Bromo-2-fluorophenoxy)ethyl)piperidine 200

Potassium carbonate (1.7 g, 12 mmol) was added to a solution of 4-bromo-2-fluorophenol (1.00 g, 5.24 mmol) and 1-(2-chloroethyl)piperidine hydrochloride (0.965 g, 5.24 mmol) in acetonitrile (25 mL). The reaction mixture was heated at reflux for 2 days and then cooled to room temperature. The mixture was partitioned between ethyl acetate and water. The aqueous phase was separated and extracted with ethyl acetate. The combined organic phases were dried over anhydrous sodium sulfate, filtered, and concentrated to afford a brown oil. Purification via column chromatography on silica gel (gradient elution with 20-100% ethyl acetate-hexane) afforded 1-(2-(4-bromo-2-fluorophenoxy)ethyl)piperidine 200 as a brown oil. MS (MH$^+$) 302; Calculated 301 for $C_{13}H_{17}BrFNO$.

1-(2-(2-fluoro-4-(4,4,5,5-tetramethyl-1,3,2-dioxaborolan-2-yl)phenoxy)ethyl)piperidine 201

A resealable tube was charged with 1-(2-(4-bromo-2-fluorophenoxy)ethyl)piperidine 200 (0.489 g, 1.62 mmol), bis(pinacolato)diboron (0.493 g, 1.94 mmol), potassium acetate (0.477 g, 4.86 mmol), and dimethylsulfoxide (3 mL). The system was purged with nitrogen and the tube was sealed. The mixture was heated at 80° C. for 3 h. The reaction mixture was purified via column chromatography on silica gel (gradient elution with 3-10% methanol-dichloromethane) afforded 1-(2-(2-fluoro-4-(4,4,5,5-tetramethyl-1,3,2-dioxaborolan-2-yl)phenoxy)ethyl)piperidine 201 as a brown solid. MS (MH$^+$) 350; Calculated 349 for $C_{19}H_{29}BFNO_3$.

Scheme 8: Alternative Scheme for Synthesis of 4-Amino-(2-(2-phenyl-substituted)-3-phenyl-substituted) furano[2,3-b]pyridines Scheme 8 is useful for preparing various desired R groups on a compound of Formula I where $R^3$ is a substituted aryl ring, such as a phenyl ring. The desired R groups can be directly attached to the aryl ring by Sn2 displacement of the bromide, as shown, or other suitable LG's, by suitable nucleophiles, as previously described.

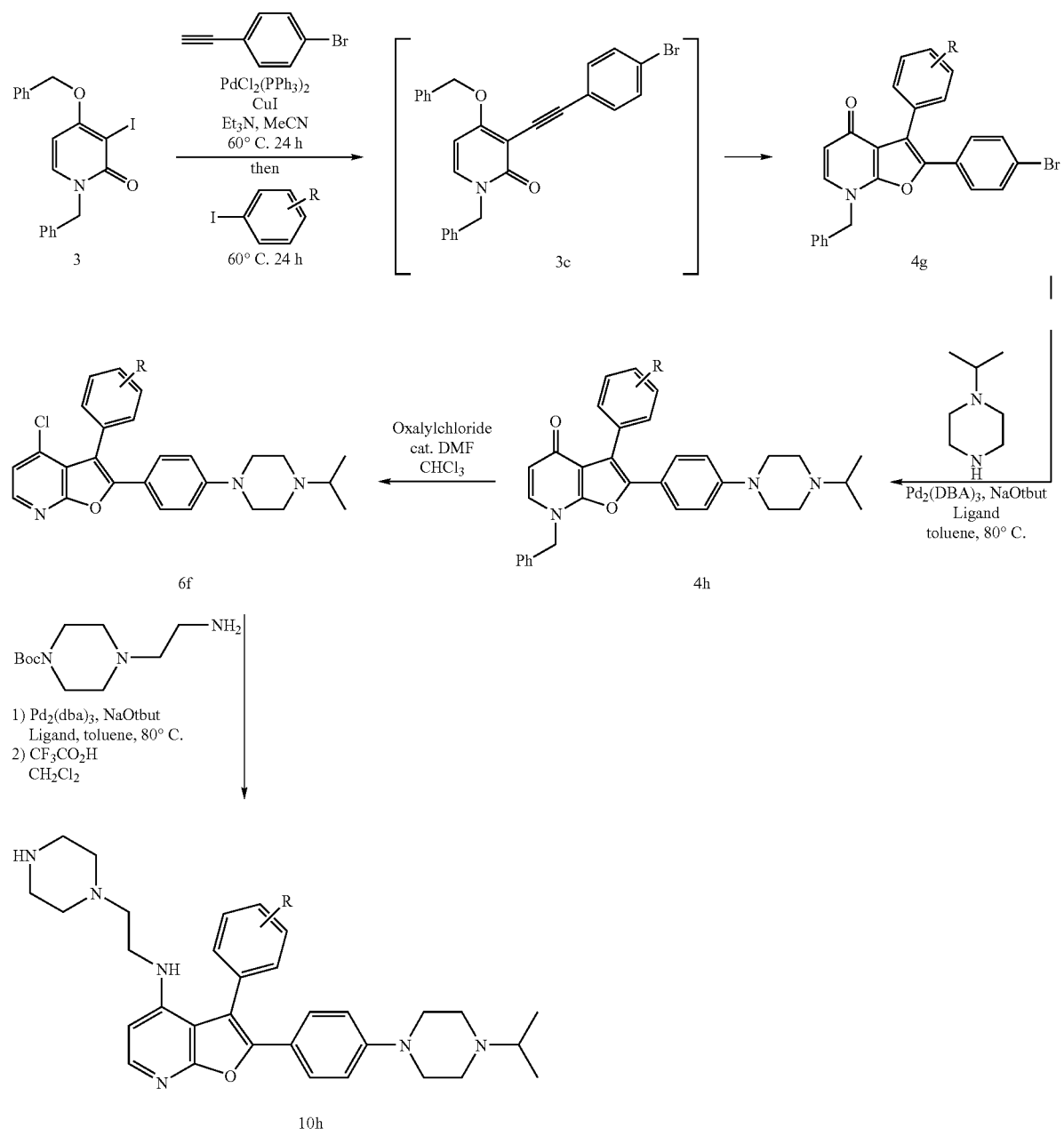

Ligand = 2-dicyclohexylphosphino-2'-(dimethylamino)biphenyl

General Methods

7-Benzyl-2-(4-bromophenyl)-3-phenyl-7H-furo[2,3-b]pyridin-4-one (4g)

A 150-mL resealable tube was charged with 1-benzyl-4-benzyloxy-3-iodo-2-pyridone 3 (4.170 g, 10.00 mmol), acetonitrile (75 mL), and triethylamine (9 mL). Dichlorobis(triphenylphosphine)palladium (II) (0.350 g, 0.500 mmol), copper (I) iodide (0.095 g, 0.500 mmol), and 4-bromophenylacetylene (1.900 g, 10.5 mmol) were added. The system was purged with argon, the tube was sealed, and the mixture stirred at 60° C. for 22 h. An aliquot was removed to confirm the presence of the 3-alkynylpyridone 3c by LC/MS. MS (MH$^+$) 470.2 and 472; Calculated 470.4 for $C_{27}H_{20}BrNO_2$.

Iodobenzene (3.060 g, 15.0 mmol) was added and the system was again purged with argon and sealed. The mixture stirred at 60° C. for 22 h to afford a yellow suspension. The mixture was filtered, and the filter cake was washed with acetonitrile and filtered to afford 7-benzyl-2-(4-bromophenyl)-3-phenyl-7H-furo[2,3-b]pyridin-4-one 4g as an off-white solid. MS (MH$^+$) 456.4 and 458.3; Calculated 456.3 for $C_{26}H_{18}BrNO_2$.

7-Benzyl-2-(4-(4-isopropylpiperazinl-1-yl)phenyl)-3-phenylfuro[2,3-b]pyridin-4(7H)-one (4h)

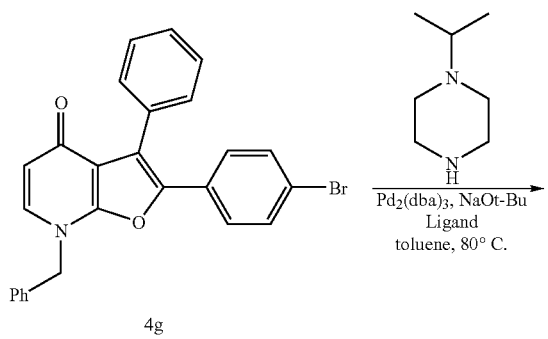

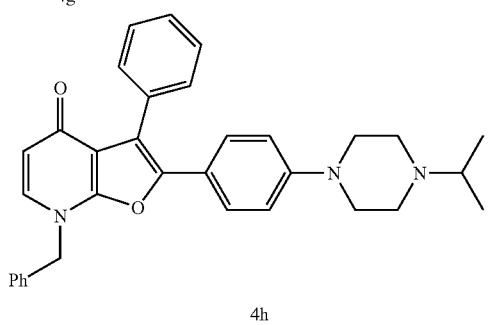

A 16 by 100 mm resealable tube was charged with 7-Benzyl-2-(4-bromophenyl)-3-phenyl-7H-furo[2,3-b]pyridin-4-one 4g (0.500 g, 1.096 mmol), N-isopropylpiperizine (0.169 g, 1.315 mmol), tris(dibenzylideneacetone)dipalladium (0.010 g, 0.011 mmol), sodium tertbutoxide (0.015 g, 1.560 mmol), 2-dicyclohexylphosphino-2'-(dimethylamino)biphenyl (0.013 g, 0.033 mmol), and toluene (4 mL). The system was purged with argon, the tube was sealed, and the mixture stirred at 80° C. for 24 h. The reaction mixture was concentrated to afford a red-brown oil which was purified via column chromatography on silica gel (eluting with 0-10% methanol-dichloromethane) to afford 7-benzyl-2-(4-(4-isopropylpiperazinl-1-yl)phenyl)-3-phenylfuro[2,3-b]pyridin-4(7H)-one 4h as a red solid. MS (MH$^+$) 504.0; Calculated 503.63 for $C_{33}H_{33}N_3O_2$.

4-chloro-2-(4-(4-isopropylpiperazinl-1-yl)phenyl)-3-phenylfuro[2,3-b]pyridine (6f)

4-chloro-2-(4-(4-isopropylpiperazinl-1-yl)phenyl)-3-phenylfuro[2,3-b]pyridine was synthesized using the procedure in Method A for the preparation of 4-(4-chloro-3-phenyl-furo[2,3-b]pyridin-2-yl)-phenol. MS (MH$^+$) 432; Calculated 431.18 for $C_{26}H_{26}ClN_3O$.

Tert-butyl-4-(2-(4-(4-isopropylpiperazinl-1-yl)phenyl)-3-phenylfuro[2,3-b]pyridin-4-ylamino)ethyl)piperizine-1-carboxylate (not shown)

Tert-butyl-4-2-(4-(4-isopropylpiperazinl-1-yl)phenyl)-3-phenyl-N-(2-(piperazin-1-yl)ethyl)furo[2,3-b]pyridin-4-amine (not shown) was synthesized using the procedure outlined above for the preparation of 7-benzyl-2-(4-(4-isopropylpiperazinl-1-yl)phenyl)-3-phenylfuro[2,3-b]pyridin-4(7H)-one. MS (MH$^+$) 625; Calculated 624.38 for $C_{37}H_{48}N_6O_3$.

2-(4-(4-(1-methylethyl)-1-piperazinyl)phenyl)-3-phenyl-N-(2-(1piperazinyl)ethyl)furo[2,3-b]pyridin-4-amine (10h)

2-(4-(4-(1-Methylethyl)-1-piperazinyl)phenyl)-3-phenyl-N-(2-(1-piperazinyl)ethyl)furo[2,3-b]pyridin-4-amine 10h was synthesized using the procedure in described in specific methods for Scheme 6, wherein the Boc-protected piperazine compound (above) was treated with trifluoroacetic acid in dichloromethane, and de-protected to yield compound 10h. MS (MH$^+$) 525; Calculated 524.3 for $C_{32}H_{40}N_6O$.

Scheme 9:
Alternative General Scheme for Synthesis of
4-Amino-(2-(2-phenyl-substituted)-3-phenyl) furano[2,3-b]pyridines

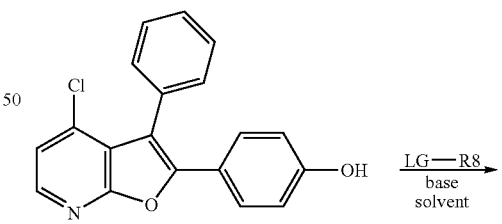

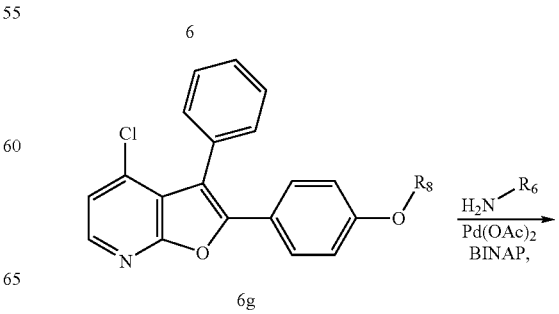

-continued

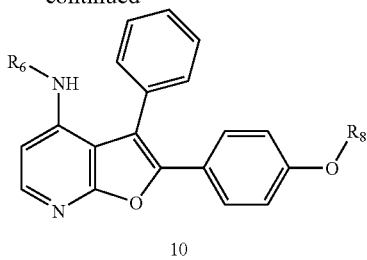

10

Scheme 9 is useful for preparing various desired R⁶ groups and alkoxy-R groups on compounds of Formula I where R¹ is NHR⁶ and R³ is alkoxy-substituted phenyl rings, respectively. The desired R⁶ groups can generally be inserted onto the pyridine ring via the chloro-pyridyl intermediate 6g, as previously described, while the alkoxy-subsitutent can be added via typical LG chemistry. The specific methods below exemplify the synthesis of one possible compound 10 (designated as 10i) which can be made by this route.

Specific Methods for Scheme 9

{2-[4-2-piperidine-ethoxy)-phenyl]-3-phenyl-4-chloro-furo[2,3-b]pyridine (6h)}

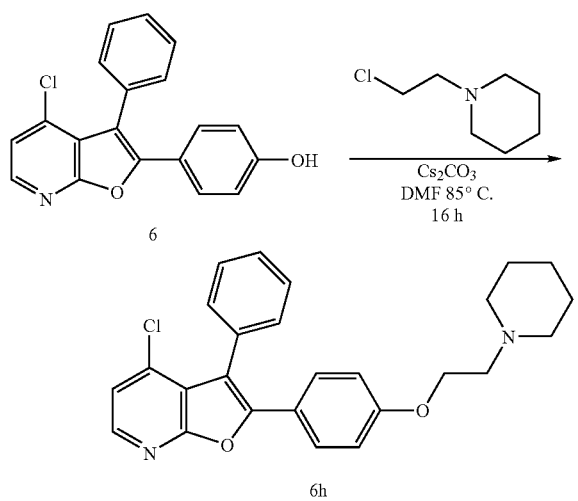

A resealable tube was charged with 4-(4-chloro-3-phenyl-furo[2,3-b]pyridin-2-yl)-phenol 6 (0.10 g, 0.3 mmol), 1-(2-chloroethyl)piperidine (0.063 g, 0.3 mmol), cesium carbonate (0.51 g, 1.6 mmol), and DMF (2.0 mL). The system was purged with argon and the tube was sealed. The mixture stirred at 85° C. for 18 h. The reaction mixture was then partitioned between ethyl acetate and water. The aqueous phase was separated and extracted with ethyl acetate. The combined organic phases were washed with saturated aqueous sodium chloride solution, dried over anhydrous sodium sulfate, filtered, and concentrated to afford {2-[4-2-piperidine-ethoxy)-phenyl]-3-phenyl-4-chloro-furo[2,3-b]pyridine 6h as a yellow solid. MS (MH⁺) 433.1; Calculated 432 for $C_{26}H_{25}ClN_2O_2$.

{2-[4-2-piperidine-ethoxy)-pheynl]-3-phenyl-N-(2-(4-pyridyl)ethyl)furo[2,3-b]pyridine-4-amine (10)}

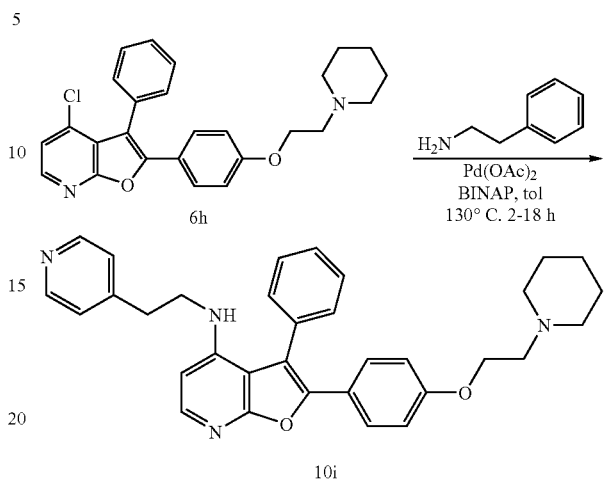

A vial was charged with palladium (II) acetate (0.0032 g, 0.004 mmol) and 2,2'-bis(diphenylphosphino)-1,1'-binaphthyl (0.009 g, 0.044 mmol). Toluene (1.0 mL) was added and the system was flushed with argon. The vial was capped and the mixture stirred at room temperature for 15 min.

A resealable tube was charged with {2-[4-2-piperidine-ethoxy)-phenyl]-3-phenyl-4-chloro-furo[2,3-b]pyridine 6h (0.062 g, 0.1 mmol), 4-(2-aminoethyl)pyridine (0.035 g, 0.3 mmol), and potassium carbonate (0.4 g, 2.9 mmol). The Pd/BINAP solution was added along with 2.0 mL of toluene, and the system was flushed with argon. The tube was sealed and the mixture stirred at 130° C. for 18 h. The reaction mixture was partitioned between ethyl acetate and saturated aqueous sodium bicarbonate solution. The aqueous phase was separated and extracted with ethyl acetate. The combined organic phases were washed with saturated aqueous sodium chloride solution, dried over anhydrous sodium sulfate, filtered and concentrated to afford a brown solid. This material was purified via column chromatography on silica gel (eluting with 0-50% (90:10:1, dichloromethane/methanol/ammonium hydroxide)-dichloromethane) to afford {2-[4-2-piperidine-ethoxy)-pheynl]-3-phenyl-N-(2-(4-pyridyl)ethyl)furo[2,3-b]pyridine-4-amine 10i as an orange solid. MS (MH⁺) 519.3; Calculated 518 for $C_{33}H_{34}N_4O_2$.

Scheme 10:
General Method for Synthesis of 5-substituted Furano-Pyridines

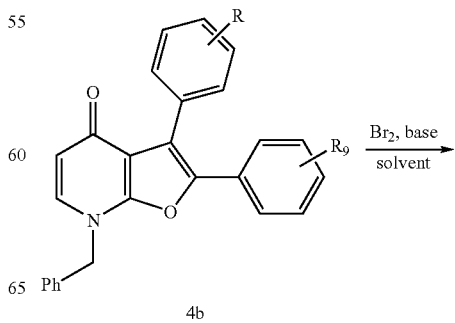

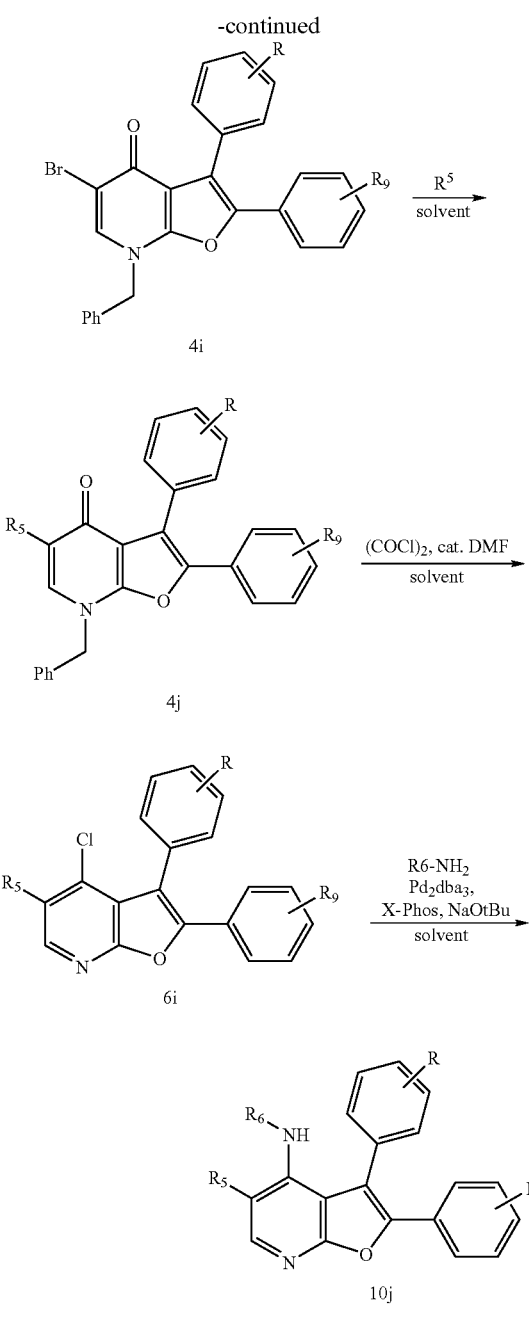

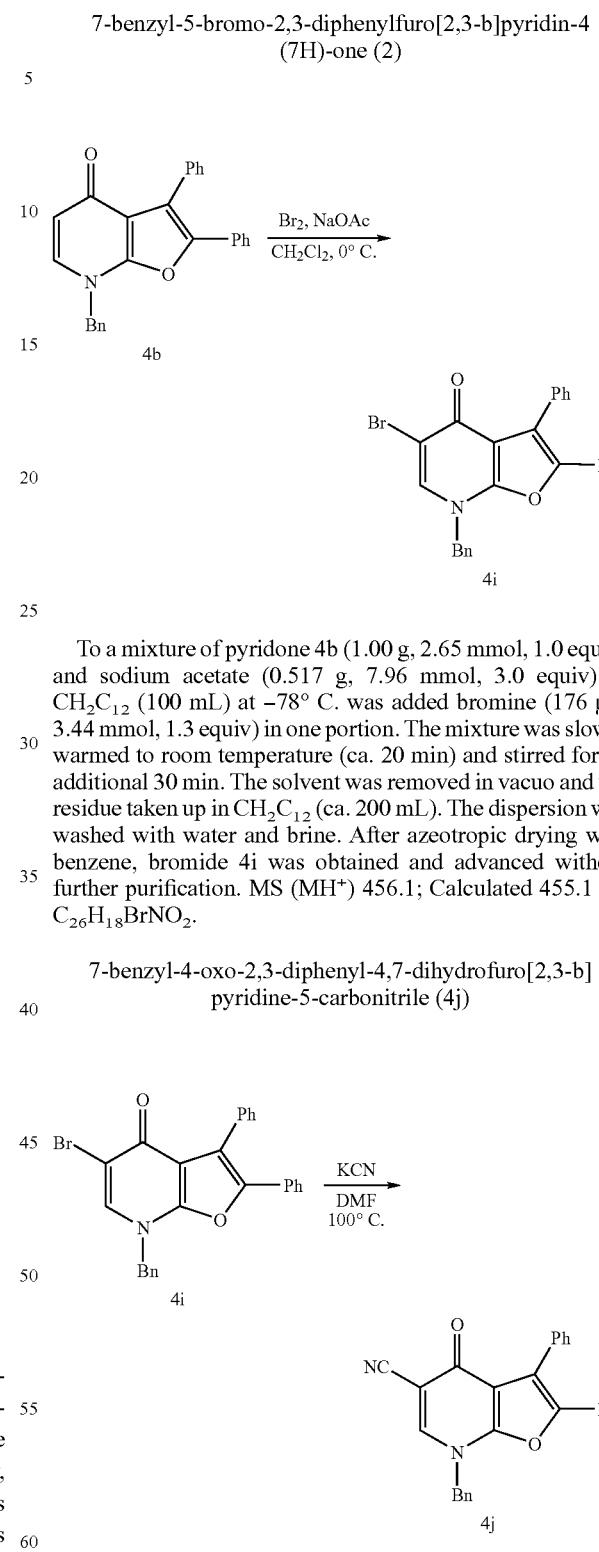

Specific Methods for Scheme 10

7-benzyl-5-bromo-2,3-diphenylfuro[2,3-b]pyridin-4(7H)-one (2)

To a mixture of pyridone 4b (1.00 g, 2.65 mmol, 1.0 equiv) and sodium acetate (0.517 g, 7.96 mmol, 3.0 equiv) in $CH_2Cl_2$ (100 mL) at −78° C. was added bromine (176 μL, 3.44 mmol, 1.3 equiv) in one portion. The mixture was slowly warmed to room temperature (ca. 20 min) and stirred for an additional 30 min. The solvent was removed in vacuo and the residue taken up in $CH_2Cl_2$ (ca. 200 mL). The dispersion was washed with water and brine. After azeotropic drying with benzene, bromide 4i was obtained and advanced without further purification. MS (MH$^+$) 456.1; Calculated 455.1 for $C_{26}H_{18}BrNO_2$.

7-benzyl-4-oxo-2,3-diphenyl-4,7-dihydrofuro[2,3-b]pyridine-5-carbonitrile (4j)

To bromide 4i (1.13 g, 2.48 mmol, 1.0 equiv) in DMF (20 mL) was added potassium cyanide (484 mg, 7.43 mmol, 3.0 equiv). The mixture heated to 100° C. for 12 hrs. After cooling to room temperature, the solvent was removed in vacuo and the residue treated with EtOAc (200 mL) and water (100 mL). After thorough mixing in a separatory funnel, the dispersion 5-R$^5$-4-Amino-{2-[2-phenyl-substituted)-3-phenyl-substituted furano[2,3-b]pyridines 10j can be prepared by converting compound 4b to the corresponding 5-bromo-furanopyridone 4j with a suitable bromide source, such as bromine in solution, with a base in a suitable solvent. Alternatively, other 5-LG-substituted-furano-pyridones can be made, as appreciated by those skilled in the art. The LG (bromine as shown in scheme 10) can then be displaced with a suitable nucleophilic R$^5$ group, such as CN, amine, alkoxides, sulfoxides and the like, to provide the desired R$^5$ substitutions in place, as shown on compound 10j. The specific methods below exemplify the synthesis of one possible compound 10j (designated as 10k) which can be made by this route.

was filtered and the isolated precipitate was set aside. The organic layer was separated and washed with $H_2O$ and brine. Benzene was added and the solution was concentrated under reduced pressure. The resulting solid was combined with the previously isolated precipitate to afford nitrile 4j, which was advanced without further purification. MS ($MH^+$) 403; Calculated 402.1 for $C_{27}H_{18}N_2O_2$.

4-chloro-2,3-diphenylfuro[2,3-b]pyridine-5-carbonitrile (4j)

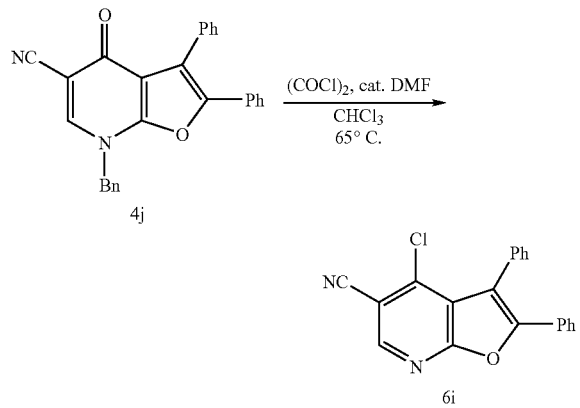

To a mixture of nitrile 4j (0.847 g, 2.11 mmol, 1.0 equiv) in $CHCl_3$ (30 mL) was added oxalyl chloride (0.55 mL, 6.32 mmol, 3.0 equiv) followed by DMF (ca. 30 µL). The mixture was heated to 65° C. After 3 hr, the solvent was removed in vacuo. The resulting residue was taken up in $CH_2Cl_2$ (25 mL) and stirred viorously with 1 N NaOH (ca. 5 mL) for 5 min. The organic layer was washed with brine and dried with $MgSO_4$. Removal of the solvent under reduced pressure gave chloride 6i. An analytical sample could be obtained by silica gel chromatography with 9:1 hexanes:EtOAc. MS ($MH^+$) 331; Calculated 330.1 for $C_{20}H_{11}ClN_2O$.

2,3-diphenyl-4-(((2S)-tetrahydro-2-furanylmethyl) amino)furo[2,3-b]pyridine-5-carbonitrile (10k)

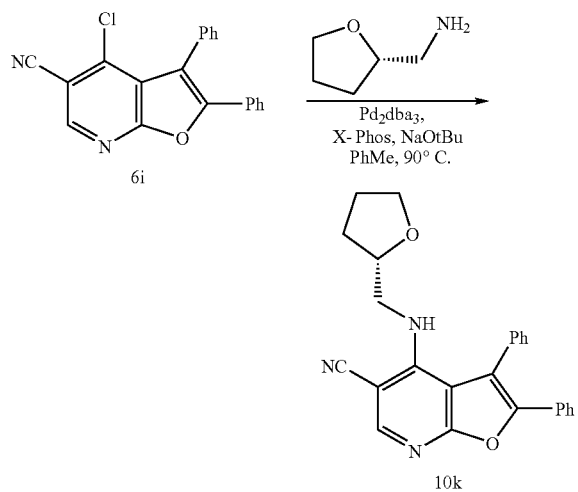

To a mixture of 6i (100 mg, 0.303 mmol, 1.0 equiv), $Pd_2dba_3$ (27 mg, 0.0303 mmol, 0.10 equiv), 2-Dicyclohexylphosphino-2', 4', 6'-tri-1-propyl-1,1'-biphenyl (17 mg, 0.036 mmol, 0.12 equiv), and NaOtBu (58 mg, 0.606 mmol, 2.0 equiv) was added toluene (5 mL). After 1 min of vigorous stirring, S-(+)-tetrahydrofurfuryl amine (63 µL, 0.606 mmol, 2.0 equiv) was added and the mixture was heated to 90° C. After the starting material was consumed as indicated by TLC, the solvent was removed in vacuo. The residue was taken up in EtOAc (50 mL) and washed with water and brine. After drying over $MgSO_4$ the mixture was concentrated and purified by silica gel chromatography (3:1 hexanes:EtOAc) to afford the amine 10k. MS ($MH^+$) 396; Calculated 395.2 for $C_{25}H_{21}N_3O_2$.

Scheme 11:
General Method for Synthesis of 5-substituted Furano-Pyridines

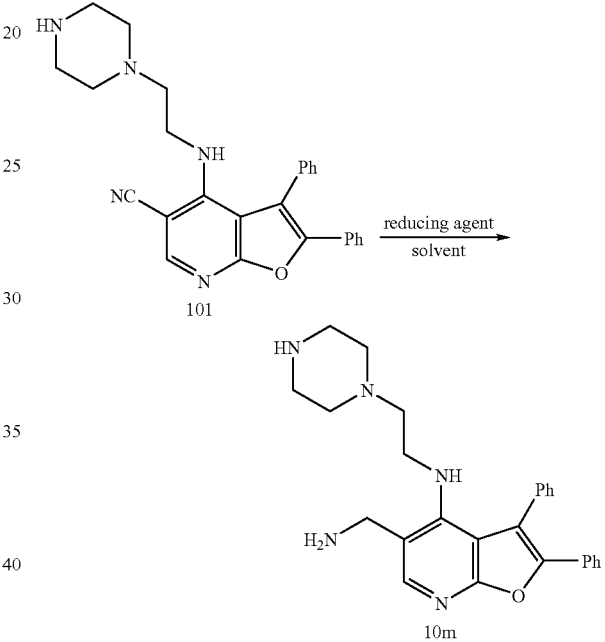

Scheme 11 illustrates how the 5-position of the pyridine ring can be further functionalized, utilizing the 5-cyano intermediate similar to that shown in compound 10j. Particularly, the cyano group can be reduced with a suitable reducing agent or hydrogen donor, such as a hydride (as described below) to afford the corresponding primary amine. The amine then can be functionalized in a variety of conventional methods to the desired amino groups, amides, ureas and the like, as appreciated by those skilled in the art.

Specific Methods for Scheme 11

5-(aminomethyl)-2,3-diphenyl-N-(2-(1-piperazinyl) ethyl)furo[2,3-b]pyridin-4-amine (10m)

To a mixture of nitrile 101 (38 mg, 0.089 mmol, 1.0 equiv) and THF (5 mL) at 25° C., was added $LiAlH_4$ (17 mg, 0.450 mmol, 5.0 equiv). After 24 h, $H_2O$ (50 µL) was added followed by 1N NaOH (100 µL). Concentration in vacuo provided a residue that was taken up in $CH_2Cl_2$ (20 mL) and extracted with 1N HCl. The aqueous fractions were combined, basified with 1N NaOH, and extracted with $CH_2Cl_2$. After drying with $MgSO_4$ and concentration in vacuo, the resulting residue was purified by reverse phase MPLC (MeCN:H$_2$O) to afford amine 7. MS (MH$^+$) 428.2; Calculated 427.2 for C$_{26}$H$_{29}$N$_5$O.

Scheme 12: Alternative Method for Synthesis of NHR$^6$ groups.

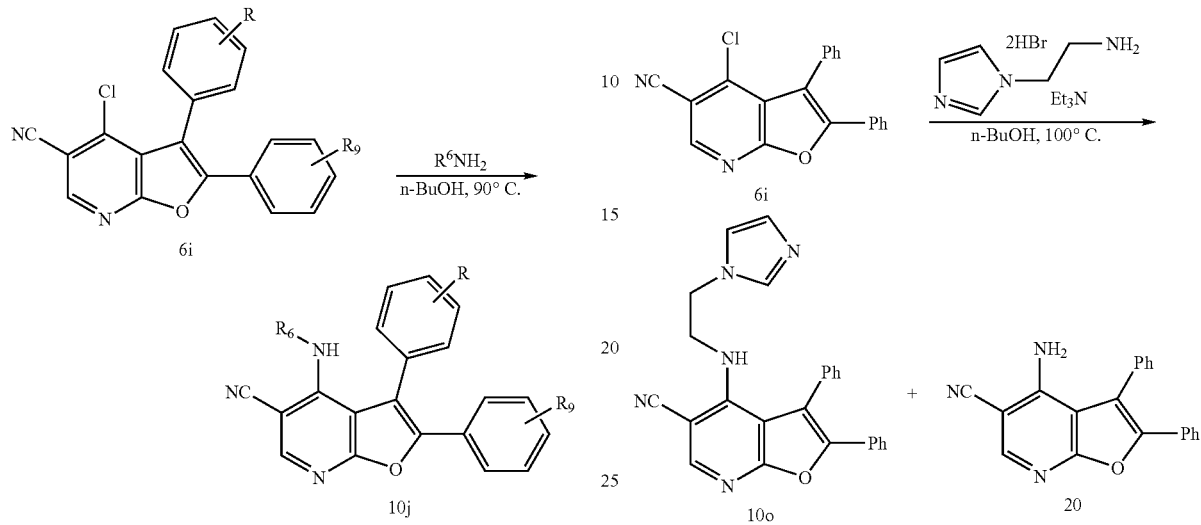

Specific Methods for Scheme 12

4-(5-(diethylamino)pentan-2-ylamino)-2,3-diphenyl-furo[2,3-b]pyridine-5-carbonitrile (10n)

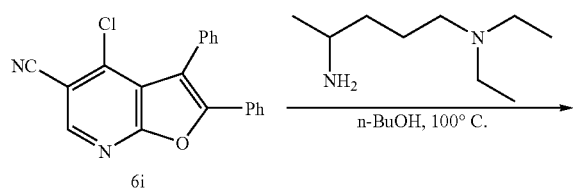

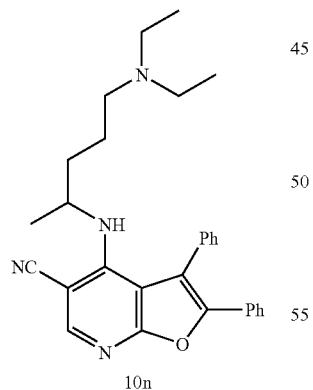

To a mixture of 6i (100 mg, 0.303 mmol, 1.0 equiv) in n-BuOH (5 mL) was added (±)-2-amino-5-diethylaminopentane (0.587 mL, 3.03 mmol, 10.0 equiv). After heating at 100° C. for 24 hrs, the solvent was removed in vacuo. The resulting residue was purified by silica gel chromatography (5% MeOH:CH$_2$Cl$_2$) to afford amine 10n. MS (MH$^+$) 453.5; Calculated 452.3 for C$_{29}$H$_{32}$N$_4$O.

4-((2-(1H-imidazol-1-yl)ethyl)amino)-2,3-diphenyl-furo[2,3-b]pyridine-5-carbonitrile (10o) and 4-amino-2,3-diphenylfuro[2,3-b]pyridine-5-carbonitrile (20)

To a mixture of 6i (40 mg, 0.121 mmol, 1.0 equiv) in n-BuOH (5 mL) was added 2-(1H-imidazol-1-yl)ethanamine dihydrobromide (198 mg, 0.727 mmol, 6.0 equiv) and Et$_3$N (203 µL, 1.45 mmol, 12.0 equiv). After heating at 100° C. for 24 hrs, the solvent was removed in vacuo and the resulting residue was taken up in CH$_2$Cl$_2$ (20 mL). The mixture was washed with H$_2$O, brine, and dried with MgSO$_4$. Purification by silica gel chromatography (5% MeOH:CH$_2$Cl$_2$) afforded amine 10o [MS (MH$^+$) 406.1; Calculated 405.2 for C$_{25}$H$_{19}$N$_5$O] and amine 20 [MS (MH$^+$) 312.1; Calculated 311.1 for C$_{20}$H$_{13}$N$_3$O].

Scheme 13:
Alternative General Methods for
Synthesis of Various R$^5$ substituents of Compounds of Formula I

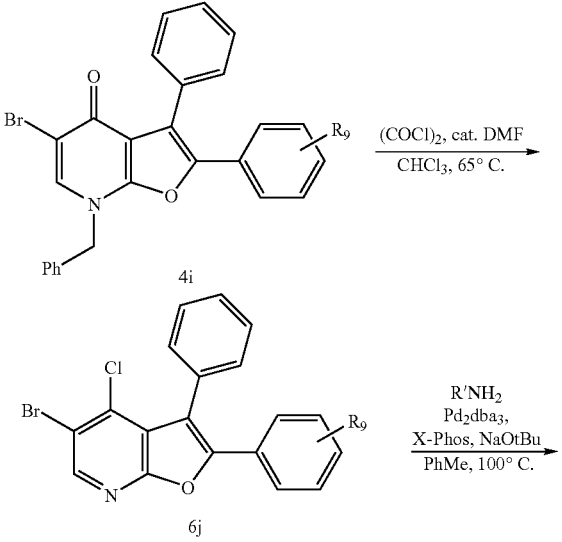

4-chloro-2,3-diphenyl-N-((2S)-tetrahydro-2-furanyl-methyl)furo[2,3-b]pyridin-5-amine (6l)

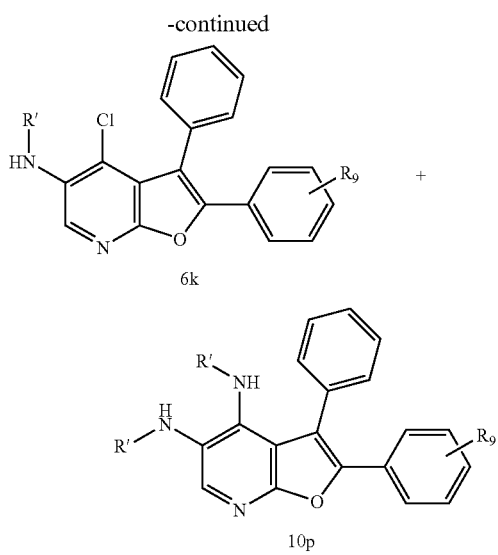

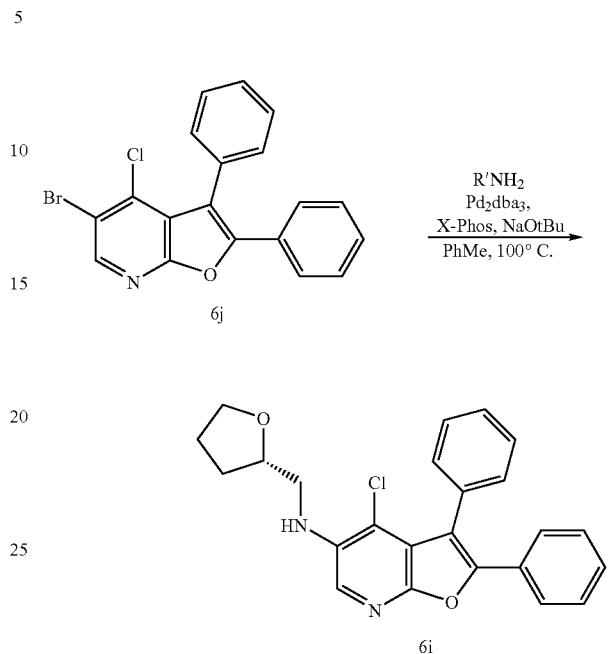

Specific Methods for Scheme 13

5-bromo-4-chloro-2,3-diphenylfuro[2,3-b]pyridine (6j)

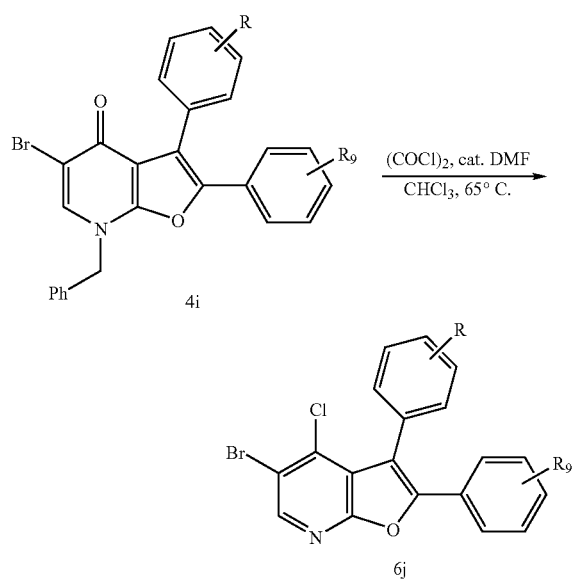

To a mixture of bromide 4i (0.960 g, 2.11 mmol, 1.0 equiv) in CHCl$_3$ (30 mL) was added oxalyl chloride (0.55 mL, 6.32 mmol, 3.0 equiv) followed by DMF (ca. 30 μL). The mixture was heated to 65° C. After 3 hr, the solvent was removed in vacuo. The resulting residue was taken up in CH$_2$Cl$_2$ (25 mL) and stirred viorously with 1 N NaOH (ca. 5 mL) for 5 min. The organic layer was washed with brine and dried with MgSO$_4$. Removal of the solvent under reduced pressure gave chloride 6j. An analytical sample could be obtained by silica gel chromatography (9:1 hexanes:EtOAc). MS (MH$^+$) 384; Calculated 383.0 for C$_{19}$H$_{11}$BrClNO.

To a mixture of 6j (116 mg, 0.303 mmol, 1.0 equiv), Pd$_2$dba$_3$ (27 mg, 0.0303 mmol, 0.10 equiv), 2-Dicyclohexylphosphino-2', 4', 6'-tri-i-propyl-1,1'-biphenyl (17 mg, 0.036 mmol, 0.12 equiv), and NaOtBu (58 mg, 0.606 mmol, 2.0 equiv) was added toluene (5 mL) which was first purged with argon. After 1 min of vigorous stirring, S-(+)-Tetrahydrofurfuryl amine (63 μL, 0.606 mmol, 2.0 equiv) was added and the mixture was heated to 100° C. After starting material was consumed as indicated by TLC, the solvent was removed in vacuo. The resulting residue was taken up in EtOAc (50 mL) and washed with water and brine. After drying with MgSO$_4$ and removing the solvent in vacuo, the crude mixture was purified by silica gel chromatography (3:1 hexanes:EtOAc) to afford amine 6l. MS (MH$^+$) 405.0; Calculated 404.1 for C$_{24}$H$_{21}$ClN$_2$O$_2$.

N,N'-bis (4-(1,1-dimethylethyl)phenyl)-2,3-diphenylfuro[2,3-b]pyridine-4,5-diamine (10q)

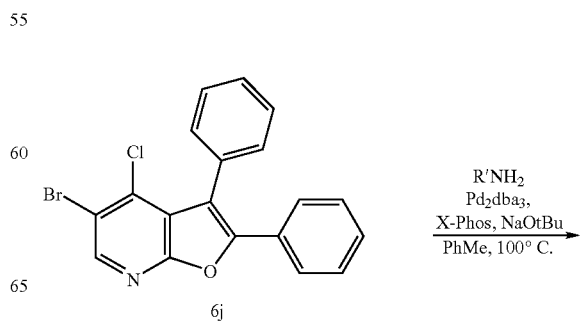

-continued

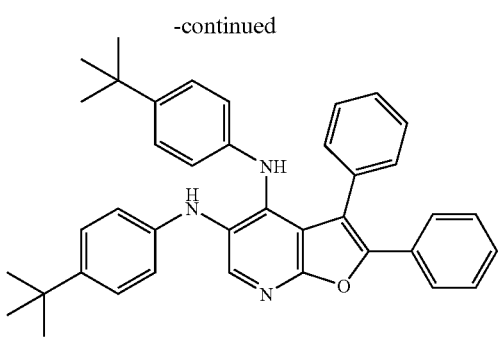

10q

To a mixture of 6j (116 mg, 0.303 mmol, 1.0 equiv), Pd$_2$dba$_3$ (27 mg, 0.0303 mmol, 0.10 equiv), 2-Dicyclohexylphosphino-2', 4', 6'-tri-1-propyl-1,1'-biphenyl (17 mg, 0.036 mmol, 0.12 equiv), and NaOtBu (58 mg, 0.606 mmol, 2.0 equiv) was added toluene (5 mL) which was first purged with argon. After 1 min of vigorous stirring, 4-t-butyl aniline (90 mg, 0.606 mmol, 2.0 equiv) was added and the mixture was heated to 100° C. After starting material was consumed as indicated by TLC, the solvent was removed in vacuo. The resulting residue was taken up in EtOAc (50 mL) and washed with water and brine. After drying with MgSO$_4$ and removing the solvent in vacuo, the crude mixture was purified by silica gel chromatography (3:1 hexanes:EtOAc) to afford amine 10q; MS (MH$^+$) 566.2; Calculated 565.3 for C$_{39}$H$_{39}$N$_3$O.

shown in scheme 14. AS shown, the primary amine of compound 11 can then be functionalized as desired utilizing known, conventional methods to generate amines, amides 12, ureas 13, and the like, as appreciated by those skilled in the art.

Specific Methods for Scheme 14

7,8-diphenyl-1H-furo[2,3-b]pyrazolo[3,4-d]pyridin-3-amine (11)

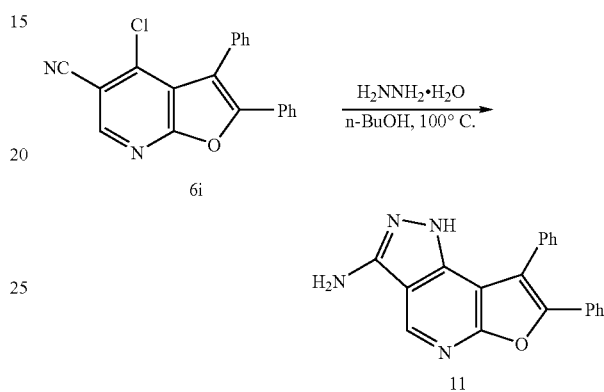

Scheme 14:
General Method for Synthesis of R$^5$ and R$^6$ fused N-containing Heterocycles

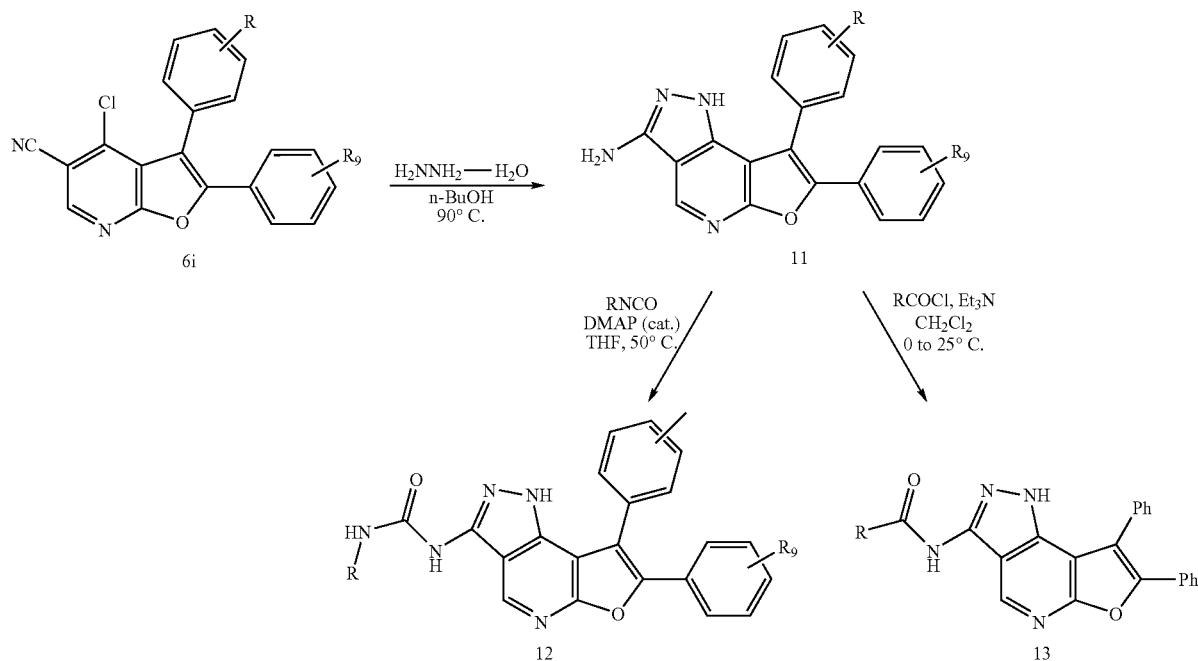

4-Chloro-5-cyano-furanopyridines 6i can be treated with hydrazine in a suitable solvent, such as an alcohol, to generate the nitrogen-containing-pyridyl fused ring systems 11, as To a mixture of 6i (30 mg, 0.091 mmol, 1.0 equiv) in n-BUOH (3 mL) was added hydrazine hydrate (ca. 0.2 mL). After heating at 100° C. for 12 hrs, the solvent was removed in vacuo. The resulting solid was recrystallized from n-BUOH to afford pyrazole 11. MS (MH⁺) 327.1; Calculated 326.1 for $C_{20}H_{14}N_4O$.

N-(7,8-diphenyl-1H-furo[2,3-b]pyrazolo[3,4-d]pyridin-3-yl)-N'-ethylurea (12a)

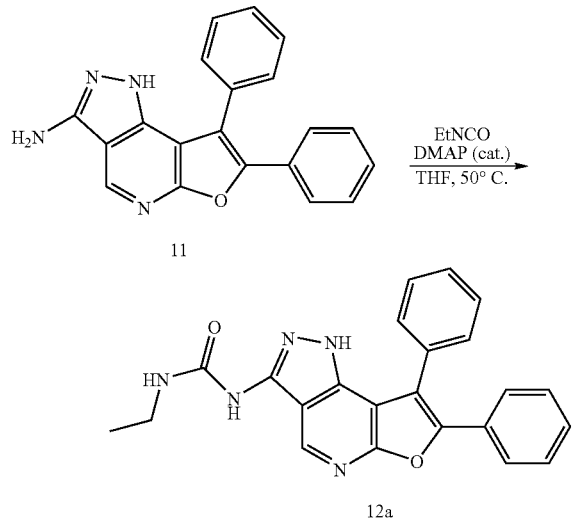

To a solution of 11 (22 mg, 0.068 mmol, 1.0 equiv) in THF (2 mL) was added 4-(Dimethylamino)pyridine (1 mg, 0.008 mmol, 0.1 equiv) and ethyl isocyanate (53 μL, 0.675 mmol, 10.0 equiv). After heating at 50° C. for 2 hrs, the solvent was removed in vacuo. The resulting yellow residue was purified by silica gel chromatography (5% MeOH:CH₂Cl₂) to afford urea 12a. MS (MH⁺) 398.4; Calculated 397.2 for $C_{23}H_{19}N_5O_2$.

N-(7,8-diphenyl-1H-furo[2,3-b]pyrazolo[3,4-d]pyridin-3-yl)acetamide (13) and 7-methyl-1,2-diphenyl-furo[3",2":5',6']pyrido[4',3':3,4]pyrazolo[1,5-a]pyrimidin-9(11H)-one (14)

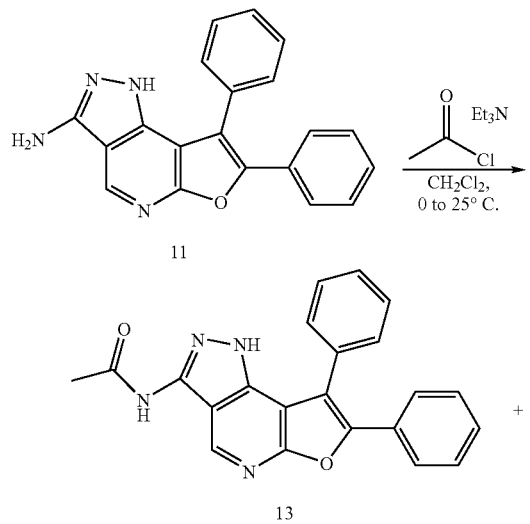

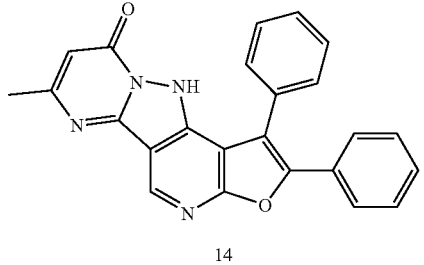

To a solution of 11 (57 mg, 0.175 mmol, 1.0 equiv) and triethylamine (244 μL, 1.75 mmol, 10.0 equiv) in CH₂Cl₂ at 0° C., was added acetyl chloride (37 μL, 0.525 mmol, 3.0 equiv). The solution was allowed to warm to ambient temperature. After 48 h the solvent was removed in vacuo and the resulting residue was purified by silica gel chromatography (5% MeOH:CH₂Cl₂) to afford amine 13 (MS (MH⁺) 369.1; Calculated 368.1 for $C_{22}H_{16}N_4O_2$) and amine 5 (MS (MH⁺) 393.1; Calculated 392.1 for $C_{24}H_{16}N_4O_2$). Fused ring systems such as compound 14 above are also within the scope of the present invention.

Scheme 15:
General Method for Synthesis of Amino-R¹ groups with various phenyl-substituted R³ and R⁵ groups on compounds of Formula I

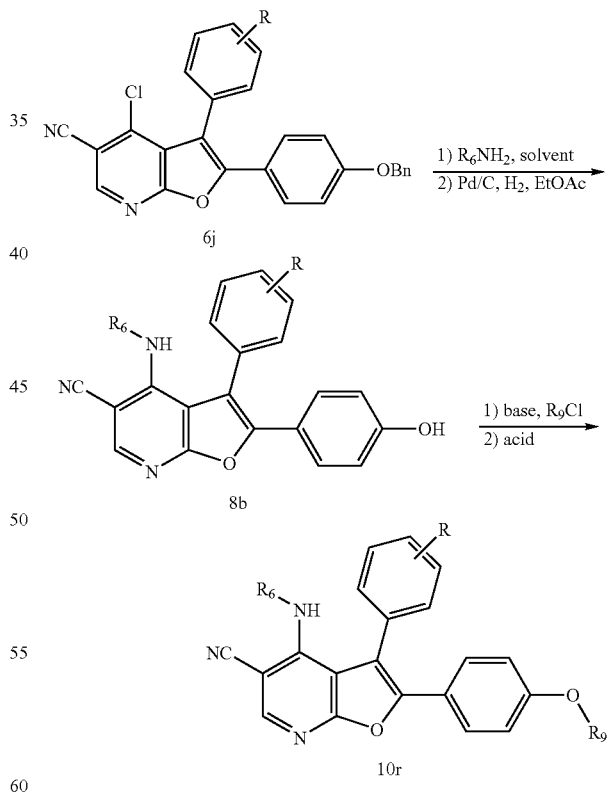

5-cyano-4-R⁶amino-3-phenyl-2-phenylsubstituted furanopyridines 10r can be made by the general route illustrated in scheme 15 as follows. Utilizing methods described herein, the 4-chlorofuranopyridine can be reacted with a suitable R⁶-amine and displaced to generate the 4-amino substituent. The benzyl group can be removed to afford compound 8b and the resulting alcohol can be reacted with desirable electrophiles, mitsunobu chemistry, and otherwise functionalized as desired utilizing known, conventional chemistry. The following specific methods exemplify one possibility of preparing a compound 10r (designated as 10t) as shown above.

Specific Methods for Scheme 15 tert-butyl 4-(2-(2-(4-(benzyloxy)phenyl)-5-cyano-3-phenylfuro[2,3-b]pyridin-4-ylamino)ethyl)piperazine-1-carboxylate (8c)

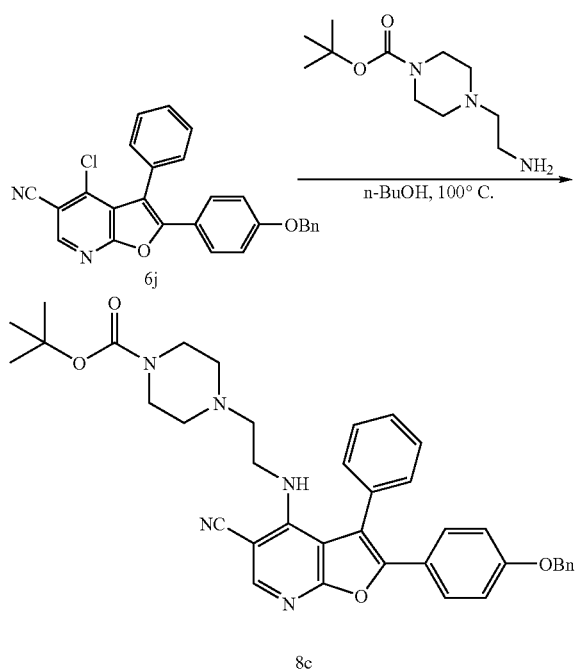

To a mixture of 6j (0.812 g, 1.86 mmol, 1.0 equiv) in n-BuOH (30 mL) was added tert-butyl-4-(2-aminoethyl)piperazine-1-carboxylate (2.80 g, 13.0 mmol, 7.0 equiv). After heating at 100° C. for 24 hrs, the solvent was removed in vacuo. The resulting residue was purified by silica gel chromatography (5% MeOH:CH$_2$Cl$_2$) to afford carbamate 8c. MS (MH$^+$) 630.1; Calculated 629.3 for C$_{38}$H$_{39}$N$_5$O$_4$.

tert-butyl 4-(2-(5-cyano-2-(4-hydroxyphenyl)-3-phenylfuro[2,3-b]pyridin-4-ylamino)ethyl)piperazine-1-carboxylate (3)

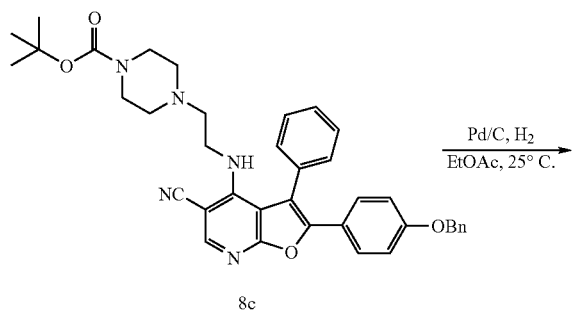

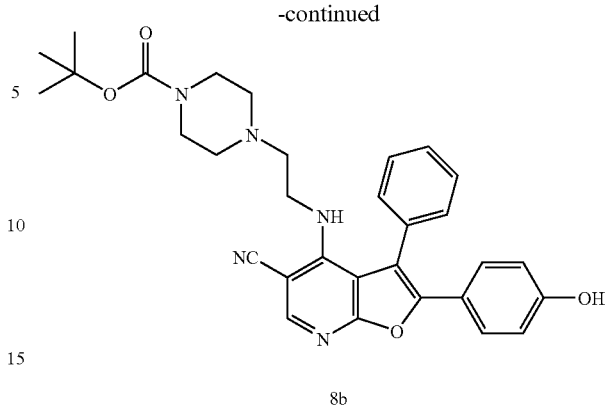

A mixture of 8c (200 mg, 0.303 mmol, 1.0 equiv) and 10% Pd on carbon (30 mg) in EtOAc at 25° C. was exposed to a hydrogen atmosphere (balloon). Upon consumption of the starting material as indicated by TCL, the mixture was filtered and solvent removed in vacuo. The resulting phenol 8b was advanced without further purification. MS (MH$^+$) 540; Calculated 539.3 for C$_{31}$H$_{33}$N$_5$O$_4$.

1,1-dimethylethyl 4-(2-((5-cyano-3-phenyl-2-(4-((2-(1-pyrrolidinyl)ethyl)oxy)phenyl)furo[2,3-b]pyridin-4-yl)amino)ethyl)-1-piperazinecarboxylate (8b)

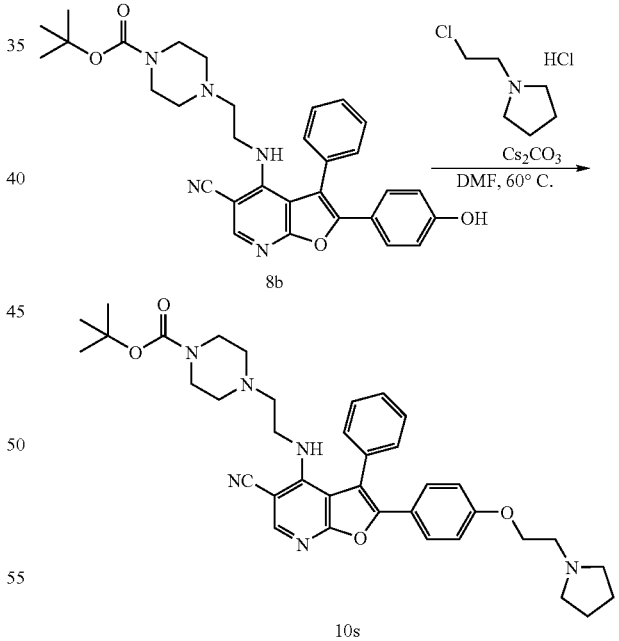

To a mixture of phenol 8b (114 mg, 2.12 mmol, 1.0 equiv) and 1-(2-chloroethyl)pyrrolidine hydrochloride (40 mg, 2.33 mmol, 1.1 equiv) in DMF (7 mL) was added cesium carbonate (345 mg, 1.06 mmol, 5.0 equiv). The mixture was heated at 60° C. After 24 hr, the solvent was removed in vacuo. The resulting residue was taken up in CH$_2$Cl$_2$ (25 mL), washed with brine, and dried with MgSO$_4$. After concentration under reduced pressure, the resulting residue was purified by silica gel chromatography (5% MeOH:CH$_2$Cl$_2$) to afford amine 10s. MS (MH$^+$) 637.3; Calculated 636.3 for C$_{38}$H$_{39}$N$_5$O$_4$.

3-phenyl-4-((2-(1-piperazinyl)ethyl)amino)-2-(4-((2-(1-pyrrolidinyl)ethyl)oxy)phenyl)furo[2,3-b]pyridine-5-carbonitrile (5)

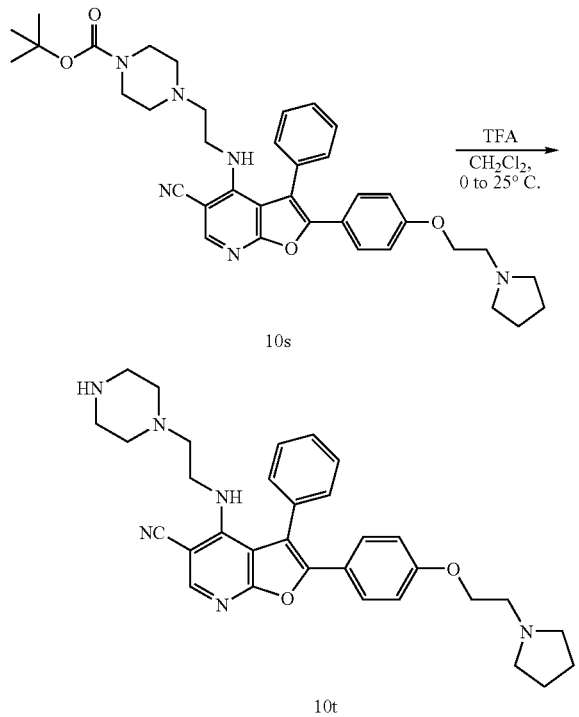

To solution of 10s (66 mg, 0.104 mmol, 1.0 equiv) in CH$_2$Cl$_2$ (3.0 mL) at 0° C. was added trifluoroacetic acid (0.5 mL). After 5 min, the solution was allowed to warm to ambient temperature and stirred for an additional 2 hr. The solution was diluted with CH$_2$Cl$_2$ (20 mL), washed with sat'd aqueous NaHCO$_3$ (ca. 20 mL), and dried with MgSO$_4$. After concentration in vacuo, amine 10t was obtained. MS (MH$^+$) 537.0; Calculated 536.3 for C$_{32}$H$_{36}$N$_6$O$_2$.

Scheme 16:
General Method for Synthesis of Amino-R$^1$ groups with various phenyl-substituted R$^3$ group on compounds of Formula I

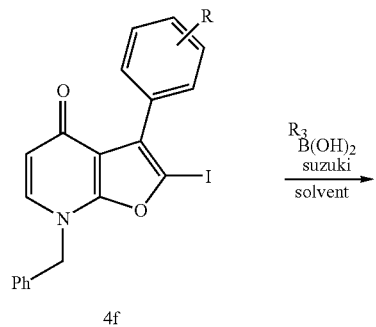

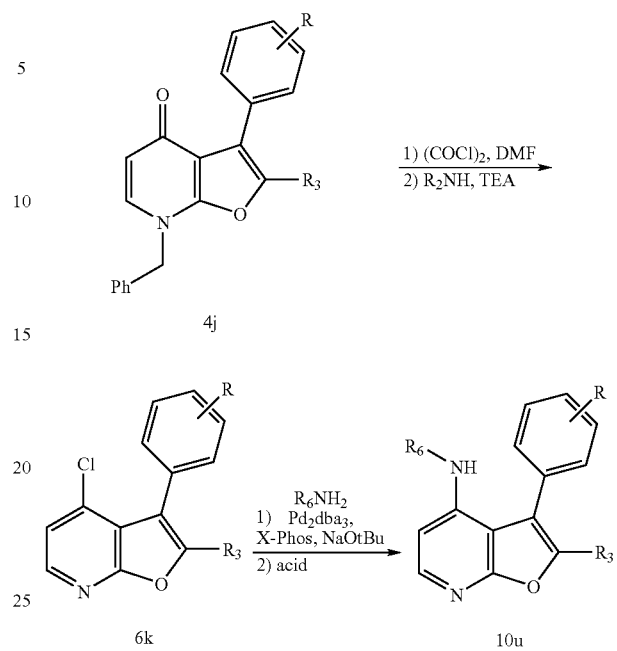

R$^3$ substituents on the furanopyridines of Formula I can be made via the route generally described in scheme 16, as follows. Utilizing the 3-iodo furanopyridine 4f, previously described, one can use Suzuki-type reaction conditions with desirable boronic acids to effect desirable R$^3$ group substitutions. This works particularly well with aryl boronic acids, as appreciated by those skilled in the art. Then, the R$^3$ adduct 4j can be transformed into the 4-chloro adduct 6k followed by displacement with suitable nucleophiles, such as amines as shown and previously described, to afford compounds 10u. The following specific methods exemplify one possibility of preparing a compound 10r (designated as 10v) as shown above.

Specific Methods for Scheme 16

3-(7-benzyl-4-oxo-3-phenyl-4,7-dihydrofuro[2,3-b]pyridin-2-yl)benzoic acid (4k)

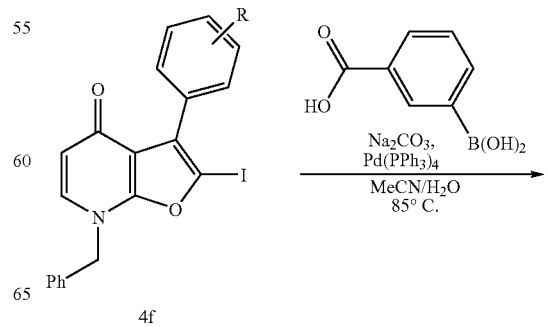

-continued

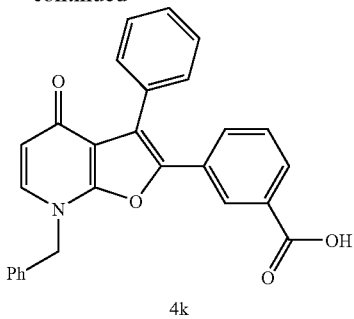
4k

To a mixture of iodide 4f (2.94 g, 6.89 mmol, 1.0 equiv), 3-carboxyphenylboronic acid (1.26 g, 7.57 mmol, 1.1 equiv), tetrakis(triphenylphosphine)palladium (0.796 g, 0.689 mmol, 0.1 equiv), and sodium carbonate (2.92 g, 27.6 mmol, 4.0 equiv), was added MeCN (30 mL) and $H_2O$ (30 mL). The slurry was heated at 85° C. for 8 h. After cooling to rt, EtOAc (ca. 100 mL) and $H_2O$ (ca. 50 mL) were added. The aqueous layer was separated, filtered, and acidified with 1N HCl. The resulting white precipitate was filtered to provide acid 4k. MS (MH$^+$) 422; Calculated 421.1 for $C_{27}H_{19}NO_4$.

(3-(4-chloro-3-phenylfuro[2,3-b]pyridin-2-yl)phenyl)(4-methylpiperazin-1-yl)methanone (61)

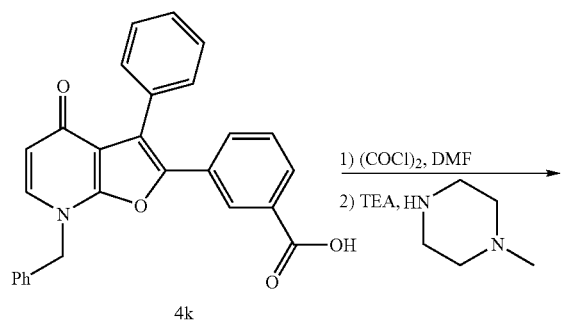

To a mixture of acid 4k (2.42 g, 5.75 mmol, 1.0 equiv) in CHCl$_3$ (30 mL) was added oxalyl chloride (2.5 mL, 28.7 mmol, 5.0 equiv) followed by DMF (ca. 40 μL). The mixture was heated to 65° C. After 3 hr, the solvent was removed in vacuo and the resulting residue was taken up in $CH_2Cl_2$ (20 mL). 1-Methylpiperazine (1.3 mL, 11.5 mmol, 2.0 equiv) was added followed by Et$_3$N (0.80 mL, 5.75 mmol, 1.0 equiv) and the solution was stirred at ambient temperature for 3 h. The solution was diluted with $CH_2Cl_2$ (20 mL) and washed with $H_2O$ and brine. After drying with MgSO$_4$ and concentration in vacuo, the residue was purified by silica gel chromatography (5% MeOH:$CH_2Cl_2$) to provide chloride 61. MS (MH$^+$) 432; Calculated 431.1 for $C_{25}H_{22}ClN_3O_2$.

Tert-butyl 4-(2-(2-(3-(1-methylpiperazine-4-carbonyl)phenyl)-3-phenylfuro[2,3-b]pyridin-4-ylamino)ethyl)piperazine-1-carboxylate (10v) and 2-(3-((4-methyl-1-piperazinyl)carbonyl)phenyl)-3-phenylfuro[2,3-b]pyridine (15)

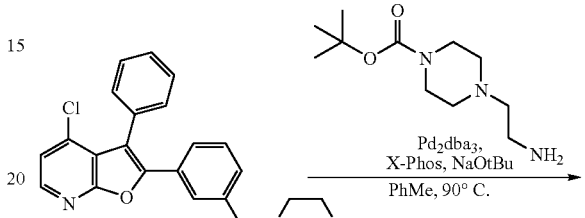
61

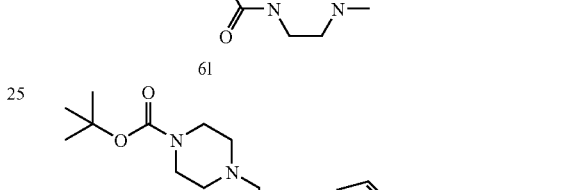
10v

+

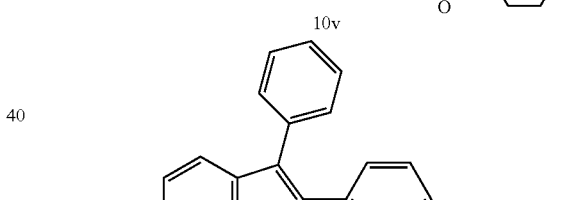
15

To a mixture of 61 (131 mg, 0.303 mmol, 1.0 equiv), Pd$_2$dba$_3$ (27 mg, 0.0303 mmol, 0.10 equiv), 2-Dicyclohexylphosphino-2',4',6'-tri-1-propyl-1,1'-biphenyl (17 mg, 0.036 mmol, 0.12 equiv), and NaOtBu (58 mg, 0.606 mmol, 2.0 equiv) was added toluene (5 mL) which was first purged with argon. After 1 min of vigorous stirring, tert-butyl 4-(2-aminoethyl)piperazine-1-carboxylate (63 μL, 0.606 mmol, 2.0 equiv) was added and the mixture was heated to 90° C. After starting material was consumed as indicated by TLC, the solvent was removed in vacuo. The resulting residue was taken up in EtOAc (50 mL) and washed with water and brine. After drying with MgSO$_4$ and concentration in vacuo, the crude mixture was purified by silica gel chromatography (10% MeOH:$CH_2Cl_2$) to afford amine 10v [MS (MH$^+$) 625; Calculated 624.3 for $C_{36}H_{44}N_6O_4$] and amine 15 [MS (MH$^+$) 398; Calculated 397.2 for $C_{25}H_{23}N_3O_2$].

(4-methylpiperazin-1-yl)(3-(3-phenyl-4-(2-(piperazin-1-yl)ethylamino)furo[2,3-b]pyridin-2-yl)phenyl)methanone (6)

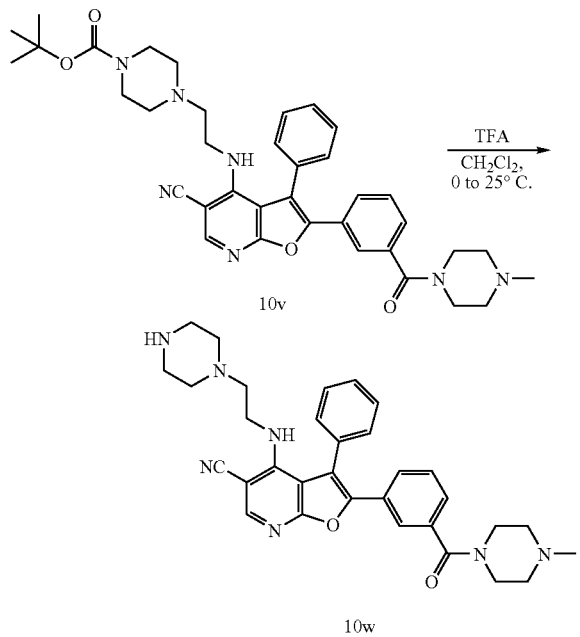

To solution of 10v (60 mg, 0.096 mmol, 1.0 equiv) in CH$_2$Cl$_2$ (5.0 mL) at 0° C. was added trifluoroacetic acid (0.8 mL). After 5 min, the solution was allowed to warm to ambient temperature and stirred for an additional 2 hr. The solution was diluted with CH$_2$Cl$_2$ (20 mL), washed with saturated aqueous NaHCO$_3$ (ca. 20 mL), and dried with MgSO$_4$. After concentration in vacuo and purification by silica gel chromatography (10:1:0.2 CH2Cl2:MeOH:NH$_4$OH), amine 10w was obtained. MS (MH$^+$) 525.2; Calculated 524.3 for C$_{31}$H$_{36}$N$_6$O$_2$.

Scheme 17:
Alternative Method for Synthesis for 2,3-diphenyl-substituted 4-amino furanopyridines

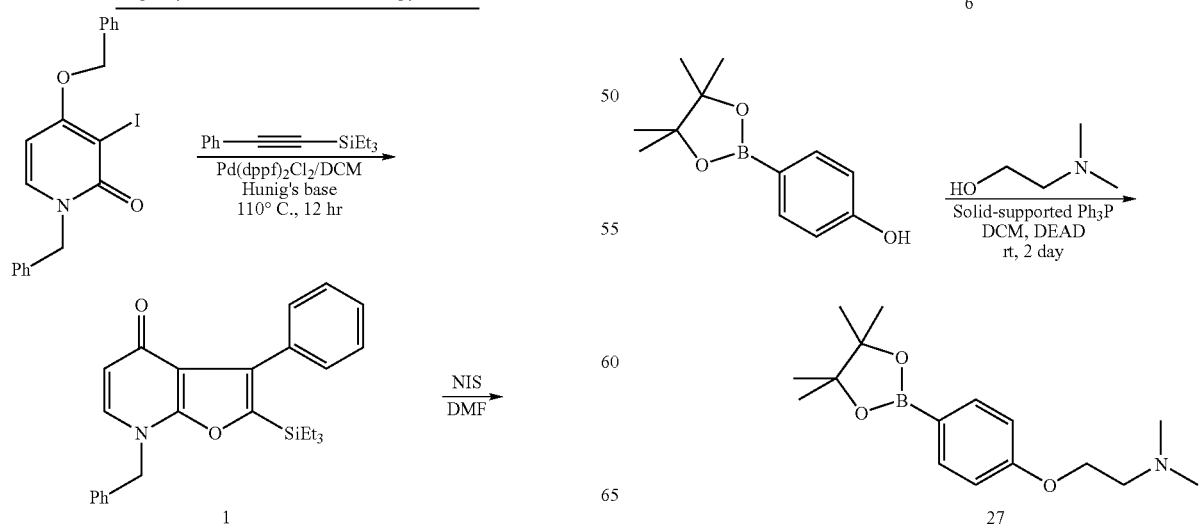

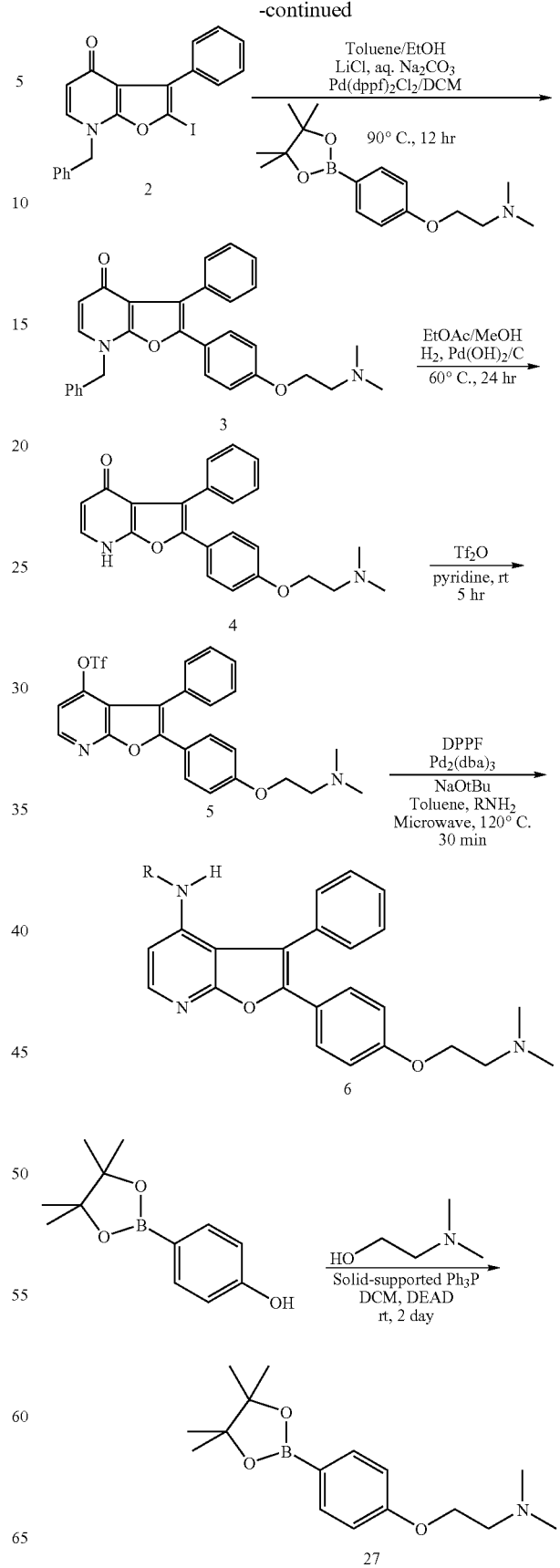

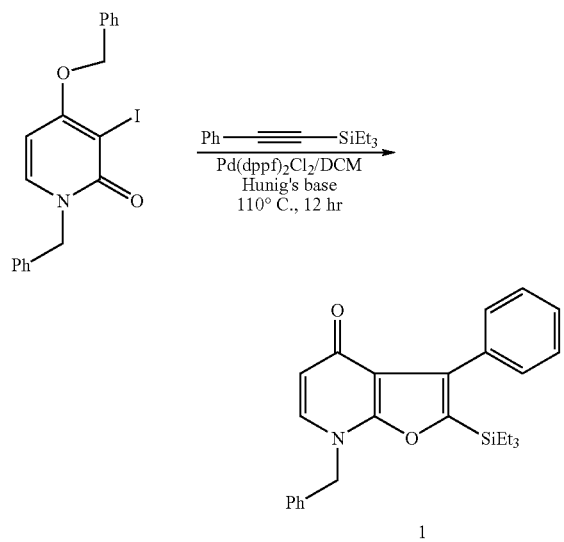

7-Benzyl-3-phenyl-2-(triethylsilyl)furo[2,3-b]pyridine-4(7H)-one (1)

A 250-ml round bottom flask was charged with 1-benzyl-4-benzyloxy-3-iodo-2-pyridone (6.00 g, 14.40 mmol), dichloro[1,1-bis(diphenylphosphino)ferrocene]palladium (II) dichloromethane adduct (1.18 g, 1.44 mmol), DMF (60 mL), Hunig's base (3 mL, 17.30 mmol), triethylsilyl phenylacetylene (9.34 g, 43.10 mmol). The system was evacuated and purged with $N_2$ three times, and the reaction was stirred at 110° C. for 12 hrs. The reaction mixture was diluted with EtOAc and washed with water. The organic layer was dried over $Na_2SO_4$ and the solvent was removed. The residue was purified by silica gel column chromatography, eluting with 50/50/1, EtOAc/Hexane/MeOH, to give 7-benzyl-3-phenyl-2-(triethylsily)furo[2,3-b]pyridine-4(7H)-one as a solid. MS (MH$^+$) 416.0; Calculated 415 for $C_{26}H_{29}NO_2Si$.

The procedure for the transformation of 1 to 2 is similar to that of scheme 6, previously described herein.

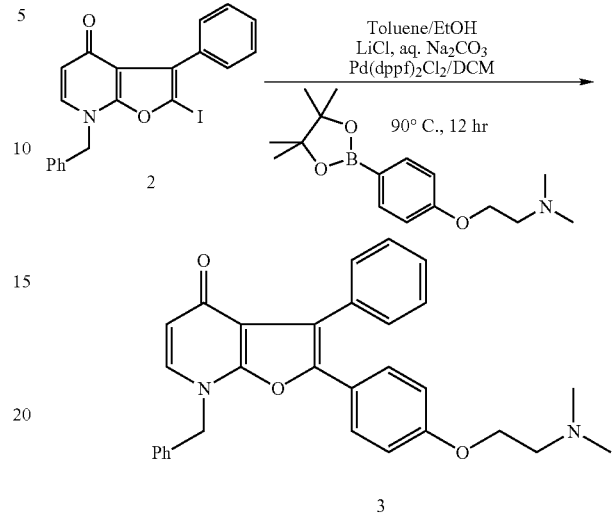

7-Benzyl-2-[4-(2-dimethylamino)ethoxy]phenyl-3-phenyl-7H-furo[2,3-b]pyidine-4-one (3)

A 250-ml round bottom flask was charged with 7-benzyl-2-iodo-3-phenylfuro[2,3-b]pyridine-4(7H)-one (2.47 g, 5.74 mmol), LiCl (1.17 g, 28.00 mmol), dichloro[1,1'-bis(diphenylphosphino)ferrocene]palladium(II) dichloromethane adduct (1.17 g, 1.44 mmol), 4-dimethylaminoethoxylphenyl boronic acid, pinacol ester (2.17 g, 7.46 mmol), $Na_2CO_3$ (8.56 ml, 2M in water), toluene (60 ml) and ethanol (60 mL). The reaction mixture was purged with $N_2$ and stirred at 90° C. for 12 hr. The reaction mixture was concentrated and the residue was dissolved in dichloromethane. This solution was washed with water and dried over $Na_2SO_4$. The solvent was removed and the residue was purified by silica gel column chromatography, eluting with 90:10:1, DCM/MeOH/ammonia in water 28-30%, to give the title compound as a solid. MS (MH$^+$) 465.1; Calculated 464 for $C_{30}H_{28}N_2O_3$.

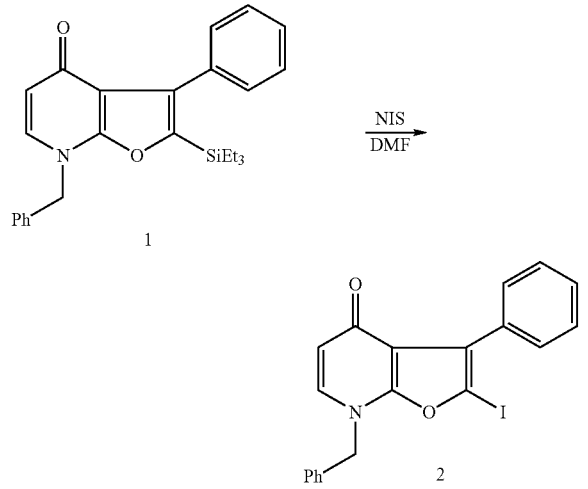

2-[4-(2-Dimethylamino)ethoxy]phenyl-3-phenyl-7H-furo[2,3-b]pyidine-4-one (4)

A 250-mL round bottom flask equipped with a condenser and hydrogen balloon was charged with 7-benzyl-2-[4-(2-dimethylamino)ethoxyl]phenyl-3-phenyl-7H-furo[2,3-b]pyidine-4-one (0.15 g, 0.31 mmol), EtOAc (15 mL), EtOH (15 mL) and activated palladium hydroxide (0.15 g, 20 wt % on carbon). The system was evacuated and purged with hydrogen three times. The reaction mixture was stirred at 60° C. for 24 hr, and then filtered. The solvent was removed, and the residue was purified by silica gel column chromatography (eluting with 90:10:0.5, DCM/MeOH/ammonia in water 28-30%) to give 2-[4-(2-dimethylamino)ethoxy]phenyl-3-phenyl-7H-furo[2,3-b]pyidine-4-one as a pale solid. MS (MH$^+$) 375.2; Calculated 374 for $C_{23}H_{22}N_2O_3$.

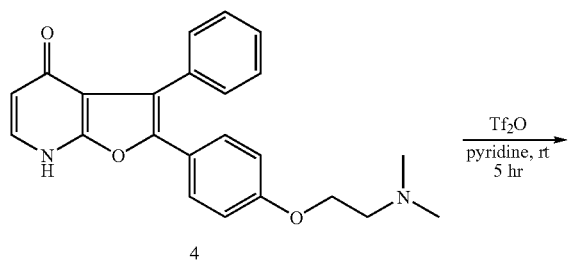

2-[4-(2-Dimethylamino)ethoxy]phenyl-3-phenyl-4-trifluoromethanesufonate-7-azabenzo[b]furan (5)

To a solution of 2-[4-(2-dimethylamino)ethoxy]phenyl-3-phenyl-7H-furo[2,3-b]pyidine-4-one (0.29 g, 0.78 mmol) in pyridine (15 mL) was added trifluoromethanesulfonic anhydride (196 μL, 1.16 mmol) dropwise at 0° C. via a syringe. The reaction was warmed up to room temperature and stirred for 5 hr. The reaction mixture was dissolved in DCM and washed with water. The organic layer was dried over $Na_2SO_4$, and concentrated to give the product, as a brown solid. MS (MH$^+$) 507.1; Calculated 506 for $C_{24}H_{21}F_3N_2O_5S$.

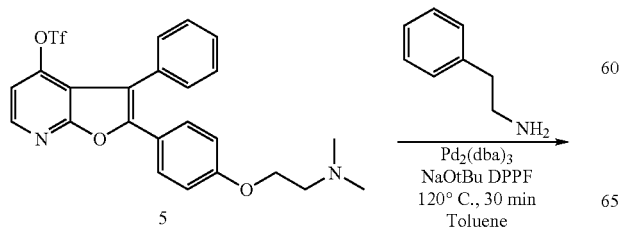

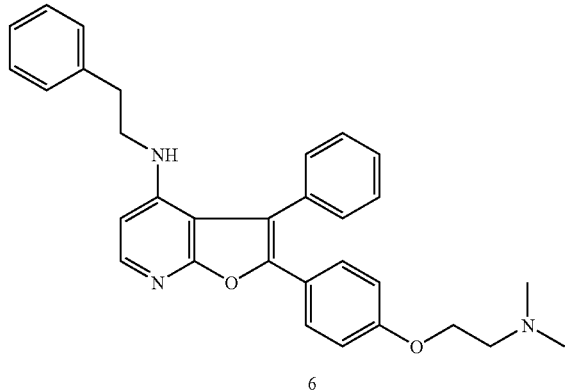

2-[4-(2-Dimethylamino)ethoxy]phenyl-3-phenyl-4-(2-phenylethyl)amino-7-azabenzo[b]furan (6)

A 10-ml microwave tube was charged with DPPF (3.6 mg, 0.007 mmol), Pd$_2$(dba)$_3$ (1.8 mg, 0.002 mmol), NaOtBu (12.0 mg, 0.12 mmol), toluene (2.5 mL), 2-phenylethylamine (0.060 mL, 0.48 mmol) and 2-[4-(2-dimethylamino)ethoxyl]phenyl-3-phenyl-4-trifluoromethanesufonate-7-azabenzo[b]furan (4.3 mg, 0.066 mmol). The system was sealed, evacuated and purged with N$_2$ three times. The reaction was heated in the microwave oven to 120° C. for 30 min. The solvent was removed and the residue was re-dissolved in DMSO. Preparative HPLC purification gives 2-[4-(2-dimethylamino)ethoxy]phenyl-3-phenyl-4-(2-phenylethyl)amino-7-azabenzo[b]furan as a white powder. MS (MH$^+$) 478.3; Calculated 477 for $C_{31}H_{31}N_3O_2$.

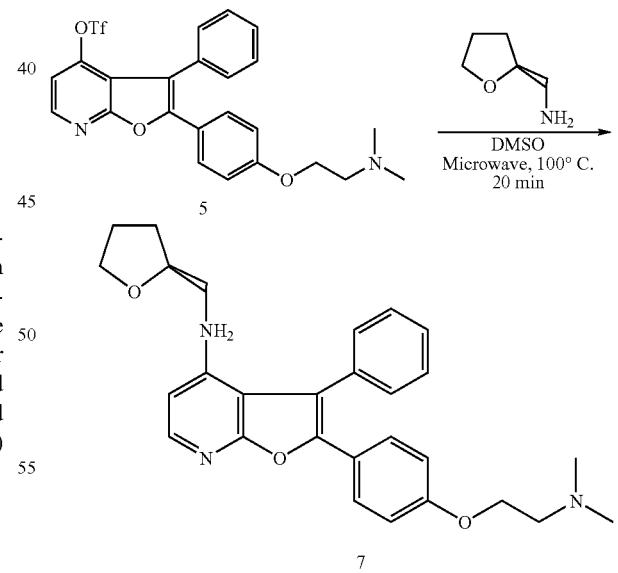

2-[4-(2-Dimethylamino)ethoxy]phenyl-3-phenyl-4-(s)-(+)-tetrahydrofurylamino-7-azabenzo[b]furan (7)

A 10-ml microwave tube was charged with 2-[4-(2-dimethylamino)ethoxy]phenyl-3-phenyl-4-trifluoromethanesufonate-7-azabenzo[b]furan (0.11 g, 0.21 mmol), (s)-(+)-tetrahydrofurylamine (0.18 mL, 1.72 mmol) and DMSO (2 mL). The tube was sealed and the reaction was heated in the microwave oven to 100° C. for 20 min. The reaction mixture was purified using preparative HPLC to give 2-[4-(2-dimethylamino)ethoxyl]phenyl-3-phenyl-4-(s)-(+)-tetrahydrofurylamino-7-azabenzo[b]furan as a pale solid. MS (MH$^+$) 458.2; Calculated 457 for $C_{28}H_{31}N_3O_3$.

The following compounds were made by a method similar to the one described in scheme 17.

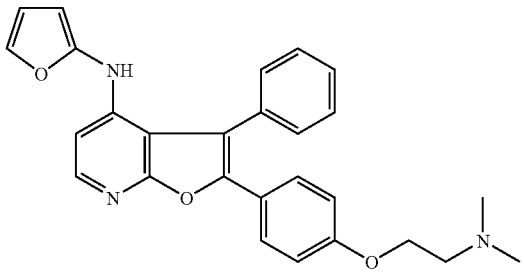

2-[4-(2-Dimethylamino)ethoxy]phenyl-3-phenyl-4-furfurylamino-7-azabenzo[b]furan (8)

MS (MH$^+$) 454.2; Calculated for $C_{28}H_{27}N_3O_3$.

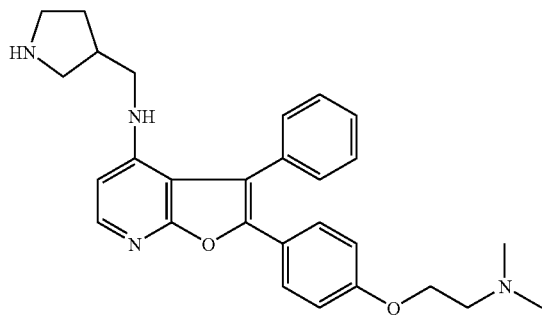

2-[4-(2-Dimethylamino)ethoxy]phenyl-3-phenyl-4-(3-pyrrolidyl)methylamino-7-azabenzo[b]furan (9)

MS (MH$^+$) 457.3; Calculated 456.6 for $C_{28}H_{32}N_4O_2$.

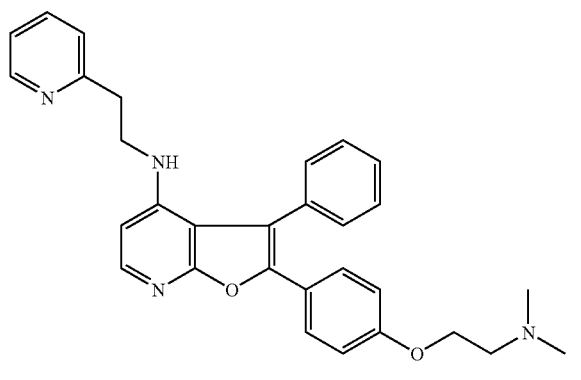

2-[4-(2-Dimethylamino)ethoxy]phenyl-3-phenyl-4-[2-(2-pyridyl)ethyl]amino-7-azabenzo[b]furan (10)

MS (MH$^+$) 479.2; Calculated 478.6 for $C_{30}H_{30}N_4O_2$.

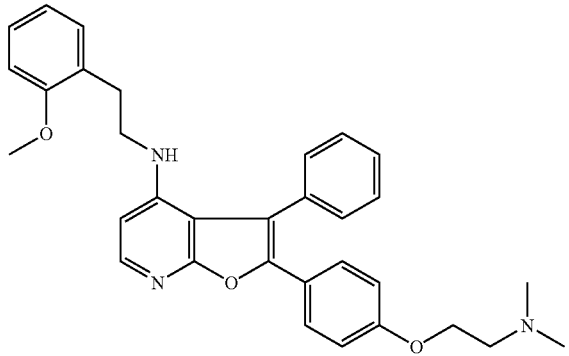

2-[4-(2-Dimethylamino)ethoxy]phenyl-3-phenyl-4-[2-(2-methoxyphenyl)ethyl]amino-7-azabenzo[b]furan (11)

MS (MH$^+$) 508.3; Calculated 507.6 for $C_{32}H_{33}N_3O_3$.

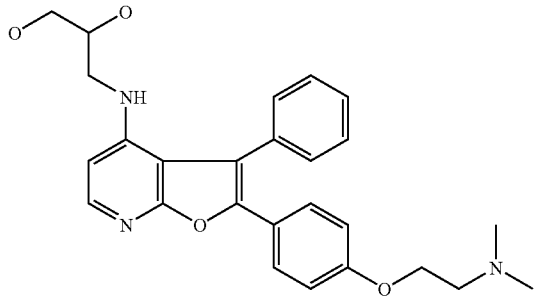

2-[4-(2-Dimethylamino)ethoxy]phenyl-3-phenyl-4-(2,3-dihydroxy)propylamino-7-azabenzo[b]furan (12)

MS (MH$^+$) 448.2; Calculated 447.5 for $C_{26}H_{29}N_3O_4$.

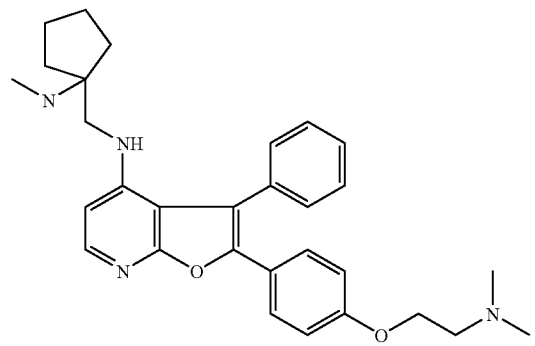

2-[4-(2-Dimethylamino)ethoxy]phenyl-3-phenyl-4-(1-methylamino)cyclopentylmethylamino-7-azabenzo[b]furan (13)

MS (MH$^+$) 485.4; Calculated 484.6 for $C_{30}H_{36}N_4O_2$.

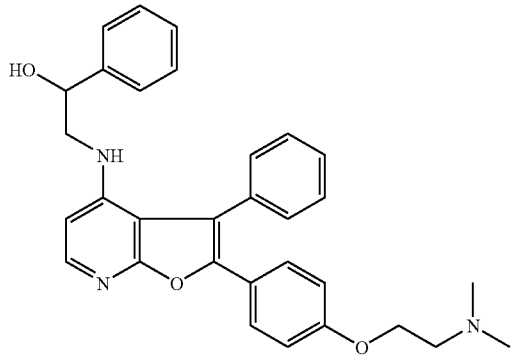

2-[4-(2-Dimethylamino)ethoxy]phenyl-3-phenyl-4-(2-hydroxy-2-phenylethyl)amino-7-azabenzo[b]furan (14)

MS (MH$^+$) 494.2; Calculated 493.6 for $C_{31}H_{31}N_3O_3$.

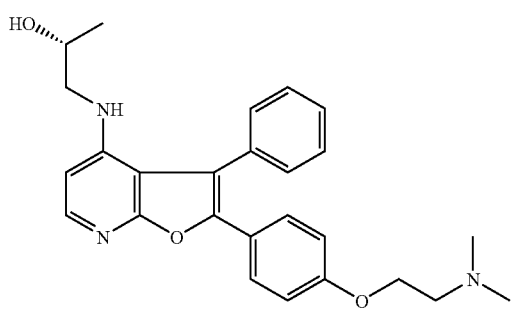

2-[4-(2-Dimethylamino)ethoxy]phenyl-3-phenyl-4-[2-(R)-hydroxypropyl]amino-7-azabenzo[b]furan (15)

MS (MH$^+$) 432.2; Calculated 431.5 for $C_{26}H_{29}N_3O_3$.

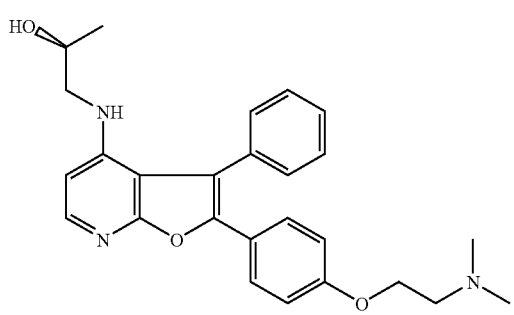

2-[4-(2-Dimethylamino)ethoxy]phenyl-3-phenyl-4-[2-(S)-hydroxypropyl]amino-7-azabenzo[b]furan (16)

MS (MH$^+$) 432.2; Calculated 431.5 for $C_{26}H_{29}N_3O_3$.

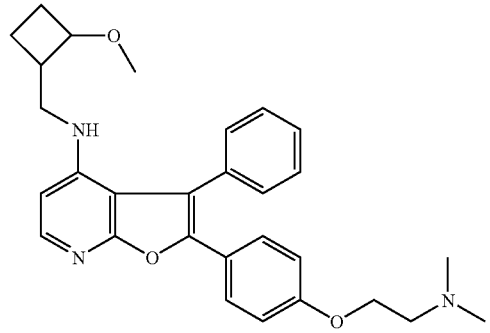

2-[4-(2-Dimethylamino)ethoxy]phenyl-3-phenyl-4-(2-methoxycyclobutylmethyl)amino-7-azabenzo[b]furan (17)

MS (MH$^+$) 472.3; Calculated 471.6 for $C_{29}H_{33}N_3O_3$.

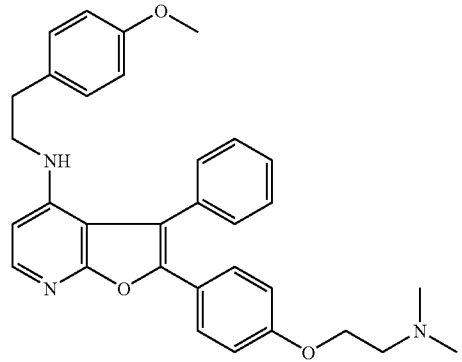

2-[4-(2-Dimethylamino)ethoxy]phenyl-3-phenyl-4-[2-(4-methoxyphenyl)ethyl]amino-7-azabenzo[b]furan (18)

MS (MH$^+$) 508.3; Calculated 507.6 for $C_{32}H_{33}N_3O_3$.

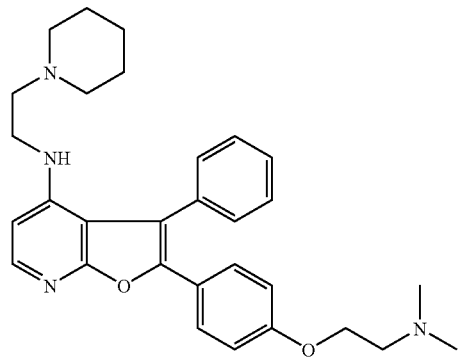

87

2-[4-(2-Dimethylamino)ethoxy]phenyl-3-phenyl-4-(2-piperidinoethyl)amino-7-azabenzo[b]furan (19)

MS (MH$^+$) 485.2; Calculated 484.6 for $C_{30}H_{36}N_4O_2$.

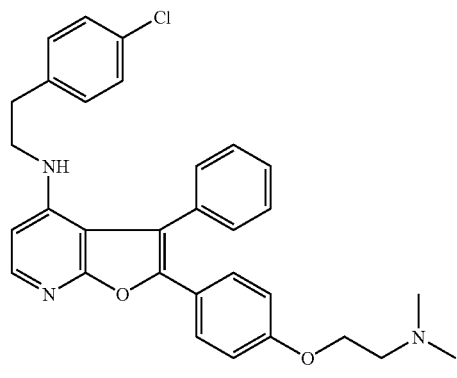

2-[4-(2-Dimethylamino)ethoxy]phenyl-3-phenyl-4-[2-(4-chlorophenyl)ethyl]amino-7-azabenzo[b]furan (20)

MS (MH$^+$) 512.2; Calculated 512.0 for $C_{31}H_{30}ClN_3O_2$.

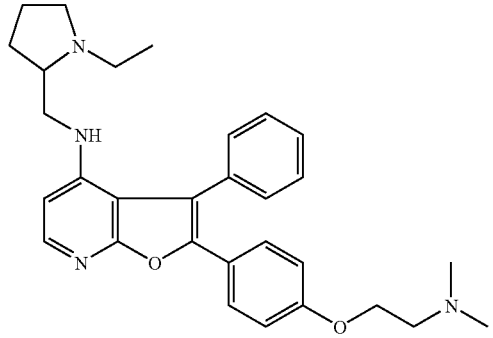

2-[4-(2-Dimethylamino)ethoxy]phenyl-3-phenyl-4-[2-(N-ethyl)pyrrolidyl)methylamino-7-azabenzo[b]furan (21)

MS (MH$^+$) 485.4; Calculated 484.6 for $C_{30}H_{36}N_4O_2$.

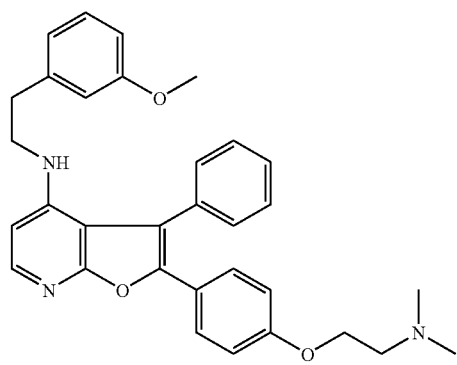

88

2-[4-(2-Dimethylamino)ethoxy]phenyl-3-phenyl-4-[2-(3-methoxyphenyl)ethyl]amino-7-azabenzo[b]furan (22)

MS (MH$^+$) 508.3; Calculated 507.6 for $C_{32}H_{33}N_3O_3$.

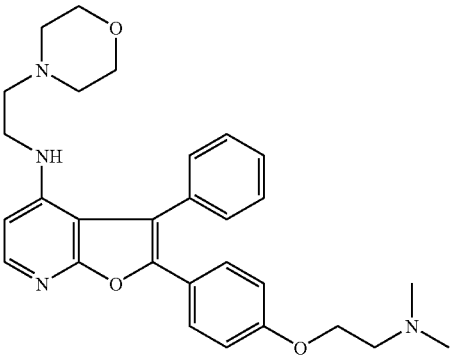

2-[4-(2-Dimethylamino)ethoxy]phenyl-3-phenyl-4-(2-mnorpholino)ethylamino-7-azabenzo[b]furan (23)

MS (MH$^+$) 487.3; Calculated 486.6 for $C_{29}H_{34}N_4O_3$.

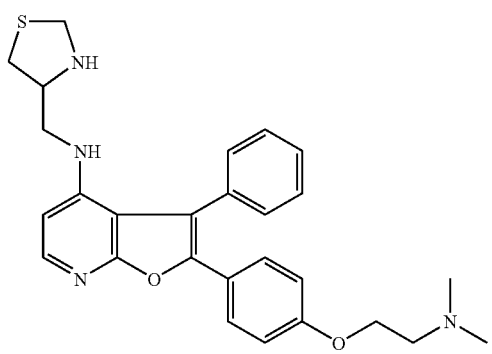

2-[4-(2-Dimethylamino)ethoxy]phenyl-3-phenyl-4-(3-thiazolidyl)methylamino-7-azabenzo[b]furan (24)

MS (MH$^+$) 475.1; Calculated 474.6 for $C_{27}H_{30}N_4O_2S$.

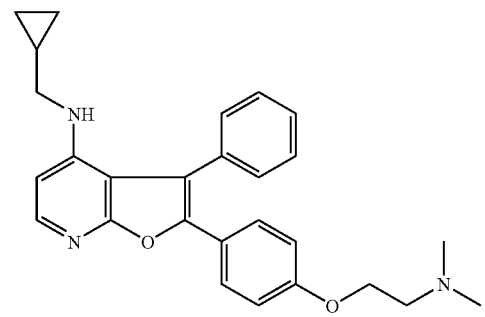

2-[4-(2-Dimethylamino)ethoxy]phenyl-3-phenyl-4-cycopropylmethylamino-7-azabenzo[b]furan (25)

MS (MH$^+$) 428.2; Calculated 427.5 for $C_{27}H_{29}N_3O_2$.

Scheme 18:
Method for the Synthesis of 2-[4-(2-Dimethylamino)ethoxy] phenyl-3-phenyl-4-(1,3-dithiolan-2-yl)methylamino-7-azabenzo[b]furan (26)

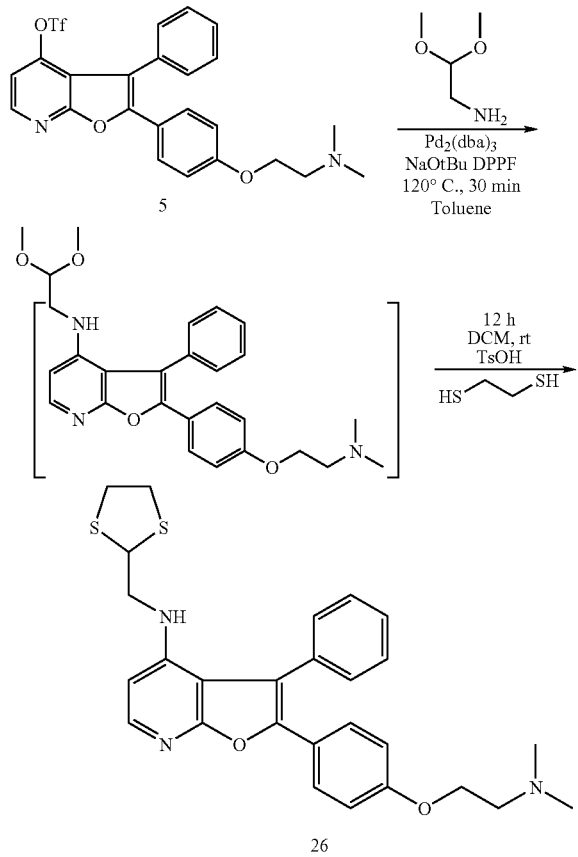

A 10-ml microwave tube was charged with DPPF (3.6 mg, 0.007 mmol), Pd$_2$(dba)$_3$ (1.8 mg, 0.002 mmol), NaOtBu (12.0 mg, 0.120 mmol), toluene (2.5 mL), aminoacetaldehyde dimethyl acetal (0.036 mL, 0.330 mmol) and 2-[4-(2-dimethylamino)ethoxyl]phenyl-3-phenyl-4-trifluoromethanesufonate-7-azabenzo[b]furan (43.0 mg, 0.066 mmol). The system was sealed, evacuated and purged with N$_2$ three times. The reaction was heated in the microwave oven to 120° C. for 30 min. The solvent was removed and the residue was dissolved in DCM (2 mL) and then treated with TsOH (10.0 mg, 0.057 mmol) for 12 hr at room temperature. The reaction mixture was purified using preparative HPLC to afford 2-[4-(2-dimethylamino)ethoxy]phenyl-3-phenyl-4-(1,3-dithiolan-2-yl)methylamino-7-azabenzo[b]furan as a pale powder. MS (MH$^+$) 492.1; Calculated 491.6 for $C_{27}H_{29}N_3O_2S_2$.

Scheme 19:
Method for the Synthesis of 4-Dimethylaminoetoxyphenyl boronic acid, pinacol ester (27)

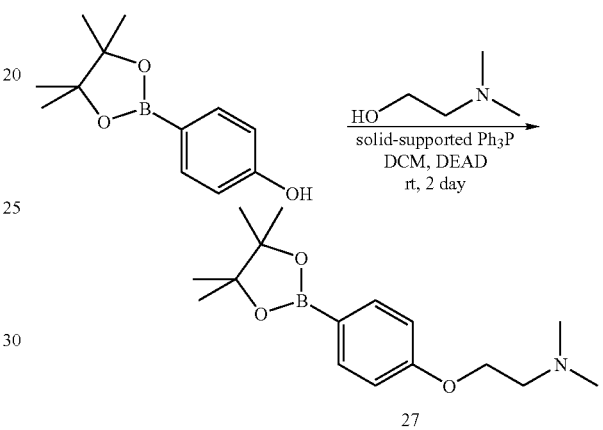

To a suspension of solid-supported triphenylphosphine (30.0 g, 30.0 mmol) in DCM (150 mL) was added DEAD (3.93 mL, 25.0 mmol) dropwise via a syringe at room temperature. The reaction mixture was stirred for 1 hr, and then a solution of 4-(4,4,5,5-tetramethyl-1,3,2-dioxaborolan-2-yl)phenol (4.40 g, 20.0 mmol) and 2-(dimethylamino) ethanol (2.01 mL, 20.0 mmol) in DCM (30 mL) was introduced. The reaction mixture was stirred at room temperature for 2 days. The mixture was filtered and the filtrate was concentrated. The residue was purified by silica gel column chromatography (eluting with 95:5, DCM/MeOH) to afford 4-dimethylaminoethoxyphenyl boronic acid, pinacol ester (2.25 g) as an yellow oil. MS (MH$^+$) 292.4; Calculated 29 for $C_{16}H_{26}BNO_3$ Scheme 20:
Method for Synthesis of 2,3-diphenyl-substituted, 4-mino-substituted, 5-substituted furanopyridines

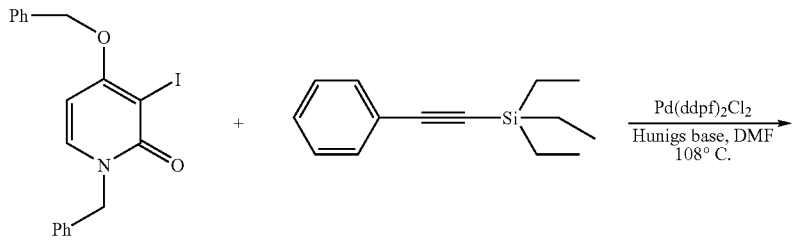

-continued
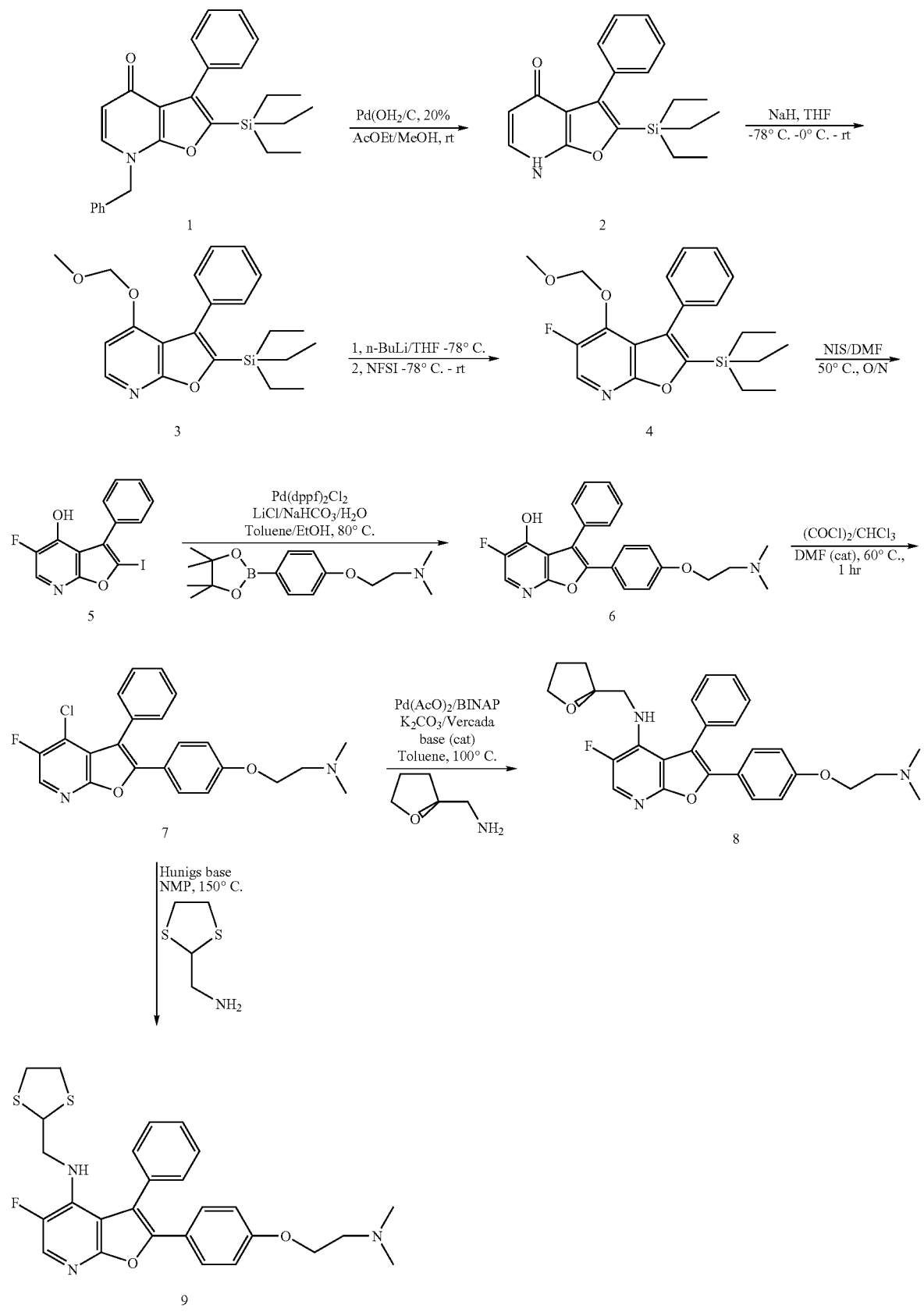

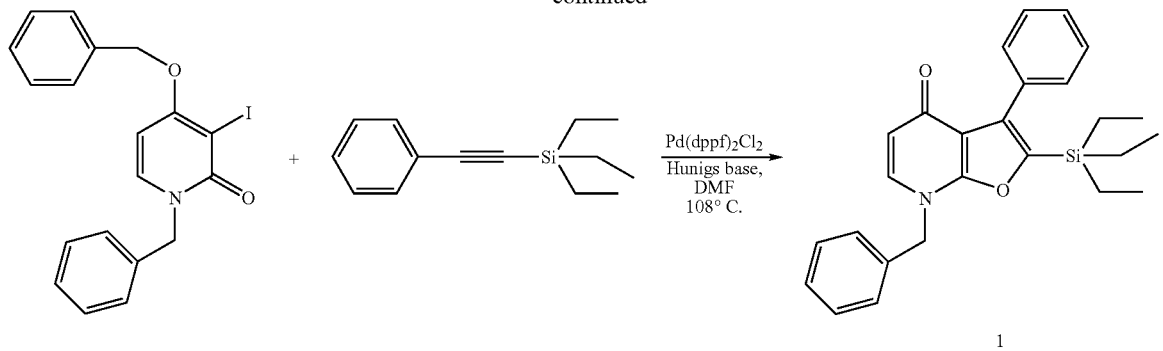

7-Benzyl-3-phenyl-2-(triethylsilanyl)-7H-furo[2,3-b]pyridin-4-one (1)

To a solution of 1-benzyl-4-benzyloxy-3-iodo-1H-pyridin-2-one (1.00 g, 2.40 mmol), diisopropylethylamine, (0.51 mL. 2.88 mmol) and Pd(dppf)$_2$Cl$_2$/CH$_2$Cl$_2$ (0.20 g, 0.24 mmol) in DMF (10.0 mL) was slowly added 1-phenyl-2-(triethylsilyl)acetylene (1.50 g, 7.20 mmol) at room temperature under N$_2$. The resulting reaction mixture was degassed and stirred at 108° C. under nitrogen overnight. The reaction was cooled down to room temperature, and the solvent was removed. The residue was dissolved in DCM (250 mL). The solution was washed with NaHCO$_3$ (30×2 mL) and brine (30 mL). The organic layer was dried over MgSO$_4$ and concentrated. The residue was purified by silica gel column chromatography, eluting with ethyl acetate/methanol/100/1, to give the title compound. MS (m/z), M+H$^+$ 416.2.

3-Phenyl-2-(triethylsilanyl)-7H-furo-[2,3-b]pyridin-4-one (2)

A mixture of 7-benzyl-3-phenyl-2-(triethylsilanyl)-7H-furo[2,3-b]pyridin-4-one (1) and Pd(OH)$_2$ (0.11 g 20% on C, 0.11 mmol) in ethyl acetate (10 mL) and methanol (10 mL) was degassed and stirred under hydrogen at room temperature for 2.5 hr. The catalyst was filtered off and the solvent was removed to give the title compound. MS (m/z), M+H$^+$ 326.0.

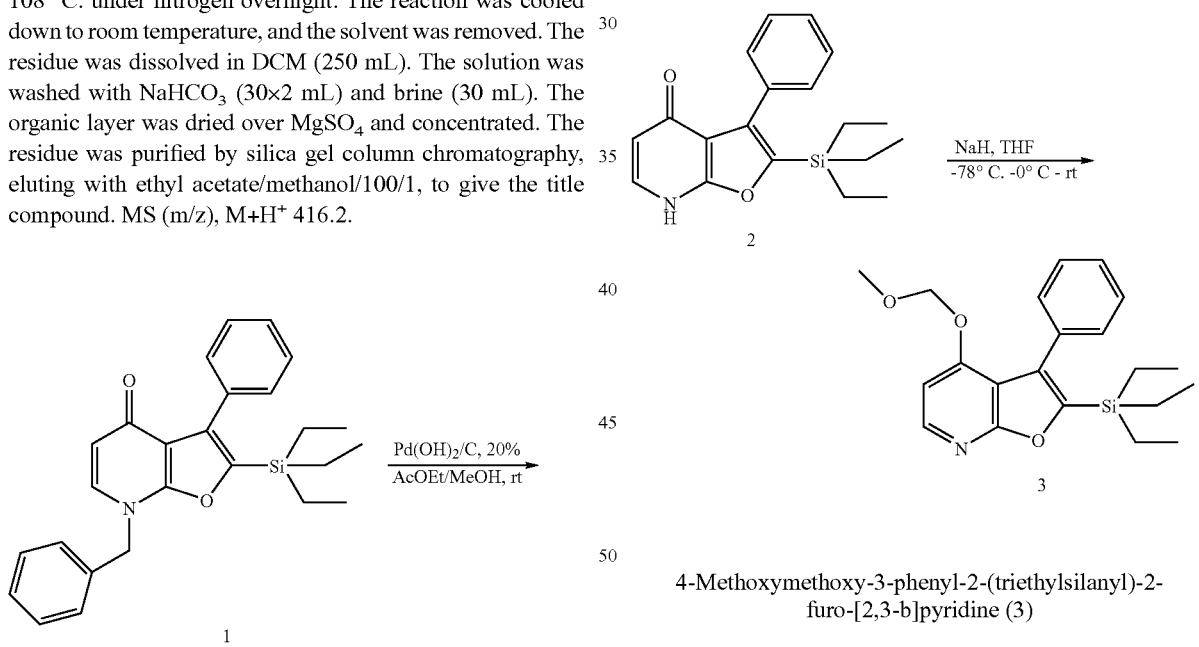

4-Methoxymethoxy-3-phenyl-2-(triethylsilanyl)-2-furo-[2,3-b]pyridine (3)

To a suspension of NaH (0.15g, 60% in mineral oil, 3.69 mmol) in THF (12.0 mL) was slowly added 3-phenyl-2-(triethylsilanyl)-7H-furo-[2,3-b]pyridin-4-one (2) (1.00 g, 3.10 mmol) in THF (2.0 mL) at −78° C., and then the reaction mixture was stirred at room temperature for 1 hr. MOMCl (0.30 g, 3.69 mmol) in THF (2.0 mL) was slowly added during 45 min. The resulting mixture was stirred for an additional 2 hr. Ethyl acetate was added and the mixture was washed with NaHCO$_3$ (25.0 mL) and brine (20×2 mL) and then dried over MgSO$_4$. The solvent was evaporated and the residue was purified by silica gel column chromatography, eluting with ethyl acetate/hexane, 1/1, to give the title compound. MS (m/z), M+H$^+$ 370.3.

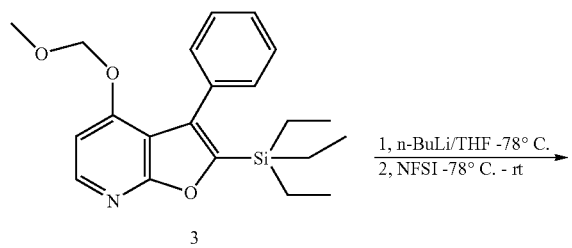

5-Fluoro-4-methoxymethoxy-3-phenyl-2-(triethylsilanyl)-furo[2,3-b]pyridine (4)

To a solution of 4-methoxymethoxy-3-phenyl-2-(triethylsilanyl)-2-furo-[2,3-b]pyridine (3) (0.40 g, 1.08 mmol) in THF (3.0 mL) was slowly added n-BuLi (0.52 mL, 2.5 M in hexane) at −78° C. under $N_2$. The resulting mixture was stirred at −78° C. for 35 min., then N-fluorosulfonimide, NFSI (0.51 g, 1.30 mmol) in THF (3.0 mL) was added at −78° C. The reaction mixture was allowed to stir for another 20 min and then the temperature of the reaction was allowed to rise to room temperature and the mixture was stirred at an additional 2 hr. Ethyl acetate (100.0 mL) was added and the resulting solution was washed with sat. acqueous $NaHCO_3$ solution (25.0 mL) and brine (20.0 mL). The combined organic layers were dried over $MgSO_4$, filtered and the filtrate was concentrated. The residue was purified by silica gel column chromatography, eluting with ethyl acetate/hexane, 3/7, to give the title compound. MS (m/z), M+H⁺ 388.1.

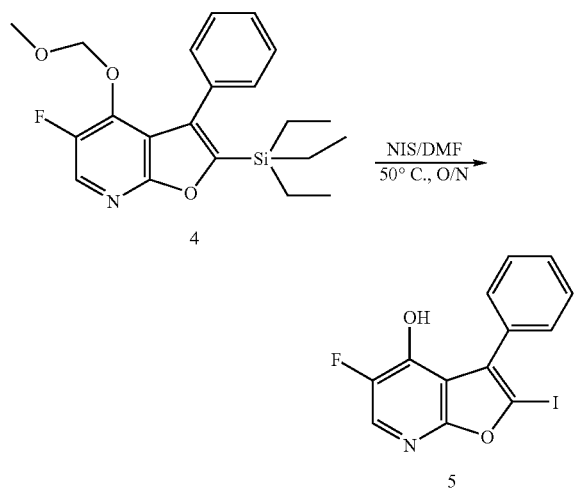

5-Fluoro-2-iodo-3-phenyl-furo[2,3-b]pyridin-4-ol (5)

The mixture of 5-fluoro-4-methoxymethoxy-3-phenyl-2-(triethylsilanyl)-furo[2,3-b]pyridine (4) (0.10 g, 0.26 mmol) and NIS (0.07 g, 0.31 mmol) in DMF (1.5 mL) was stirred at 50° C. overnight. The reaction mixture was purified by preparative HPLC to give the title compound 5.
MS (m/z), M+H⁺ 355.9.

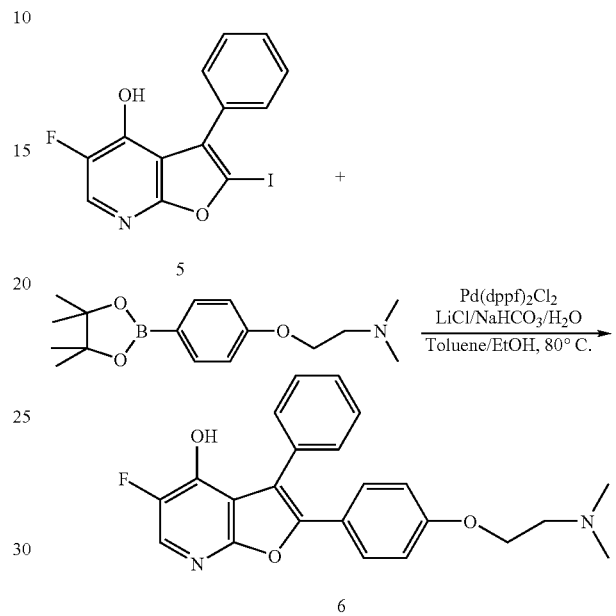

2-[4-(2-Dimethylaminoethoxy)-phenyl]-5-fluoro-3-phenyl-furo[2,3-b]pyridin-4-ol (6)

The mixture of 5-fluoro-2-iodo-3-phenyl-furo[2,3-b]pyridin-4-ol (5) (90.0 mg, 0.24, mmol), dimethyl-(2-[4-(4,4,5,5-tetramethyl-(1,3,2)dioxaborolan-2-yl)-phenoxy]-ethyl)-amine (114.0 mg, 0.39 mmol), LiCl (33.1 mg, 0.78 mmol), Pd(dppf)₂Cl₂ DCM (24.5 mg, 0.03 mmol) and Na₂CO₃ (0.33 mL, 2.0 M in water, 0.65 mmol) was degassed and heated to 80° C. with stirring under nitrogen for 5 h. The solvent was removed. The residue was purified by preparative HPLC to give the title compound. MS (m/z), M+H⁺ 393.2.

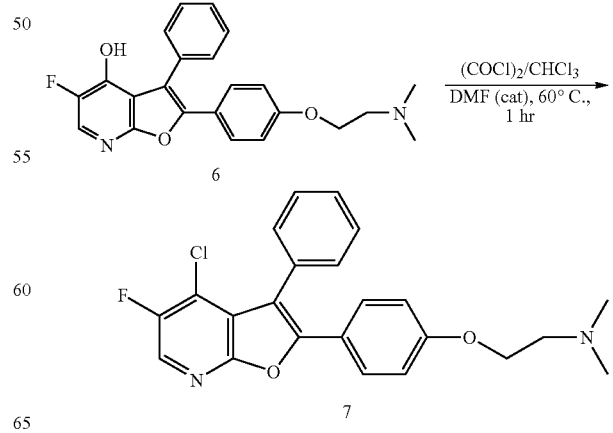

(2-[4-(4-Chloro-5-fluoro-3-phenyl-furo[2,3-b]pyridin-2-yl)-phenoxy]ethyl)dimehtylamine (7)

The mixture of 2-[4-(2-dimethylaminoethoxy)-phenyl]-5-fluoro-3-phenyl-furo[2,3-b]pyridin-4-ol (6) (121.0 mg, 0.31 mmol) and oxalyl chloride (196.0 mg, 1.54 mmol) in chloroform (3.0 mL) was stirred at 60° C. for 1 hr. The solvent was removed, and the residue was purified by preparative HPLC to give the title compound. MS (m/z), M+H⁺ 411.1.

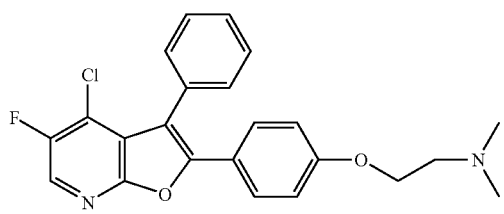

7

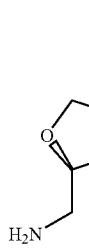

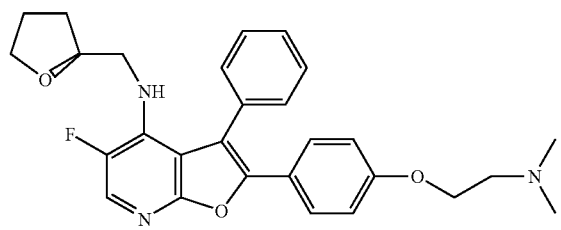

8

(S)-{2-[4-(2-Dimethylaminoethoxy)-phenyl]-5-fluoro-3-phenyl-furo[2,3-b]pyridin-4-yl}-[tetrahydrofuran-2-ylmethyl]-amine (8)

The mixture of (2-[4-(4-chloro-5-fluoro-3-phenyl-furo[2,3-b]pyridin-2-yl)-phenoxy]-ethyl)-dimehtylamine (7) (10.0 mg, 0.024 mmol), (S)-(tetrahydrofuran-2-yl)-methylamine (5.0 mg, 0.048 mmol), Pd(OAc)₂ (1.0 mg, 0.003 mmol), BINAP (2.0 mg, 0.003 mmol), K₂CO₃ (3.3 mg, 0.024 mmol) and Vercada Base, 2,8,9-triisopropyl-2,5,8,9-tetraaza-1-phosphabicyclo[3,3,3]undecane (cat) in toluene (0.8 mL) was degassed three times and heated to 100° C. with stirring under N₂ for 3.5 h. The solvent was removed and the residue was purified by preparative HPLC to give the title compound. MS (m/z), M+H⁺ 476.2.

The following two compounds were made using a similar method as that describe above.

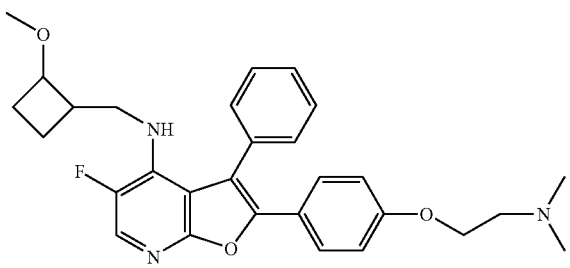

{2-[4-(2-Dimethylaminoethoxy)-phenyl]-5-fluoro-3-phenyl-furo[2,3-b]pyridin-4-yl}-(2-methoxycyclobutylmethyl)-amine (9)

MS (m/z), M+H⁺ 490.3.

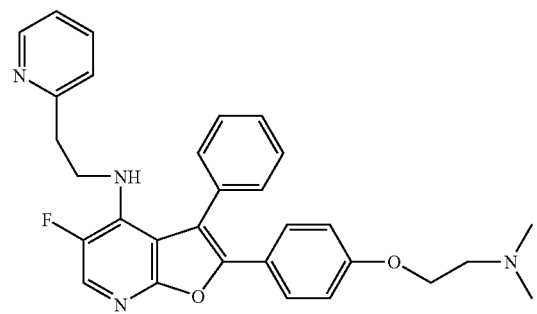

{2-[4-(2-Dimethylaminoethoxy)-phenyl]-5-fluoro-3-phenyl-furo[2,3-b]pyridin-4-yl}-(2-pyridin-2-yl-ethyl)-amine (10)

MS (m/z), M+H⁺ 497.2.

Scheme 21:
Method of Synthesis of amino dithiane R⁶ groups as R¹

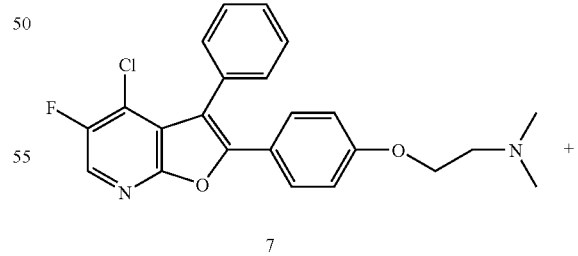

7

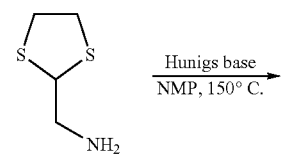

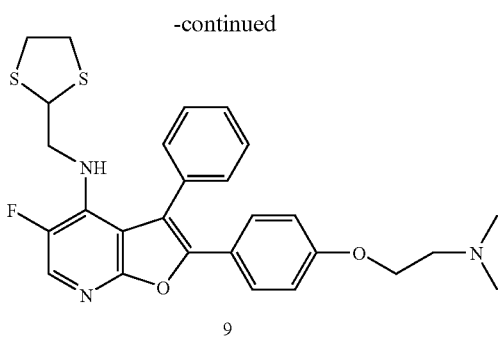

{2-[4-(2-Dimethylaminoethoxy)-phenyl]-5-fluoro-3-phenyl-furo[2,3-b]pyridin-4-yl}-[1,3]-dithiolan-2-ylmethylamine (9)

The mixture of (2-[4-(4-chloro-5-fluoro-3-phenyl-furo[2,3-b]pyridin-2-yl)-phenoxy]-ethyl)-dimehtylamine (7) (30.0 mg, 0.07 mmol), 1,3-dithiolan-2-methylamine (65.8 mg, 0.49 mmol) and diisopropylethylamine (63.0 mg, 0.49 mmol) in NMP (0.6 mL) was heated to 150° C. with stirring under $N_2$ overnight. The reaction mixture was purified by silica gel column chromatography, eluting with DCM/MeOH, 9/1, to give the title compound. MS (m/z), M+H$^+$ 510.0.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H$^+$ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include, for example, water, esters, typically lower alkyl-lower alkanoates, e.g EtOAc, ethers, typically aliphatic ethers, e.g. Et$_2$O, or cyclic ethers, e.g. THF, liquid aromatic hydrocarbons, typically benzene or toluene, alcohols, typically MeOH, EtOH, IpOH or 1-propanol, nitriles, typically AcCN, halogenated hydrocarbons, typically CH$_2$Cl$_2$, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples in the table below serve to illustrate various embodiments of the invention. The table also contains the method by which these examples were prepared, with respect to the various schemes presented above. The schematic illustrations, detailed method descriptions of the preparation of compounds of Formulas I, as well as the examples below and compounds described above fall within the scope, and serve to exemplify the scope of compounds contemplated in the invention. These detailed method descriptions are presented for illustrative purposes only and are not intended as a restriction on the scope of the invention.

| Ex. | Name | Mol. Wt. | MH+ | Scheme |
|---|---|---|---|---|
| 1 | 2,3-diphenyl-N-((2S)-tetrahydro-2-furanylmethyl)furo[2,3-b]pyridin-4-amine | 370.45 | 371 | 4, 5 |
| 2 | 2,3-diphenyl-N-(2-(1-piperazinyl)ethyl)furo[2,3-b]pyridin-4-amine | 398.507 | 399 | 4, 5 |
| 3 | 2-(4-((2-(4-morpholinyl)ethyl)oxy)phenyl)-3-phenyl-N-(2-(1-piperazinyl)ethyl)furo[2,3-b]pyridin-4-amine | 527.665 | 528 | 4, 5 |

-continued

| Ex. | Name | Mol. Wt. | MH+ | Scheme |
|---|---|---|---|---|
| 4 | N-(2-(4-morpholinyl)ethyl)-2-(4-((2-(4-morpholinyl)ethyl)oxy)phenyl)-3-phenylfuro[2,3-b]pyridin-4-amine | 528.649 | 529 | 4, 5 |
| 5 | 2,3-diphenyl-4-(((2S)-tetrahydro-2-furanylmethyl)amino)furo[2,3-b]pyridine-5-carbonitrile | 395.46 | 396 | 10, 11 |
| 6 | 3-phenyl-N-(2-(1-piperazinyl)ethyl)-2-(4-((2-(1-pyrrolidinyl)ethyl)oxy)phenyl)furo[2,3-b]pyridin-4-amine | 511.666 | 512 | 1, 2, 3 |
| 7 | 3-phenyl-N-(2-(1-piperazinyl)ethyl)-2-(4-((2-(1-piperidinyl)ethyl)oxy)phenyl)furo[2,3-b]pyridin-4-amine | 525.693 | 526 | 1, 2, 3 |
| 8 | 2,3-diphenyl-4-((2-(1-piperazinyl)ethyl)amino)furo[2,3-b]pyridine-5-carbonitrile | 423.517 | 424 | 10, 11 |
| 9 | 4-chloro-2,3-diphenyl-N-((2S)-tetrahydro-2-furanylmethyl)furo[2,3-b]pyridin-5-amine | 404.895 | 405 | 13 |
| 10 | 5-(aminomethyl)-2,3-diphenyl-N-(2-(1-piperazinyl)ethyl)furo[2,3-b]pyridin-4-amine | 427.549 | 428 | 10, 11 |
| 11 | 4-chloro-2,3-diphenyl-N-(2-(1-piperazinyl)ethyl)furo[2,3-b]pyridin-5-amine | 432.953 | 433 | 13 |
| 12 | N,N'-bis(4-(1,1-dimethylethyl)phenyl)-2,3-diphenylfuro[2,3-b]pyridine-4,5-diamine | 565.757 | 566 | 13 |
| 13 | 3-phenyl-N-(2-(1-piperazinyl)ethyl)-2-(4-((2-(1H-pyrrol-1-yl)ethyl)oxy)phenyl)furo[2,3-b]pyridin-4-amine | 507.635 | 508 | 1, 2, 3 |
| 14 | 2-(4-((2-(bis(1-methylethyl)amino)ethyl)oxy)phenyl)-3-phenyl-N-(2-(1-piperazinyl)ethyl)furo[2,3-b]pyridin-4-amine | 541.736 | 542 | 1, 2, 3 |
| 15 | 3-(4-((2-(4-morpholinyl)ethyl)oxy)phenyl)-2-phenyl-N-(2-(1-piperazinyl)ethyl)furo[2,3-b]pyridin-4-amine | 527.665 | 528 | 4, 5 |
| 16 | 2,3-diphenyl-4-((2-(2-pyridinyl)ethyl)amino)furo[2,3-b]pyridine-5-carbonitrile | 416.482 | 417 | 10, 11 |
| 17 | 2,3-diphenyl-4-((2-(3-pyridinyl)ethyl)amino)furo[2,3-b]pyridine-5-carbonitrile | 416.482 | 417 | 10, 11 |
| 18 | 4-(((3-methylphenyl)methyl)amino)-2,3-diphenylfuro[2,3-b]pyridine-5-carbonitrile | 415.494 | 416 | 10, 11 |
| 19 | 4-((1-methylethyl)amino)-2,3-diphenylfuro[2,3-b]pyridine-5-carbonitrile | 353.423 | 354 | 10, 11 |
| 20 | 2,3-diphenyl-4-((2-(1-pyrrolidinyl)ethyl)amino)furo[2,3-b]pyridine-5-carbonitrile | 408.503 | 409 | 10, 11 |
| 21 | 2,3-diphenyl-4-((2-(1-piperidinyl)ethyl)amino)furo[2,3-b]pyridine-5-carbonitrile | 422.529 | 423 | 10, 11 |
| 22 | 2,3-diphenyl-4-((1-(phenylmethyl)-4-piperidinyl)amino)furo[2,3-b]pyridine-5-carbonitrile | 484.6 | 485 | 10, 11 |
| 23 | 4-((1S)-2,3-dihydro-1H-inden-1-ylamino)-2,3-diphenylfuro[2,3-b]pyridine-5-carbonitrile | 427.505 | 428 | 10, 11 |
| 24 | 4-((2-((2S)-1-methyl-2-pyrrolidinyl)ethyl)amino)-2,3-diphenylfuro[2,3-b]pyridine-5-carbonitrile | 422.5295 | 423 | 10, 11 |
| 25 | 2,3-diphenyl-4-((2-(4-pyridinyl)ethyl)amino)furo[2,3-b]pyridine-5-carbonitrile | 416.482 | 417 | 10, 11 |
| 26 | 7,8-diphenyl-1H-furo[2,3-b]pyrazolo[3,4-d]pyridin-3-amine | 326.358 | 327 | 14 |
| 27 | 4-(((1R)-4-(diethylamino)-1-methylbutyl)amino)-2,3-diphenylfuro[2,3-b]pyridine-5-carbonitrile | 452.599 | 453 | 12 |
| 28 | 4-(4-(2-(diethylamino)ethyl)-1-piperazinyl)-2,3-diphenylfuro[2,3-b]pyridine-5-carbonitrile | 479.625 | 480 | 12 |
| 29 | 4-((4-(dimethylamino)butyl)amino)-2,3-diphenylfuro[2,3-b]pyridine-5-carbonitrile | 410.518 | 411 | 12 |
| 30 | 4-(4-(2-(1H-imidazol-1-yl)ethyl)-1-piperazinyl)-2,3-diphenylfuro[2,3-b]pyridine-5-carbonitrile | 474.565 | 475 | 12 |
| 31 | 3-phenyl-2-(4-((2-(1-piperidinyl)ethyl)oxy)phenyl)-N-(2-(4-pyridinyl)ethyl)furo[2,3-b]pyridin-4-amine | 518.658 | 519 | 9 |
| 32 | 2-(4-((2-(1H-imidazol-1-yl)ethyl)oxy)phenyl)-3-phenyl-N-(2-(1-piperazinyl)ethyl)furo[2,3-b]pyridin-4-amine | 508.623 | 509 | 1, 2, 3 |
| 33 | 4-((3-hydroxypropyl)amino)-2,3-diphenylfuro[2,3-b]pyridine-5-carbonitrile | 369.422 | 370 | 12 |
| 34 | 4-((2-(1H-imidazol-1-yl)ethyl)amino)-2,3-diphenylfuro[2,3-b]pyridine-5-carbonitrile | 405.459 | 406 | 12 |
| 35 | 4-amino-2,3-diphenylfuro[2,3-b]pyridine-5-carbonitrile | 311.343 | 312 | 12 |
| 36 | N-(3-(1H-imidazol-1-yl)propyl)-3-phenyl-2-(4-((2-(1-piperidinyl)ethyl)oxy)phenyl)furo[2,3-b]pyridin-4-amine | 521.661 | 428 | 9 |

-continued

| Ex. | Name | Mol. Wt. | MH+ | Scheme |
|---|---|---|---|---|
| 37 | N-(7,8-diphenyl-1H-furo[2,3-b]pyrazolo[3,4-d]pyridin-3-yl)acetamide | 368.394 | 369 | 14 |
| 38 | ethyl 1-(5-cyano-2,3-diphenylfuro[2,3-b]pyridin-4-yl)-4-piperidinecarboxylate | 451.523 | 452 | 12 |
| 39 | 3-phenyl-2-(4-((2-(1-piperidinyl)ethyl)oxy)phenyl)-N-(2-(3-pyridinyl)ethyl)furo[2,3-b]pyridin-4-amine | 518.658 | 519 | 9 |
| 40 | N~1~,N~1~-dimethyl-N~3~-(3-phenyl-2-(4-((2-(1-piperidinyl)ethyl)oxy)phenyl)furo[2,3-b]pyridin-4-yl)-1,3-propanediamine | 498.667 | 499 | 9 |
| 41 | 2-(4-(((1-methyl-3-piperidinyl)methyl)oxy)phenyl)-3-phenyl-N-(2-(1-piperazinyl)ethyl)furo[2,3-b]pyridin-4-amine | 525.693 | 526 | 1, 2, 3 |
| 42 | 4-((5-cyano-2,3-diphenylfuro[2,3-b]pyridin-4-yl)amino)butanoic acid | 397.432 | 398 | 12 |
| 43 | (2S)-4-((5-cyano-2,3-diphenylfuro[2,3-b]pyridin-4-yl)amino)-2-hydroxybutanoic acid | 413.431 | 414 | 12 |
| 44 | 1,1-dimethylethyl 4-(2-((5-cyano-3-phenyl-2-(4-((2-(1-pyrrolidinyl)ethyl)oxy)phenyl)furo[2,3-b]pyridin-4-yl)amino)ethyl)-1-piperazinecarboxylate | 636.793 | 637 | 15 |
| 45 | 3-phenyl-4-((2-(1-piperazinyl)ethyl)amino)-2-(4-((2-(1-pyrrolidinyl)ethyl)oxy)phenyl)furo[2,3-b]pyridine-5-carbonitrile | 536.676 | 537 | 15 |
| 46 | N-(7,8-diphenyl-1H-furo[2,3-b]pyrazolo[3,4-d]pyridin-3-yl)benzamide | 430.465 | 431 | 14 |
| 47 | 7-methyl-1,2-diphenylfuro[3",2":5',6']pyrido[4',3':3,4]pyrazolo[1,5-a]pyrimidin-9(11H)-one | 392.416 | 393 | 14 |
| 48 | 4-((2-(4-ethyl-1-piperazinyl)ethyl)amino)-2,3-diphenylfuro[2,3-b]pyridine-5-carbonitrile | 451.571 | 452 | 12 |
| 49 | 2-(4-((2-(methyloxy)ethyl)oxy)phenyl)-3-phenyl-N-(2-(1-piperazinyl)ethyl)furo[2,3-b]pyridin-4-amine | 472.586 | 473 | 1, 2, 3 |
| 50 | N-(7,8-diphenyl-1H-furo[2,3-b]pyrazolo[3,4-d]pyridin-3-yl)-N'-ethylurea | 397.436 | 398 | 14 |
| 51 | N-(1,1-dimethylethyl)-N'-(7,8-diphenyl-1H-furo[2,3-b]pyrazolo[3,4-d]pyridin-3-yl)urea | 425.49 | 426 | 14 |
| 52 | N-(1,2,2,6,6-pentamethyl-4-piperidinyl)-3-phenyl-2-(4-((2-(1-piperidinyl)ethyl)oxy)phenyl)furo[2,3-b]pyridin-4-amine | 566.785 | 567 | 9 |
| 53 | N-(2-(1-methyl-2-pyrrolidinyl)ethyl)-3-phenyl-2-(4-((2-(1-piperidinyl)ethyl)oxy)phenyl)furo[2,3-b]pyridin-4-amine | 524.705 | 525 | 9 |
| 54 | N-(2,6-dichlorophenyl)-N'-(7,8-diphenyl-1H-furo[2,3-b]pyrazolo[3,4-d]pyridin-3-yl)urea | 514.37 | 514 | 14 |
| 55 | 3-phenyl-N-(2-(1-piperazinyl)ethyl)-2-(3-pyridinyl)furo[2,3-b]pyridin-4-amine | 399.496 | 400 | 4, 5 |
| 56 | 1-(2-((4-(3-phenyl-4-(((2S)-tetrahydro-2-furanylmethyl)amino)furo[2,3-b]pyridin-2-yl)phenyl)oxy)ethyl)-2-pyrrolidinone | 497.592 | | 17 |
| 57 | 2-(4-(4-morpholinylcarbonyl)phenyl)-3-phenyl-N-((2S)-tetrahydro-2-furanylmethyl)furo[2,3-b]pyridin-4-amine | 483.565 | | 17 |
| 58 | N-(cyclopropylmethyl)-2-(4-((2-(dimethylamino)ethyl)oxy)phenyl)-3-phenylfuro[2,3-b]pyridin-4-amine | 427.545 | | 17 |
| 59 | 2-(4-((2-(dimethylamino)ethyl)oxy)phenyl)-N-(2-(4-morpholinyl)ethyl)-3-phenylfuro[2,3-b]pyridin-4-amine | 486.613 | | 17 |
| 60 | 2-(4-((2-(dimethylamino)ethyl)oxy)phenyl)-3-phenyl-N-(2-phenylethyl)furo[2,3-b]pyridin-4-amine | 477.605 | | 17 |
| 61 | 2-(4-((2-(dimethylamino)ethyl)oxy)phenyl)-N-(1,3-dithiolan-2-ylmethyl)-3-phenylfuro[2,3-b]pyridin-4-amine | 491.677 | | 20 |
| 62 | N-(2-((3-phenyl-2-(4-((2-(1-piperidinyl)ethyl)oxy)phenyl)furo[2,3-b]pyridin-4-yl)amino)ethyl)acetamide | 498.624 | 499 | 9 |
| 63 | 2-(3-fluoro-4-((2-(1-piperidinyl)ethyl)oxy)phenyl)-3-phenyl-N-(2-(1-piperazinyl)ethyl)furo[2,3-b]pyridin-4-amine | 543.683 | 544 | 6, 7 |
| 64 | 2-(4-(4-morpholinylmethyl)phenyl)-3-phenyl-N-(2-(1-piperazinyl)ethyl)furo[2,3-b]pyridin-4-amine | 497.639 | 498 | 6, 7 |
| 65 | 2-(3-((4-methyl-1-piperazinyl)carbonyl)phenyl)-3-phenylfuro[2,3-b]pyridine | 397.476 | 398 | 16 |
| 66 | 2-(3-((4-methyl-1-piperazinyl)carbonyl)phenyl)-3-phenyl-N-(2-(1-piperazinyl)ethyl)furo[2,3-b]pyridin-4-amine | 524.665 | 525 | 26 |
| 67 | 2-(3-(4-morpholinylcarbonyl)phenyl)-3-phenyl-N-(2-(1-piperazinyl)ethyl)furo[2,3-b]pyridin-4-amine | 511.623 | 512 | 16 |

-continued

| Ex. | Name | Mol. Wt. | MH+ | Scheme |
|---|---|---|---|---|
| 68 | 3-phenyl-2-(3-((phenylmethyl)oxy)phenyl)-N-(2-(1-piperazinyl)ethyl)furo[2,3-b]pyridin-4-amine | 504.631 | 505 | 4, 5 |
| 69 | 2-(3-(4-morpholinylcarbonyl)phenyl)-3-phenylfuro[2,3-b]pyridine | 384.433 | 385 | 16 |
| 70 | 2-(4-(4-(1-methylethyl)-1-piperazinyl)phenyl)-3-phenyl-N-(2-(1-piperazinyl)ethyl)furo[2,3-b]pyridin-4-amine | 524.709 | 525 | 8 |
| 71 | 2-(4-((4-methyl-1-piperazinyl)sulfonyl)phenyl)-3-phenyl-N-(2-(1-piperazinyl)ethyl)furo[2,3-b]pyridin-4-amine | 560.719 | 561 | 6, 7 |
| 72 | ethyl 2-(4-((2-(dimethylamino)ethyl)oxy)phenyl)-4-hydroxy-3-phenylfuro[2,3-b]pyridine-5-carboxylate | 446.5 | | |
| 73 | 3-phenyl-N-((2S)-tetrahydro-2-furanylmethyl)-2-(triethylsilyl)furo[2,3-b]pyridin-4-amine | 408.615 | | 20 |
| 74 | 4-(((methyloxy)methyl)oxy)-3-phenyl-2-(triethylsilyl)furo[2,3-b]pyridine | 369.534 | 370.3 | 20 |
| 75 | ethyl 4-(((methyloxy)methyl)oxy)-3-phenyl-2-(triethylsilyl)furo[2,3-b]pyridine-5-carboxylate | 441.597 | | 20 |
| 76 | 2-(4-((2-(dimethylamino)ethyl)oxy)phenyl)-3-phenyl-N-(2-(1-piperidinyl)ethyl)furo[2,3-b]pyridin-4-amine | 484.64 | 485.2 | 17 |
| 77 | 2-(4-((2-(dimethylamino)ethyl)oxy)phenyl)-N-((1-ethyl-2-pyrrolidinyl)methyl)-3-phenylfuro[2,3-b]pyridin-4-amine | 484.64 | 485.4 | 17 |
| 78 | N-(2-(4-chlorophenyl)ethyl)-2-(4-((2-(dimethylamino)ethyl)oxy)phenyl)-3-phenylfuro[2,3-b]pyridin-4-amine | 512.05 | 512.2 | 17 |
| 79 | 2-(4-((2-(dimethylamino)ethyl)oxy)phenyl)-N-(2-(4-(methyloxy)phenyl)ethyl)-3-phenylfuro[2,3-b]pyridin-4-amine | 507.631 | 508.3 | 17 |
| 80 | 2-(4-((2-(dimethylamino)ethyl)oxy)phenyl)-N-(2-(2-(methyloxy)phenyl)ethyl)-3-phenylfuro[2,3-b]pyridin-4-amine | 507.631 | 508.3 | 17 |
| 81 | 2-(4-((2-(dimethylamino)ethyl)oxy)phenyl)-5-fluoro-N-((2-(methyloxy)cyclobutyl)methyl)-3-phenylfuro[2,3-b]pyridin-4-amine | 489.588 | 490.3 | 20 |
| 82 | 2-(4-((2-(dimethylamino)ethyl)oxy)phenyl)-5-fluoro-3-phenyl-N-((2S)-tetrahydro-2-furanylmethyl)furo[2,3-b]pyridin-4-amine | 475.561 | 476.2 | 20 |
| 83 | 2-(4-((2-(dimethylamino)ethyl)oxy)phenyl)-5-fluoro-3-phenyl-N-(2-(2-pyridinyl)ethyl)furo[2,3-b]pyridin-4-amine | 496.583 | 497.2 | 20 |
| 84 | N-(2-(methyloxy)ethyl)-3-phenyl-2-(4-((2-(1-pyrrolidinyl)ethyl)oxy)phenyl)furo[2,3-b]pyridin-4-amine | 457.571 | | 17 |

Analytical Methods

Unless otherwise indicated all HPLC analyses were run on an HP-1000 or HP-1050 system with an HP Zorbax SB-$C_{18}$ (5μ) reverse phase column (4.6×150 mm) run at 30° C. with a flow rate of 1.00 mL/min. The mobile phase used solvent A ($H_2O$/0.1% TFA) and solvent B ($CH_3CN$/0.1% TFA) with a 20 min gradient from 10% to 90% $CH_3CN$. The gradient was followed by a 2 min return to 10% $CH_3CN$ and a 3 min flush. LC-MS methods:

Unless otherwise noted, the LC-MS analysis of exemplary compounds, intermediates and starting materials described here were conducted using one or both of the following two methods:

Method A:

Samples were run on an HP-1100 system with an HP Zorbax SB-$C_8$ (5μ) reverse phase column (4.6×50 mm) run at 30° C. with a flow rate of 0.75 mL/min. The mobile phase used solvent A ($H_2O$/0.1% AcOH) and solvent B ($CH_3CN$/0.1% AcOH) with a 10 min gradient from 10% to 90% $CH_3CN$. The gradient was followed by a 1 min return to 10% $CH_3CN$ and a 2 min flush.

Method B:

Samples were run on an HP-1100 system with an HP Zorbax SB-$C_8$ (5μ) reverse phase column (4.6×50 mm) run at 30° C. with a flow rate of 1.5 mL/min. The mobile phase used solvent A ($H_2O$/0.1% ACOH) and solvent B ($CH_3CN$/0.1% ACOH) with a 5 min gradient from 10% to 90% $CH_3CN$. The gradient was followed by a 0.5 min return to 10% $CH_3CN$ and a 1.5 min flush.

Proton NMR Spectra:

Unless otherwise indicated all $^1H$ NMR spectra were run on an Varian series Mercury 300 or 400 MHz instrument. All observed protons are reported as parts per million (ppm) downfield from tetramethylsilane (TMS) or other internal reference in the appropriate solvent indicated.

BIOLOGICAL ASSAYS

The following assays can be employed to determine the degree of activity of a compound as a protein kinase inhibitor. Compounds described herein have been tested in one or more of these assays, and have shown activity. Representative compounds of the invention were tested and found to exhibit $IC_{50}$ values of at least <10 μM in any one of the described assays, thereby demonstrating and confirming the utility of the compounds of the invention as protein kinase inhibitors and in the prophylaxis and treatment of immune diseases, hyperproliferative disorders, etc.

LCK-Homogeneous Time Resolved Fluorescent (HTRF) Kinase Assay:

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 μL of compound in 100% DMSO, 15 μL of ATP and biotinylated Gastrin, and 15 μL of LCK KD GST (225-509) for a final volume of 40 μL. The final concentration of gastrin is 1.2 μM. The final concentration of ATP is 0.5 μM (Km app=0.6 μM+/−0.1) and the final concentration of LCK is 250 M. Buffer conditions are as follows: 50 mM HEPES pH 7.5, 50 mM NaCl, 20 mM MgCl, 5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Assays for other kinases are done in a similar way as described above, varying the concentrations of enzyme, peptide substrate, and ATP added to the reaction, depending on the specific activity of the kinase and measured Km's for the substrates.

A vast majority of the exemplary compounds described herein exhibited an average $IC_{50}$ value of 25 μM or less in a human HTRF assay, for the inhibition of the Lck kinase enzyme. Many of exemplary compounds exhibited activity in the human HTFR assay for the inhibition of the Lck kinase enzyme. More specifically, Examples 1-10, 13-17, 24, 26-27, 29-37, 39-45, 48-51, 53, 56-76, 78-83 and compound numbers 8 and 24 of scheme 17, all exhibited an average $IC_{50}$ value of 5 μM or less in the human HTRF assay.

Human Mixed Lymphocyte Reaction (huMLR):

The purpose of this assay is to test the potency of T cell activation inhibitors in an in vitro model of allogeneic T cell stimulation. Human peripheral blood lymphocytes (hPBL; $2\times10^5$/well) are incubated with mitomycin C-treated B lymphoblastoid cells (JY cell line; $1\times10^5$/well) as allogeneic stimulators in the presence or absence of dilutions of potential inhibitor compound in 96-well round-bottom tissue culture plates. These cultures are incubated at 37° C. in 5% $CO_2$ for 6 days total. The proliferative response of the hPBL is measured by $^3$H-thymidine incorporation overnight between days 5 and 6 after initiation of culture. Cells are harvested onto glass fiber filters and $^3$H-thymidine incorporation into DNA is analyzed by liquid scintillation counter.

Jurkat Proliferation/Survival Assay:

The purpose of this assay is to test the general anti-proliferative/cytotoxic effect of compounds on the Jurkat human T cell line. Jurkat cells ($1\times10^5$/well) are plated in 96-well flat-bottom tissue culture plates with or without compound dilutions and cultured for 72 h at 37° C. in 5% $CO_2$. Viable cell number is determined during the last 4 h of culture by adding 10 μL/well WST-1 dye. WST-1 dye conversion relies on active mitochondrial electron transport for reduction of the tetrazolium dye. The dye conversion is read by OD at 450-600 nm.

Anti-CD3/CD28-Induced T Cell IL-2 Secretion and Proliferation Assay:

The purpose of this assay is to test the potency of T cell receptor (TCR; CD3) and CD28 signaling pathway inhibitors in human T cells. T cells are purified from human peripheral blood lymphocytes (hPBL) and pre-incubated with or without compound prior to stimulation with a combination of an anti-CD3 and an anti-CD28 antibody in 96-well tissue culture plates ($1\times10^5$ T cells/well). Cells are cultured for ~20 h at 37° C. in 5% $CO_2$, then secreted IL-2 in the supernatants is quantified by cytokine ELISA (Pierce/Endogen). The cells remaining in the wells are then pulsed with $^3$H-thymidine overnight to assess the T cell proliferative response. Cells are harvested onto glass fiber filters and $^3$H-thymidine incorporation into DNA is analyzed by liquid scintillation counter. For comparison purposes, phorbol myristic acid (PMA) and calcium ionophore can be used in combination to induce IL-2 secretion from purified T cells. Potential inhibitor compounds can be tested for inhibition of this response as described above for anti-CD3 and -CD28 antibodies.

ACK1 Enzymatic Assay $IC_{50}$ values of compounds of Formula I may be assessed as follows. The ACK1 kinase assay utilizes a protein expressed in baculovirus infected Hi-5 cells (a fusion of an N-terminal $(His)_6$ Tag with amino acids 117 to 489 of ACK1) purified by affinity chromatography on a Ni-NTA column. The substrate of for the reaction is ACK1 itself (autophosphorylation) and poly-Glutamic acid-Tyrosine (PGT (4:1), Sigma catalog #PO275). The PGT is coated to Nunc 96 well plates at 80 μg/mL overnight at 4° C. The morning after coating, the plates are washed twice, and 80 μL reaction buffer (10 mM Hepes, pH 7.6; 20 mM $MgCl_2$; 75 mM NaCl, 0.125% TWEEN20 (polyoxyethylene sorbitan monolaurate); 1 mM DTT) with 5 μM ATP are added to each well. Test compounds are added in 10 μL DMSO, and the reaction is started by addition of 10 μL kinase in assay buffer. The reaction proceeds 2 h at room temperature. Next, the plates are washed four times, and the level of tyrosine phosphorylation in a given well is quantified by standard ELISA assay utilizing a phosphotyrosine antibody (PY20, Pierce). The above compounds that have been evaluated exhibited an $IC_{50}$ value of less than about 30 μM with respect to ACK1. More specifically, Examples 1-8, 10, 13-15, 17, 18, 20, 21, 24, 26, 27, 29, 31-37, 39-46, 48-51 and 53, all exhibited an average $IC_{50}$ value of 5 μM or less in the ACK1 kinase enzymatic assay.

ACK1 Cell Based Assay

The ACK1 cell based assay is designed to find inhibitors of ACK1 kinase activity which would be prime candidates for the development of anticancer drugs. The assay is based on the dependence of certain transformed cell lines (e.g. C8 cells, a Ras and E1A transformed fibroblast line) on ACK1 for survival under low serum conditions, whereas other cell lines (e.g. HeLa) do not. This dependency was confirmed utilizing ACK1 specific siRNAs.

For this assay, test (C8) and control (HeLa) cell lines are seeded in 96 well tissue culture plates (BD Falcon) at a density of 2 to $4\times10^4$ in DMEM/F12 (C8) or DMEM (HeLa)

with 0.125% FCS in the presence of ACK1 inhibitors (final DMSO concentration is 0.5%, all tissue culture media are from Cellgro). After 20 to 24 h incubation at 37° C. and 5% $CO_2$, cell viability is determined using the Cytotox One kit (Promega) according to the manufacturer's instructions.

Methods of Use

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

For the treatment of Lck-mediated diseases and other diseases listed above, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) believed to be in need of preventative treatment, such as, for example, pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients and the like as described herein. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

"Treating" within the context of the instant invention, means an alleviation, in whole or in part, of symptoms associated with a disorder or disease, or halt of further progression or worsening of those symptoms, or prevention or prophylaxis of the disease or disorder. Similarly, as used herein, a "therapeutically effective amount" of a compound of the invention refers to an amount of the compound that alleviates, in whole or in part, symptoms associated with a disorder or disease, or halts of further progression or worsening of those symptoms, or prevents or provides prophylaxis for the disease or disorder. For example, within the context of treating patients in need of an inhibitor of ACK1, successful treatment may include a reduction in tumor adhesion and anchorage; an alleviation of symptoms related to a cancerous growth or tumor, or proliferation of diseased tissue; a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. Alternatively, the compounds of the invention can also be administered in conjunction with other anti-proliferative agents including those used in antisense and gene therapy.

One category of suitable antiproliferative agents useful in the present invention is the alkylating agents, a group of highly reactive chemotherapeutics that form covalent linkages with nucleophilic centers (e.g., hydroxyl and carboxyl). Chemically, the alkylating agents can be divided into five groups: nitrogen mustards, ethylenimines, alkylsulfonates, triazenes, and nitrosureas. The nitrogen mustards are frequently useful in, for example, the treatment of chronic lymphocytic leukemia, Hodgkin's disease, malignant lymphoma, small cell lung cancer and breast and testicular cancer. Exemplary nitrogen mustards include chlorambucil, cyclophosphamide, ifosfamide, mechlorethamine, melphalan and uracil mustard. The ethylenimines, the most common of which is thiotepa, may be useful in bladder tumors and in breast and ovarian adenocarcinomas. The alkyl sulfonates are useful in the treatment of chronic myelogenous leukemia and other myeloproliferative disorders. Exemplary alkyl sulfonates include busulfan and piposulfan. The triazines, which include, e.g., dacarbazine, are useful in the treatment of malignant melanomas and sarcomas. Temozolomide, an analog of dacarbazine, may also be used in the methods and compositions of the present invention. Finally, the nitrosureas are especially useful against brain tumors, but also are effective for, e.g., multiple myeloma, malignant melanoma, and lymphoma. Exemplary nitrosureas include carmustine and lomustine.

Another category of antiproliferative agents suitable for use in the present invention is the antimetabolites, structural analogs of normally occurring metabolites that interfere with normal nucleic acid biosynthesis. This category of agents may be subdivided into the folic acid analogs, purine analogs and pyrimidine analogs based on the function of the metabolite with which the agent interferes. The most common folic acid analog is methotrexate, useful in the treatment of choriocarcinoma, leukemias, neoplasms and psoriasis. The purine analogs, such as mercaptopurine, thioguanine and azathioprine, may be useful in leukemias. The pyrimidine analogs are useful in the treatment of, for example, leukemia and carcinomas of the gastrointestinal tract, mammary gland, and bladder. Exemplary pyrimidine analogs include fluorouracil (5-FU), UFT (uracil and ftorafur), capecitabine, gemcitabine and cytarabine.

The vinca alkaloids, natural product-based agents that exert their cytotoxicity by binding to tubulin, represent another category of antiproliferative agents suitable for use in the present invention. The vinca alkaloids are useful in, for example, the treatment of lymphomas, leukemias, and lung, breast, testicular, bladder and head and neck cancers. Exemplary agents include vinblastine, vincristine, vinorelbine and vindesine. The taxanes, agents which promote microtubule assembly, and the podophyllotoxins, agents which inhibit topoisomerases, represent related categories of antiproliferative agents that may be useful in the methods and compositions of the present invention. Exemplary taxanes include paclitaxol and docetaxol, which are useful in breast and lung cancers, among others. Exemplary podophyllotoxins include etoposide (useful in, for example, lymphoma and Hodgkin's disease), teniposide, ironotecan (useful in, for example, colon, rectal and lung cancer) and topotecan, the latter two of which act via inhibition of topoisomerase I.

Antineoplastic antibiotics represent another category of antiproliferative agents useful in the methods and compositions of the present invention. These agents exert their effects by binding to or complexing with DNA. Exemplary agents include daunorubicin, doxorubicin, epirubicin, mitoxantrone, mitomycin, dactinomycin, plicamycin, and bleomycin. The antibiotics are useful in a diverse range of disorders, including Hodgkin's disease, leukemia, lymphoma, and lung cancer.

The methods and compositions of the present invention may comprise other antiproliferative agents, including the platinum complexes (e.g., cisplatin and carboplatin, which are especially useful in the treatment of lung, head and neck, ovarian and breast cancer); enzymes (e.g., L-asparaginase); hormone-related therapy hormone (e.g., tamoxifen, leuprolide, flutamide, megesterol acetate, diethylstilbestrol, prednisone and estradiol cypionate); hydroxyurea; methylhydrazine derivatives such as procarbazine; adrenocortical suppressants, e.g., mitotane, aminoglutethimide; aromatase inhibitors (e.g., anastrozole); and biologic response modifiers (e.g., interferon-A).

Furthermore, the methods and compositions of the present invention may comprise antiproliferative agents that result from the combination of two or more agents including, for example, prednimustine (a conjugate of prednisone and chlorambucil) and estramustine (a conjugate of nornitrogen mustard and estradiol).

The methods and compositions of the present invention may comprise a combination with another kinase inhibitor. Although the present invention is not limited to any particular kinase, kinase inhibitors contemplated for use include tyrphostin AG490 (2-cyano-3-(3,4-dihydroxyphenyl)-N-(benzyl)-2-propenamide), Iressa (ZD1839; Astra Zeneca); Gleevec (STI-571 or imatinib mesylate; Novartis); SU5416 (Pharmacia Corp./Sugen); and Tarceva (OSI-774; Roche/Genentech/OSI Pharmaceuticals).

In another aspect, the instant invention provides pharmaceutical compositions including a compound as described herein and a pharmaceutically acceptable carrier or diluent. Such compositions may be prepared by mixing one or more compounds of the instant invention, or stereoisomers, solvates, pharmaceutically acceptable salts or tautomers thereof, with pharmaceutically acceptable carriers, excipients, binders, diluents or the like, to treat or ameliorate a variety of disorders related to the activity of ACK-1, particularly cancer.

The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described herein, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (2000); and "Pharmaceutics The Science of Dosage Form Design, $2^{nd}$ Ed. (Aulton, ed.) Churchill Livingstone (2002). The following dosage forms are given by way of example and should not be construed as limiting the invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or stereoisomers, solvates, prodrugs, pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, and the like may be added for oral or parenteral administration.

For nasal administration, the pharmaceutical formulations may be a spray or aerosol containing an appropriate solvent and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or a powder suitable for reconstitution as a solution. Both are prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is solid phase at room temperature but liquid phase at those temperatures suitable to release a drug inside the body, such as in the rectum. Various other agents and additives may be used in the preparation of suppositories as is well known to those of skill in the art.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The dosage regimen for treating Lck-mediated diseases and other diseases listed above with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I

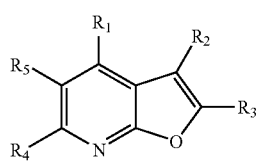

I or a pharmaceutically acceptable salt thereof, wherein
$R^1$ is $NR^6R^7$, $OR^6$ or $SR^6$;
$R^2$ is phenyl substituted by 0, 1, 2, 3 or 4 substituents independently selected from $R^b$ or $R^c$;
$R^3$ is phenyl substituted by 0, 1, 2, 3 or 4 substituents independently selected from $R^b$ or $R^c$;
$R^4$ is $R^a$ or $R^c$;
$R^5$ is $R^a$ or $R^c$;
$R^6$ is —$R^{61}$, —$R^{62}$, —$R^{61}$—$R^{62}$, —$R^{61}$—$R^{64}$, —$R^{62}$—$R^{64}$, —$R^{61}$—$R^{62}$—$R^{64}$, —$R^{61}$—$R^{63}$—$R^{62}$, —$R^{61}$—$R^{63}$—$R^{64}$, —$R^{62}$—$R^{63}$—$R^{64}$, —$R^{61}$—$R^{63}$—$R^{62}$—$R^{64}$ or —$R^{61}$—$R^{62}$—$R^{63}$—$R^{64}$, any of which is substituted by 0, 1, 2, 3 or 4 substituents independently selected from $R^c$;
$R^7$ is $R^a$ or $R^c$;
$R^{61}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;
$R^{62}$ is, independently at each instance, $C_{1-8}$alkyl or $C_{1-8}$alkoxyl;
$R^{63}$ is, independently at each instance, —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;
$R^{64}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;
$R^a$ is, independently at each instance, H or $R^b$;
$R^b$ is, independently at each instance, $C_{1-8}$alkyl, phenyl, piperizinyl, pyridyl, piperidinyl, morpholinyl, pyrrolidinyl, pyrrolyl, imidazolyl, pyrrolidinonyl, pyranyl, tetrahydrofuryl, tetrahydropyranyl, dithiolidinyl, trialkoxysilyl, trialkylsilyl, cyclobutyl, cyclopentyl, cyclolhexyl, or benzyl, each of which is optionally substituted with $C_{1-8}$alkyl, $C_{1-4}$haloalky, F, Cl, Br, I, CN and NO$_2$; and
$R^c$ is, independently at each instance, $C_{1-8}$alkyl, $C_{1-4}$haloalkyl, F, Cl, Br, I, CN, NO$_2$, —C(=O)R$^b$, —C(=O)OR$^a$, —C(=O)NR$^a$R$^a$, —C(=NR$^a$)NR$^a$R$^a$, —OR$^a$, —OC$_{2-6}$alkylR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$.

2. The compound of claim 1 wherein $R^1$ is $NR^6R^7$.

3. The compound of claim 1 wherein $R^6$ is —$R^{62}$, —$R^{61}$—$R^{62}$, —$R^{62}$—$R^{64}$ or —$R^{61}$—$R^{62}$—$R^{64}$.

4. The compound of claim 1 wherein
$R^1$ is $NR^6R^7$;
$R^6$ is —$R^{62}$, —$R^{61}$—$R^{62}$, —$R^{62}$—$R^{63}$, $R^{62}$—$R^{64}$ or —$R^{61}$—$R^{62}$—$R^{64}$;
$R^7$ is H;
$R^{61}$ is phenyl or piperidinyl;
$R^{62}$ is, independently at each instance, $C_{1-8}$alkyl;
$R^{63}$ is, independently at each instance, —C(=O)—, —C(=O)NR$^a$, —O(R$^a$)—, —OC$_{2-6}$alkylNR$^a$—, —OC$_{2-6}$alkylO—, —S—, —S(=O)$_2$NR$^a$—, —N(R$^a$)—, —N(R$^a$)C(=O)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—; and
$R^{64}$ is, independently at each instance, phenyl, piperizinyl, pyridyl, piperidinyl, morpholinyl, pyrrolidinyl, pyrrolyl, imidazolyl, pyrrolidinonyl or tetrahydrofuryl.

5. The compound of claim 1 wherein $R^4$ is H.

6. The compound of claim 1 wherein $R^5$ is H, CN or $C_{1-8}$alkylNH$_2$.

7. The compound of claim 1 wherein
R¹ is selected from tetrahydro-2-furanylmethylamino, 2-(1-piperazinyl)ethylamino, 2-(4-morpholinyl)ethylamino, 4-tert-butylphenylamino, (3-methylphenyl)methylamino, (3-methoxyphenyl)ethylamino, (4-methoxyphenyl)ethylamino, (4-chorophenyl)ethylamino, (2-methoxycyclobutyl)methylamino, isopropylamino, pyrrolidinylethylamino, piperidinylethylamino, (1-phenylmethyl)-4-piperidinylamino, dihydro-indene-1-ylamino, pyridylethylamino, N,N-diethylamino-1-methylbutyl-amino, 2-(N,N-diethylamino)ethyl-1-piperazinyl, dimethylaminobutylamino, 2-(1H-imidazol-1-yl)ethyl-1-piperazinyl, 3-hydroxypropylamino, 3-(1H-imidazol-1-yl)propylamino, 4-ethylcarboxylate-piperidinyl, butanoic acid-4-amino, 2-hydroxy-butanoic acid-4-amino, N-boc-piperazinylethylamino, N-ethyl-piperazinylethylamino, N-(1,2,2,6,6-pentamethyl)-4-piperidine amino, 1-methyl-2-pyrrolidinylmethylamino, 1-ethyl-2-pyrrolidinylmethylamino, cyclopropylmethylamino, phenethylamino, N-(1,3-dithoilan-2-yl)amino, 2-acetamidoethylamino, (methyloxy)methyloxy and 2-(methyloxy)ethylamino.

8. The compound of claim 1 wherein
R³ is selected from 4-((2-(4-morpholinyl)ethyl)oxy)phenyl, 4-(4-(morpholinyl)methyl)phenyl, 4-((2-(1-pyrrolidinyl)ethyl)oxy)phenyl, 4-((2-(1-piperidinyl)ethyl)oxy)phenyl, 3-fluoro-4-((2-(1-piperidinyl)ethyl)oxy)phenyl, 4-((2-(1H-pyrrol-1-yl)ethyl)oxy)phenyl, 4-((2-(N,N-diisopropylethylamino)ethyl)oxy)phenyl, 4-((2-(1H-imidazol-1-yl)ethyl)oxy)phenyl, 4-((2-(1-methyl-3-piperidinyl)methyl)oxy)phenyl, 4-((1-(methyloxy)ethyl)oxy)phenyl, pyridine, 4-((2-(pyrrolidinone)ethyl)oxy)phenyl, 4-((4-morpholinyl)carbonyl)phenyl, 3-((4-morpholinyl)carbonyl)phenyl, 3-((4-methyl-1-piperazinyl)carbonyl)phenyl, 4-((2-(dimethylamino)ethyl)oxy)phenyl, 3-benyloxyphenyl, 4-(4-isopropyl-1-piperazinyl)phenyl, 4-((4-methyl-1-piperazinyl)sulfonyl)phenyl and triethylsilyl.

9. The compound of claim 1, as defined by Formula I

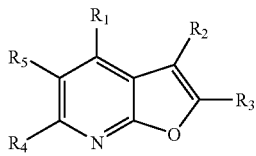

I or a pharmaceutically acceptable salt thereof, wherein
R¹ is selected from tetrahydro-2-furanylmethylamino, 2-(1-piperazinyl)ethylamino, 2-(4-morpholinyl)ethylamino, 4-tert-butylphenylamino, (3-methylphenyl)methylamino, (3-methoxyphenyl)ethylamino, (4-methoxyphenyl)ethylamino, (4-chorophenyl)ethylamino, (2-methoxycyclobutyl)methylamino, isopropylamino, pyrrolidinylethylamino, piperidinylethylamino, (1-phenylmethyl)-4-piperidinylamino, dihydro-indene-1-ylamino, pyridylethylamino, N,N-diethylamino-1-methylbutyl-amino, 2-(N,N-diethylamino)ethyl-1-piperazinyl, dimethylaminobutylamino, 2-(1H-imidazol-1-yl)ethyl-1-piperazinyl, 3-hydroxypropylamino, 3-(1H-imidazol-1-yl)propylamino, 4-ethylcarboxylate-piperidinyl, butanoic acid-4-amino, 2-hydroxy-butanoic acid-4-amino, N-boc-piperazinylethylamino, N-ethyl-piperazinylethylamino, N-(1,2,2,6,6-pentamethyl)-4-piperidine amino, 1-methyl-2-pyrrolidinylmethylamino, 1-ethyl-2-pyrrolidinylmethylamino, cyclopropylmethylamino, phenethylamino, N-(1,3-dithoilan-2-yl)amino, 2-acetamidoethylamino, (methyloxy)methyloxy and 2-(methyloxy)ethylamino;
R² is phenyl substituted by 0, 1 or 2 substituents independently selected from $R^b$ and $R^c$;
R³ is selected from 4-((2-(4morpholinyl)ethyl)oxy)phenyl, 4-(4-(morpholinyl)methyl)phenyl, 4-((2-(1-pyrrolidinyl)ethyl)oxy)phenyl, 4-((2-(1-piperidinyl)ethyl)oxy)phenyl, 3-fluoro-4-((2-(1-piperidinyl)ethyl)oxy)phenyl, 4-((2-(1H-pyrrol-1-yl)ethyl)oxy)phenyl, 4-((2-(N,N-diisopropylethylamino)ethyl)oxy)phenyl, 4-((2-(1H-imidazol-1-yl)ethyl)oxy)phenyl, 4-((2-(1-methyl-3-piperidinyl)methyl)oxy)phenyl, 4-((1-(methyloxy)ethyl)oxy)phenyl, pyridine, 4-((2-(pyrrolidinone)ethyl)oxy)phenyl, 4-((4-morpholinyl)carbonyl)phenyl, 3-((4-morpholinyl)carbonyl)phenyl, 3-((4-methyl-1-piperazinyl)carbonyl)phenyl, 4-((2-(dimethylamino)ethyl)oxy)phenyl, 3-benyloxyphenyl, 4-(4-isopropyl-1-piperazinyl)phenyl, 4-((4-methyl-1-piperazinyl)sulfonyl)phenyl and triethylsilyl;
R⁴ is H; and
R⁵ is H, CN or $C_{1-8}$alkylNH₂.

10. The compound of claim 1 of the structure

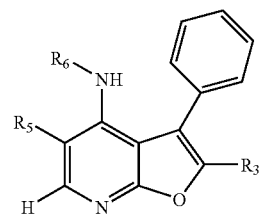

or a pharmaceutically acceptable salt thereof, wherein
R³ is phenyl substituted by 0, 1 or 2 substituents independently selected from $R^b$ and $R^c$;
R⁵ is H, CN or $C_{1-8}$alkylNH₂; and
R⁶ is —$R^{62}$, —$R^{61}$—$R^{62}$, —$R^{62}$—$R^{63}$, —$R^{62}$—$R^{64}$ or —$R^{61}$—$R^{62}$—$R^{64}$, wherein
$R^{61}$ is phenyl or piperidinyl;
$R^{62}$ is, independently at each instance, $C_{1-8}$alkyl;
$R^{63}$ is, independently at each instance, —C(=O)—, —C(=O)NR$^a$—, —O(R$^a$)—, —OC$_{2-6}$alkylNR$^a$—, —OC$_{2-6}$alkylO—, —S—, —S(=O)₂NR$^a$—, —N(R$^a$)—, —N(R$^a$)C(=O)—, —N(R$^a$)S(=O)₂—, —N(R$^a$)S(=O)₂N(R$^a$)—, —NR$^a$C$_{2-6}$alkylN(R$^a$)— or —NR$^a$C$_{2-6}$alkylO—; and
$R^{64}$ is, independently at each instance, phenyl, piperizinyl, pyridyl, piperidinyl, morpholinyl, pyrrolidinyl, pyrrolyl, imidazolyl, pyrrolidinonyl or tetrahydrofuryl.

11. The compound of claim 1 selected from
2,3-diphenyl-N-((2S)-tetrahydro-2-furanylmethyl)furo[2,3-b]pyridin-4-amine;
2,3-diphenyl-N-(2-(1-piperazinyl)ethyl)furo[2,3-b]pyridin-4-amine;
2-(4-((2-(4-morpholinyl)ethyl)oxy)phenyl)-3-phenyl-N-(2-(1-piperazinyl)ethyl)furo[2,3-b]pyridin-4-amine;
N-(2-(4-morpholinyl)ethyl)-2-(4-((2-(4-morpholinyl)ethyl)oxy)phenyl)-3-phenylfuro[2,3-b]pyridin-4-amine;

2,3-diphenyl-4-(((2S)-tetrahydro-2-furanylmethyl)amino)furo[2,3-b]pyridine-5-carbonitrile;
3-phenyl-N-(2-(1-piperazinyl)ethyl)-2-(4-((2-(1-pyrrolidinyl)ethyl)oxy)phenyl)furo[2,3-b]pyridin-4-amine;
3-phenyl-N-(2-(1-piperazinyl)ethyl)-2-(4-((2-(1-piperidinyl)ethyl)oxy)phenyl)furo[2,3-b]pyridin-4-amine;
2,3-diphenyl-4-((2-(1-piperazinyl)ethyl)amino)furo[2,3-b]pyridine-5-carbonitrile;
4-chloro-2,3-diphenyl-N-((2S)-tetrahydro-2-furanylmethyl)furo[2,3-b]pyridin-5-amine;
5-(aminomethyl)-2,3-diphenyl-N-(2-(1-piperazinyl)ethyl)furo[2,3-b]pyridin-4-amine;
4-chloro-2,3-diphenyl-N-(2-(1-piperazinyl)ethyl)furo[2,3-b]pyridin-5-amine;
N,N'-bis(4-(1,1-dimethylethyl)phenyl)-2,3-diphenylfuro[2,3-b]pyridine-4,5-diamine;
3-phenyl-N-(2-(1-piperazinyl)ethyl)-2-(4-((2-(1H-pyrrol-1-yl)ethyl)oxy)phenyl)furo[2,3-b]pyridin-4-amine;
2-(4-((2-(bis(1-methylethyl)amino)ethyl)oxy)phenyl)-3-phenyl-N-(2-(1-piperazinyl)ethyl)furo[2,3-b]pyridin-4-amine;
3-(4-((2-(4-morpholinyl)ethyl)oxy)phenyl)-2-phenyl-N-(2-(1-piperazinyl)ethyl)furo[2,3-b]pyridin-4-amine;
2,3-diphenyl-4-((2-(2-pyridinyl)ethyl)amino)furo[2,3-b]pyridine-5-carbonitrile;
2,3-diphenyl-4-((2-(3-pyridinyl)ethyl)amino)furo[2,3-b]pyridine-5-carbonitrile;
4-(((3-methylphenyl)methyl)amino)-2,3-diphenylfuro[2,3-b]pyridine-5-carbonitrile;
4-((1-methylethyl)amino)-2,3-diphenylfuro[2,3-b]pyridine-5-carbonitrile;
2,3-diphenyl-4-((2-(1-pyrrolidinyl)ethyl)amino)furo[2,3-b]pyridine-5-carbonitrile;
2,3-diphenyl-4-((2-(1-piperidinyl)ethyl)amino)furo[2,3-b]pyridine-5-carbonitrile;
2,3-diphenyl-4-((1-(phenylmethyl)-4-piperidinyl)amino)furo[2,3-b]pyridine-5-carbonitrile;
4-((1S)-2,3-dihydro-1H-inden-1-ylamino)-2,3-diphenylfuro[2,3-b]pyridine-5-carbonitrile;
4-((2-((2S)-1-methyl-2-pyrrolidinyl)ethyl)amino)-2,3-diphenylfuro[2,3-b]pyridine-5-carbonitrile;
2,3-diphenyl-4-((2-(4-pyridinyl)ethyl)amino)furo[2,3-b]pyridine-5-carbonitrile;
7,8-diphenyl-1H-furo[2,3-b]pyrazolo[3,4-d]pyridin-3-amine;
4-(((1R)-4-(diethylamino)-1-methylbutyl)amino)-2,3-diphenylfuro[2,3-b]pyridine-5-carbonitrile;
4-(4-(2-(diethylamino)ethyl)-1-piperazinyl)-2,3-diphenylfuro[2,3-b]pyridine-5-carbonitrile;
4-((4-(dimethylamino)butyl)amino)-2,3-diphenylfuro[2,3-b]pyridine-5-carbonitrile;
4-(4-(2-(1H-imidazol-1-yl)ethyl)-1-piperazinyl)-2,3-diphenylfuro[2,3-b]pyridine-5-carbonitrile;
3-phenyl-2-(4-((2-(1-piperidinyl)ethyl)oxy)phenyl)-N-(2-(4-pyridinyl)ethyl)furo[2,3-b]pyridin-4-amine;
2-(4-((2-(1H-imidazol-1-yl)ethyl)oxy)phenyl)-3-phenyl-N-(2-(1-piperazinyl)ethyl)furo[2,3-b]pyridin-4-amine;
4-((3-hydroxypropyl)amino)-2,3-diphenylfuro[2,3-b]pyridine-5-carbonitrile;
4-((2-(1H-imidazol-1-yl)ethyl)amino)-2,3-diphenylfuro[2,3-b]pyridine-5-carbonitrile;
4-amino-2,3-diphenylfuro[2,3-b]pyridine-5-carbonitrile;
N-(3-(1H-imidazol-1-yl)propyl)-3-phenyl-2-(4-((2-(1-piperidinyl)ethyl)oxy)phenyl)furo[2,3-b]pyridin-4-amine;
N-(7,8-diphenyl-1H-furo[2,3-b]pyrazolo[3,4-d]pyridin-3-yl)acetamide;
ethyl 1-(5-cyano-2,3-diphenylfuro[2,3-b]pyridin-4-yl)-4-piperidinecarboxylate;
3-phenyl-2-(4-((2-(1-piperidinyl)ethyl)oxy)phenyl)-N-(2-(3-pyridinyl)ethyl)furo[2,3-b]pyridin-4-amine;
N-1-,N-1-dimethyl-N~3~-(3-phenyl-2-(4-((2-(1-piperidinyl)ethyl)oxy)phenyl)furo[2,3-b]pyridin-4-yl)-1,3-propanediamine;
2-(4-(((1-methyl-3-piperidinyl)methyl)oxy)phenyl)-3-phenyl-N-(2-(1-piperazinyl)ethyl)furo[2,3-b]pyridin-4-amine;
4-((5-cyano-2,3-diphenylfuro[2,3-b]pyridin-4-yl)amino)butanoic acid;
(2S)-4-((5-cyano-2,3-diphenylfuro[2,3-b]pyridin-4-yl)amino)-2-hydroxybutanoic acid;
1,1-dimethylethyl 4-(2-((5-cyano-3-phenyl-2-(4-((2-(1-pyrrolidinyl)ethyl)oxy)phenyl)furo[2,3-b]pyridin-4-yl)amino)ethyl)-1-piperazinecarboxylate;
3-phenyl-4-((2-(1-piperazinyl)ethyl)amino)-2-(4-((2-(1-pyrrolidinyl)ethyl)oxy)phenyl)furo[2,3-b]pyridine-5-carbonitrile;
N-(7,8-diphenyl-1H-furo[2,3-b]pyrazolo[3,4-d]pyridin-3-yl)benzamide;
4-((2-(4-ethyl-1-piperazinyl)ethyl)amino)-2,3-diphenylfuro[2,3-b]pyridine-5-carbonitrile;
2-(4-((2-(methyloxy)ethyl)oxy)phenyl)-3-phenyl-N-(2-(1-piperazinyl)ethyl)furo[2,3-b]pyridin-4-amine;
N-(7,8-diphenyl-1H-furo[2,3-b]pyrazolo[3,4-d]pyridin-3-yl)-N'-ethylurea;
N-(1,1-dimethylethyl)-N'-(7,8-diphenyl-1H-furo[2,3-b]pyrazolo[3,4-d]pyridin-3-yl)urea;
N-(1,2,2,6,6-pentamethyl-4-piperidinyl)-3-phenyl-2-(4-((2-(1-piperidinyl)ethyl)oxy)phenyl)furo[2,3-b]pyridin-4-amine;
N-(2-(1-methyl-2-pyrrolidinyl)ethyl)-3-phenyl-2-(4-((2-(1-piperidinyl)ethyl)oxy)phenyl)furo[2,3-b]pyridin-4-amine;
N-(2,6-dichlorophenyl)-N'-(7,8-diphenyl-1H-furo[2,3-b]pyrazolo[3,4-d]pyridin-3-yl)urea;
3-phenyl-N-(2-(1-piperazinyl)ethyl)-2-(3-pyridinyl)furo[2,3-b]pyridin-4-amine;
1-(2-((4-(3-phenyl-4-(((2S)-tetrahydro-2-furanylmethyl)amino)furo[2,3-b]pyridin-2-yl)phenyl)oxy)ethyl)-2-pyrrolidinone;
2-(4-(4-morpholinylcarbonyl)phenyl)-3-phenyl-N-((2S)-tetrahydro-2-furanylmethyl)furo[2,3-b]pyridin-4-amine;
N-(cyclopropylmethyl)-2-(4-((2-(dimethylamino)ethyl)oxy)phenyl)-3-phenylfuro[2,3-b]pyridin-4-amine;
2-(4-((2-(dimethylamino)ethyl)oxy)phenyl)-N-(2-(4-morpholinyl)ethyl)-3-phenylfuro[2,3-b]pyridin-4-amine;
2-(4-((2-(dimethylamino)ethyl)oxy)phenyl)-3-phenyl-N-(2-phenylethyl)furo[2,3-b]pyridin-4-amine;
2-(4-((2-(dimethylamino)ethyl)oxy)phenyl)-N-(1,3-dithiolan-2-ylmethyl)-3-phenylfuro[2,3-b]pyridin-4-amine;
N-(2-((3-phenyl-2-(4-((2-(1-piperidinyl)ethyl)oxy)phenyl)furo[2,3-b]pyridin-4-yl)amino)ethyl)acetamide;
2-(3-fluoro-4-((2-(1-piperidinyl)ethyl)oxy)phenyl)-3-phenyl-N-(2-(1-piperazinyl)ethyl)furo[2,3-b]pyridin-4-amine;
2-(4-(4-morpholinylmethyl)phenyl)-3-phenyl-N-(2-(1-piperazinyl)ethyl)furo[2,3-b]pyridin-4-amine;
2-(3-((4-methyl-1-piperazinyl)carbonyl)phenyl)-3-phenylfuro[2,3-b]pyridine;
2-(3-((4-methyl-1-piperazinyl)carbonyl)phenyl)-3-phenyl-N-(2-(1-piperazinyl)ethyl)furo[2,3-b]pyridin-4-amine;

2-(3-(4-morpholinylcarbonyl)phenyl)-3-phenyl-N-(2-(1-piperazinyl)ethyl)furo[2,3-b]pyridin-4-amine;

3-phenyl-2-(3-((phenylmethyl)oxy)phenyl)-N-(2-(1-piperazinyl)ethyl)furo[2,3-b]pyridin-4-amine;

2-(3-(4-morpholinylcarbonyl)phenyl)-3-phenylfuro[2,3-b]pyridine;

2-(4-(4-(1-methylethyl)-1-piperazinyl)phenyl)-3-phenyl-N-(2-(1-piperazinyl)ethyl)furo[2,3-b]pyridin-4-amine;

2-(4-((4-methyl-1-piperazinyl)sulfonyl)phenyl)-3-phenyl-N-(2-(1-piperazinyl)ethyl)furo[2,3-b]pyridin-4-amine;

ethyl 2-(4-((2-(dimethylamino)ethyl)oxy)phenyl)-4-hydroxy-3-phenylfuro[2,3-b]pyridine-5-carboxylate;

3-phenyl-N-((2S)-tetrahydro-2-furanylmethyl)-2-(triethylsilyl)furo[2,3-b]pyridin-4-amine;

4-(((methyloxy)methyl)oxy)-3-phenyl-2-(triethylsilyl)furo[2,3-b]pyridine;

ethyl 4-(((methyloxy)methyl)oxy)-3-phenyl-2-(triethylsilyl)furo[2,3-b]pyridine-5-carboxylate;

2-(4-((2-(dimethylamino)ethyl)oxy)phenyl)-3-phenyl-N-(2-(1-piperidinyl)ethyl)furo[2,3-b]pyridin-4-amine;

2-(4-((2-(dimethylamino)ethyl)oxy)phenyl)-N-((1-ethyl-2-pyrrolidinyl)methyl)-3-phenylfuro[2,3-b]pyridin-4-amine;

N-(2-(4-chlorophenyl)ethyl)-2-(4-((2-(dimethylamino)ethyl)oxy)phenyl)-3-phenylfuro[2,3-b]pyridin-4-amine;

2-(4-((2-(dimethylamino)ethyl)oxy)phenyl)-N-(2-(4-(methyloxy)phenyl)ethyl)-3-phenylfuro[2,3-b]pyridin-4-amine;

2-(4-((2-(dimethylamino)ethyl)oxy)phenyl)-N-(2-(2-(methyloxy)phenyl)ethyl)-3-phenylfuro[2,3-b]pyridin-4-amine;

2-(4-((2-(dimethylamino)ethyl)oxy)phenyl)-5-fluoro-N-((2-(methyloxy)cyclobutyl)methyl)-3-phenylfuro[2,3-b]pyridin-4-amine;

2-(4-((2-(dimethylamino)ethyl)oxy)phenyl)-5-fluoro-3-phenyl-N-((2S)-tetrahydro-2-furanylmethyl)furo[2,3-b]pyridin-4-amine;

2-(4-((2-(dimethylamino)ethyl)oxy)phenyl)-5-fluoro-3-phenyl-N-(2-(2-pyridinyl)ethyl)furo[2,3-b]pyridin-4-amine;

2-{4-[2-(dimethylamino)ethoxy]phenyl}-N-[(3-methylthien-2-yl)methyl]-3-phenylfuro[2,3-b]pyridin-4-amine;

(2R)-2-{[(2-{4-[2-(dimethylamino)ethoxy]phenyl}-3-phenylfuro[2,3-b]pyridin-4-yl)amino]methyl}cyclopentanone;

2-{4-[2-(dimethylamino)ethoxy]phenyl}-3-phenyl-N-[(2S)-tetrahydrofuran-2-ylmethyl]furo[2,3-b]pyridin-4-amine;

3-phenyl-2-[4-(2-pyrrolidin-1-ylethoxy)phenyl]-N-[(2S)-tetrahydrofuran-2-ylmethyl]furo[2,3-b]pyridin-4-amine; and N-(2-(methyloxy)ethyl)-3-phenyl-2-(4-((2-(1-pyrrolidinyl)ethyl)oxy)phenyl)furo[2,3-b]pyridin-4-amine.

12. A pharmaceutical composition comprising a compound of claim 1 and a pharmaceutically acceptable carrier or diluent.

13. A pharmaceutical composition comprising a compound of claim 11 and a pharmaceutically acceptable carrier or diluent.

\* \* \* \* \*